(12) United States Patent
Fischer et al.

(10) Patent No.: US 12,024,564 B2
(45) Date of Patent: Jul. 2, 2024

(54) HUMANIZED ANTI-IL-1R3 ANTIBODIES

(71) Applicant: SANOFI BIOTECHNOLOGY, Paris (FR)

(72) Inventors: Stephan Fischer, Weilheim (DE); Michael Brandt, Munich (DE); Linda Veronique Kazandjian, Munich (DE)

(73) Assignee: SANOFI BIOTECHNOLOGY (FR)

( * ) Notice: Subject to any disclaimer, the term of this patent is extended or adjusted under 35 U.S.C. 154(b) by 227 days.

(21) Appl. No.: 17/410,153

(22) Filed: Aug. 24, 2021

(65) Prior Publication Data

US 2022/0089751 A1 Mar. 24, 2022

Related U.S. Application Data

(62) Division of application No. 16/099,059, filed as application No. PCT/EP2017/060925 on May 8, 2017, now Pat. No. 11,203,642.

(30) Foreign Application Priority Data

May 6, 2016 (EP) ..................... 16168617

(51) Int. Cl.
C07K 16/28 (2006.01)

(52) U.S. Cl.
CPC ...... C07K 16/2866 (2013.01); *C07K 2317/24* (2013.01); *C07K 2317/52* (2013.01); *C07K 2317/76* (2013.01)

(58) Field of Classification Search
None
See application file for complete search history.

(56) References Cited

U.S. PATENT DOCUMENTS

| | | |
|---|---|---|
| 5,202,238 A | 4/1993 | Fell, Jr. et al. |
| 5,204,244 A | 4/1993 | Fell et al. |
| 5,283,179 A | 2/1994 | Wood |
| 5,641,641 A | 6/1997 | Wood |
| 5,650,289 A | 7/1997 | Wood |
| 6,280,955 B1 | 8/2001 | Cao |
| 6,586,207 B2 | 7/2003 | Tirrell et al. |
| 6,602,684 B1 | 8/2003 | Umana et al. |
| 7,390,880 B2 | 6/2008 | Bednarik et al. |
| 10,906,971 B2 | 2/2021 | Fischer et al. |
| 11,198,728 B2 | 12/2021 | Fischer et al. |
| 11,203,642 B2 | 12/2021 | Fischer et al. |
| 11,639,392 B2 | 5/2023 | Fischer et al. |
| 2003/0026806 A1 | 2/2003 | Witte et al. |
| 2004/0214988 A1 | 10/2004 | Tirrell et al. |
| 2012/0251531 A1 | 10/2012 | Baehner et al. |
| 2014/0017167 A1 | 1/2014 | Fioretos et al. |
| 2015/0315179 A1 | 11/2015 | Jiang et al. |
| 2019/0106487 A1 | 4/2019 | Fischer et al. |
| 2019/0194336 A1 | 6/2019 | Fischer et al. |
| 2020/0140559 A1 | 5/2020 | Fischer et al. |
| 2020/0407438 A1 | 12/2020 | Fischer et al. |
| 2022/0169718 A1 | 6/2022 | Fischer et al. |

FOREIGN PATENT DOCUMENTS

| | | |
|---|---|---|
| CN | 1934072 A | 3/2007 |
| CN | 102939304 A | 2/2013 |
| EP | 0488470 A1 | 6/1992 |
| EP | 1255780 A1 | 11/2002 |
| EP | 1633787 A1 | 3/2006 |
| JP | 2014-511348 A | 5/2014 |
| WO | WO 1996/023067 A1 | 8/1996 |
| WO | WO 1998/048032 A2 | 10/1998 |
| WO | WO 2001/055216 A1 | 8/2001 |
| WO | WO 2002/064630 A2 | 8/2002 |
| WO | WO 2003/014309 A2 | 2/2003 |
| WO | WO 2002/064630 A3 | 8/2003 |
| WO | WO 2003/073238 A2 | 9/2003 |
| WO | WO 2004/022718 A2 | 3/2004 |
| WO | WO 2004/065540 A2 | 8/2004 |
| WO | WO 2004/100987 A2 | 11/2004 |
| WO | WO 2004/106377 A1 | 12/2004 |
| WO | WO 2005/035727 A2 | 4/2005 |
| WO | WO 2005/044859 A2 | 5/2005 |
| WO | WO 2005/073164 A1 | 8/2005 |
| WO | WO 2005/074524 A2 | 8/2005 |

(Continued)

OTHER PUBLICATIONS

Alam, J. and Cook, J.L., Reporter Genes: Application to the Study of Mammalian Gene Transcription. Anal Biochem. 1990; 188(2):245-54.

Ali, S. et al., IL-1 receptor Accessory Protein is Essential for IL-33-induced Activation of T Lymphocytes and Mast Cells. Proc Natl Acad Sci USA, 2007; 104(47):18660-5.

Balagurunathan, Y. et al., Gene Expression Profiling-Based Identification of Cell-Surface Targets for Developing Multimeric Ligands in Pancreatic Cancer. Mol Cancer Ther. 2008: 7(9):3071-80.

Barbas, C.F., III et al., In vitro Evolution of a Neutralizing Human Antibody to Human Immunodeficiency Virus Type 1 to Enhance Affinity and Broaden Strain Cross-Reactivity. Proc Natl Acad Sci USA. 1994; 91(9):3809-13.

(Continued)

*Primary Examiner* — Ruixiang Li
(74) *Attorney, Agent, or Firm* — LATHROP GPM LLP; James H. Velema, Esq.; Michael J. Spellberg, Esq.

(57) ABSTRACT

The present invention relates to humanized antibodies that specifically bind to IL-1R3 or a fragment or derivative thereof or a polypeptide that contains at least a portion of said antibody that is sufficient to confer IL-1R3 binding specificity. Said antibodies inhibit IL-1R3 induced NFkB activity. They also inhibit IL-1alpha, IL-1beta, IL-33, and/or IL-36 stimulated NFkB activity.

Figure 14:
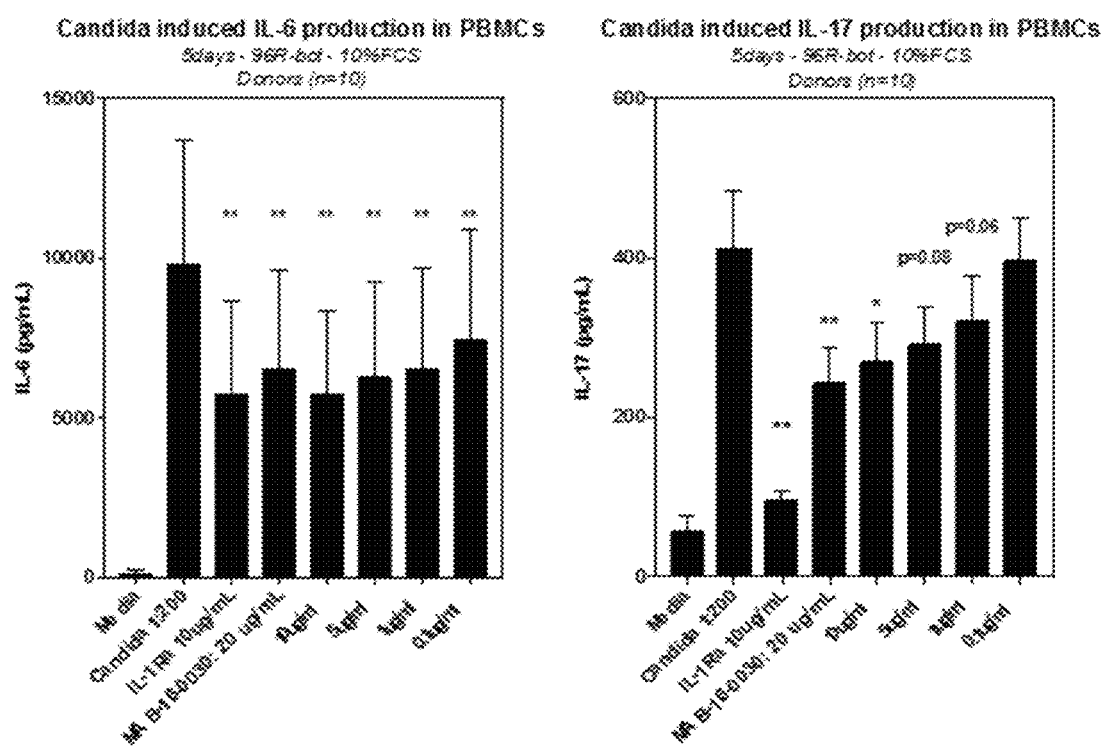

The invention further relates to use of said humanized antibody in the treatment of an IL-1R3 mediated disease such as cancer.

The present invention also encompasses a pharmaceutical composition comprising a pharmaceutically acceptable carrier and a therapeutically effective amount of the antibody according to the invention. The pharmaceutical composition can be used in treating a IL-1R3 mediated disease such as cancer.

15 Claims, 20 Drawing Sheets

Specification includes a Sequence Listing.

(56) References Cited

FOREIGN PATENT DOCUMENTS

| | | |
|---|---|---|
| WO | WO 2007/003041 A1 | 1/2007 |
| WO | WO 2007/031875 A2 | 3/2007 |
| WO | WO 2008/045140 A1 | 4/2008 |
| WO | WO 2009/120903 A2 | 10/2009 |
| WO | WO 2010/108127 A1 | 9/2010 |
| WO | WO 2011/021014 A2 | 2/2011 |
| WO | WO 2011/124718 A1 | 10/2011 |
| WO | WO 2011/147903 A1 | 12/2011 |
| WO | WO 2012/098407 A1 | 7/2012 |
| WO | WO 2012/142391 A1 | 10/2012 |
| WO | WO 2012/177595 A1 | 12/2012 |
| WO | WO 2013/023015 A2 | 2/2013 |
| WO | WO 2013/165894 A2 | 11/2013 |
| WO | WO 2013/165894 A3 | 11/2013 |
| WO | WO 2014/100772 A1 | 6/2014 |
| WO | WO 2014/113433 A1 | 7/2014 |
| WO | WO 2015/132602 A1 | 9/2015 |
| WO | WO 2016/020502 A1 | 2/2016 |
| WO | WO 2016/207304 A2 | 12/2016 |

OTHER PUBLICATIONS

Bardin, "Canakinumab for the Patient With Difficult-to-Treat Gouty Arthritis: Review of the Clinical Evidence", Joint Bone Spine, 2015, 82: eS9-eS16.

Barnes, L.M. et al., Advances in Animal Cell Recombinant Protein Production: GS-NS0 Expression System. Cytotechnology. 2000; 32(2):109-23.

Barnes, L.M. et al., Characterization of the Stability of Recombinant Protein Production in the GS-NS0 Expression System. Biotech Bioeng. 2001; 73(4):261-70.

Brueggemann, M. et al., Comparison of the Effector Functions of Human Immunoglobulins Using a Matched Set of Chimeric Antibodies. J Exp Med. 1987; 166(5):1351-61.

Capel, P.J.A. et al., Heterogeneity of Human IgG Fc Receptors. Immunomethods. 1994; 4(1):2534.

Carter, P. et al., Humanization of an Anti-p185$^{HER2}$ Antibody for Human Cancer Therapy. Proc Natl Acad Sci USA. 1992; 89(10):4285-9.

Chin, J.W. and Schultz, P.G., In Vivo Photocrosslinking with Unnatural Amino Acid Mutagenesis. ChemBioChem. 2002; 3(11):1135-7.

Chin, J.W. et al., Addition of a Photocrosslinking Amino Acid to the Genetic Code of *Escherichia co/i*. Proc Natl Acad Sci U.S.A. 2002; 99(17):11020-4.

Chin, J.W. et al., Addition of p-Azido-L-phenylalanine to the Genetic Code of *Escherichia coli*. J Amer Chem Soc. 2002; 124:9026-7.

Cullinan et al., The IL-1 Receptor Accessory Protein Is an Essential Component of the IL-1 Receptor, J. Immunology, Nov. 15, 1998, 161(10): 5614-5620.

Daeron, M., Fc Receptor Biology. Annu Rev Immunol. 1997; 15:203-34.

Davis, R.S. et al., Fc Receptor Homologs: Newest Members of a Remarkably Diverse Fc Receptor Gene Family. Immunol Rev. 2002; 190:123-36.

De Haas et al., Fcγ Receptors of Phagocytes. J Lab Clin Med. 1995; 126(4):330-41.

De Wet, J.R. et al., Firefly Luciferase Gene: Structure and Expression in Mammalian Cells. Mol Cell Biol. 1987; 7:725-37.

De Wildt, R.M. and Hoet, R.M., The Recovery of Immunoglobulin Sequences from Single Human B Cells by Clonal Expansion. Methods Mol Biol. 2002; 178:121-31.

Dinarello, C.A., Immunological and Inflammatory Functions of the Interleukin-1 Family, Annual Review of Immunology, 2009, 27: 519-550.

Dinarello, C.A., Interleukin-1 in the Pathogenesis and Treatment of Inflammatory Diseases. Blood. 2011; 117(14):3720-32.

Diu, A. et al., Activation of Resting Human B Cells by Helper T-cell Clone Supernatant: Characterization of a Human B-cell-activating Factor. Proc Natl Acad Sci USA. 1987; 84(24):91404.

Durocher, Y. et al., High-level and High-throughput Recombinant Protein Production by Transient Transfection of Suspension-growing Human 293-EBNA1 Cells. Nucleic Acids Res. 2002; 30(2):E9 (9 pages).

Edelman, et al., "The Covalent Structure of an Entire γG Immunoglobulin Molecule", PNAS USA, May 1, 1969, 63(1): 78-85.

Extended European Search Report for European Patent Application No. 21191122.7, dated Nov. 24, 2021.

Geisse, S. et al., Eukaryotic Expression Systems: A Comparison. Protein Expr Purif. 1996; 8(3):271-82.

Guyer, R.L. et al., Immunoglobulin Binding by Mouse Intestinal Epithelial Cell Receptors. J Immunol. 1976; 117(2):587-93.

Hawkins, R.E. et al., Selection of Phage Antibodies by Binding Affinity: Mimicking Affinity Maturation. J Mol Biol. 1992; 226(3):889-96.

Hoffmann, P. et al., Murine Bone Marrow-derived Macrophages Constitute Feeder Cells for Human B Cell Hybridomas. J Immunol Methods. 1996; 196(1):85-91.

Huang, J. et al., Recruitment of IRAK to the Interleukin 1 Receptor Complex Requires Interleukin 1 Receptor Accessory Protein. Proc Natl Acad Sci USA. 1997; 94(24):12829-32.

Huston, J.S., Protein Engineering of Single-Chain Fv Analogs and Fusion Proteins. Methods Enzymol. 1991; 203:46-88.

International Preliminary Report on Patentability for Patent Application No. PCT/EP2016/064588, dated Dec. 26, 2017.

International Search Report and Written Opinion for PCT International Patent Application No. PCT/EP2018/061846, dated Jul. 6, 2018, 12 pages.

International Search Report and Written Opinion for PCT International Patent Application No. PCT/EP2017/060925, dated Jul. 7, 2017, 13 pages.

International Search Report and Written Opinion dated Jan. 11, 2017 by the International Searching Authority for Patent Application No. PCT/EP2016/064588, which was filed on Jun. 23, 2016 and published as WO 2016/207304 on Dec. 29, 2016 (Inventor—Fischer et al.; Applicant—MAB Discovery GMBH) (15 pages).

Jackson, J.R. et al., In vitro Antibody Maturation. Improvement of a High Affinity, Neutralizing Antibody Against IL-1 R. J Immunol. 1995; 154(7):3310-9.

Jaras, M. et al., Isolation and Killing of Candidate Chronic Myeloid Leukemia Stem Cells by Antibody Targeting of IL-1 Receptor Accessory Protein. Proc Natl Acad Sci USA. 2010; 107(37):16280-5.

Jefferis, R. et al., Interaction Sites on Human IgG-Fc for FOR: Current Models. Immunol Lett. 2002; 82(1-2):57-65.

Johnson, G. and Wu, T.T., Kabat Database and Its Applications: 30 Years After the First Variability Plot. Nucleic Acids Res. 2000; 28(1):214-8.

Kabat, E.A. et al., Sequences of Proteins of Immunological Interest, 5th ed., Public Health Service, National Institutes of Health, Bethesda, MD (1991).

Kaufman, R.J., Overview of Vector Design for Mammalian Gene Expression. Mol Biotechnol. 2000; 16(2):151-60.

Kim, J.-K et al., Localization of the Site of Murine IgG1 Molecule that is Involved in Binding to the Murine Intestinal Fc Receptor. Eur J Immunol. 1994; 24(10):2429-34.

Kodituwakko, A.P. et al., Isolation of Antigen-Specific B Cells. Immunol Cell Biol. 2003; 81(3):163-70.

Krupke, D.M. et al., The Mouse Tumor Biology Database. Nat Rev Cancer. 2008; 8(6):459-65.

Lefranc, M.-P., Nomenclature of the Human Immunoglobulin Genes. Curr Protoc Immunol. 2000; Appendix 1P (37 pages).

Li, X. et al., Mutant Cells That Do Not Respond to Interleukin-1 (IL-1) Reveal a Novel Role for IL-1 Receptor-Associated Kinase. Mol Cel Biol. 1999; 19(7):4643-52.

Love, T.W. et al., Recombinant Antibodies Possessing Novel Effector Functions. Methods Enzymol. 1989; 178:515-27.

Makrides, S.C., Components of Vectors for Gene Transfer and Expression in Mammalian Cells. Protein Expr Purif. 1999; 17(2):183-202.

(56) References Cited

OTHER PUBLICATIONS

Mansur et al., Engagement of IL-1 receptor accessory protein (IL-1RAcP) with the monoclonal antibody AY19 provides co-activating signals and prolongs the CD2-induced proliferation of peripheral blood lymphocytes, Immunol Lett., 2011, 139(1): 52-57.
Marks, J.D. et al., Bypassing Immunization: Building High Affinity Human Antibodies by Chain Shuffling. BioTechnology. 1992; 10(7):779-83.
Morrison, S.L. et al., Chimeric Human Antibody Molecules: Mouse Antigen-Binding Domains with Human Constant Region Domains. Proc Natl Acad Sci USA. 1984; 81(21):6851-5.
Neuberger, M.C. et al., A Hapten-Specific Chimaeric IgE with Human Physiological Effector Function. Nature. 1985; 314(6008):268-70.
Norderhaug, L. et al., Versatile Vectors for Transient and Stable Expression of Recombinant Antibody Molecules in Mammalian Cells. J Immunol Methods. 1997; 204(1):77-87.
Orencole, S.F. and Dinarello, C.A., Characterization of a Subclone (D10S) of the D10.G4.1 Helper T-cell Line which Proliferates to Attomolar Concentrations of Interleukin-1 in the Absence of Mitogens. Cytokine. 1989; 1(1):14-22.
Orlandi, R. et al., Cloning Immunoglobulin Variable Domains for Expression by the Polymerase Chain Reaction. Proc Natl Acad Sci USA. 1989; 86(10):3833-7.
Ow, D.W. et al., Transient and Stable Expression of the Firefly Luciferase Gene in Plant Cells and Transgenic Plants. Science. 1986; 234(4778):856-9.
Paul, ed., 1993, Fundamental Immunology 3$^{rd}$ Edition, Raven Press, New York at pp. 292-295.
Raju, T.S., Glycosylation Variations with Expression Systems and Their Impact on Biological Activity of Therapeutic Immunoglobulins. BioProcess Intl. 2003; 1(4):44-53.
Ravetch, J.V. and Kinet, J.P., Fc Receptors. Annu Rev Immunol. 1991; 9:457-92.
Riechmann, L. et al., Reshaping Human Antibodies for Therapy. Nature. 1988; 332:323-7.
Routier, F.H., The Glycosylation Pattern of a Humanized IgGI Antibody (D1.3) Expressed in CHO Cells. Glycoconj J. 1997; 14(2):201-7.
Roy, A. et al., Increased Efficiency of 7-Irradiated versus Mitomycin C-Treated Feeder Cells for the Expansion of Normal Human Cells in Long-Term Cultures. J Hematother Stem Cell Res. 2001; 10(6):873-80.
Schier, R. et al., Identification of Functional and Structural Amino-Acid Residues by Parsimonious Mutagenesis. Gene. 1995; 169(2):147-55.
Schlaeger, E.-J and Christensen, K., Transient Gene Expression in Mammalian Cells Grown in Serum-Free Suspension Culture. Cytotechnology. 1999; 30(1-3):71-83.
Schlaeger, E.-J., The Protein Hydrolysate, Primatone RL, is a Cost-Effective Multiple Growth Promoter of Mammalian Cell Culture in Serum-Containing and Serum-Free Media and Displays Anti-Apoptosis Properties. J Immunol Methods. 1996; 194(2):191-9.
Sonderman, P. et al., The 3.2-A Crystal Structure of the Human IgG1 Fc Fragment-FcγRIII Complex. Nature. 2000; 406(6793):267-73.
Towne, J.E. et al., Interleukin (IL)-1 F6, IL-1F8, and IL-F9 Signal Through IL-1 Rrp2 and IL-1RAcP to Activate the Pathway Leading to NF-KB and MAPKs. J Biol Chem. 2004; 279(14):13677-13688.
Umaña, P. et al., Engineered Glycoforms of an Antineuro-Blastoma IgG1 with Optimized Antibody-Dependent Cellular Cytotoxic Activity. Nature Biotechnol. 1999; 17(2):176-80.
Vajdos, et al., "Comprehensive Functional Maps of the Antigen-Binding Site of An Anti-ErbB2 Antibody Obtained with Shotgun Scanning Mutagenesis", Journal of Molecular Biology, vol. 320, No. 2, pp. 415-428. (Jul. 1, 2002).
Wang, L. and Schultz, P.G., Expanding the Genetic Code. Chem Commun. 2002; 0(1):1-11.
Wedemayer, G.J. et al., Structural Insights into the Evolution of an Antibody Combining Site. Science. 1997; 276(5319):1665-9.
Wen, L. et al., Limiting Dilution Assay for Human B Cells Based on Their Activation by Mutant EL4 Thymoma Cells: Total and Anti-Malaria Responder B Cell Frequencies. Eur J Immunol. 1987; 17(6):887-92.
Werner, R.G., Appropriate Mammalian Expression Systems for Biopharmaceuticals. Arzneimittelforschung. 1998; 48(8):870-80.
Windheim, M. et al., Interleukin-1 (IL-1) Induces the Lys63-linked Polyubiquitination of IL-1 Receptor-Associated Kinase 1 to Facilitate NEMO Binding and the Activation of 1-K13a Kinase. Mol Cell Biol. 2008; 28(5):1783-91.
Wood, K.V., Firefly Luciferase: A New Tool for Molecular Biologists. Promega Notes. 1990; 28:1-3.
Yamane-Ohnuki, N. and Satoh, M., Production of Therapeutic Antibodies with Controlled Fucosylation. MAbs. 2009; 1(3):230-6.
Yelton, D.E. et al., Affinity Maturation of the BR96 Anti-Carcinoma Antibody by Codon-Based Mutagenesis. J Immunol. 1995; 155(4):1994-2004.
Yoon, D.-Y. and Dinarello, C.A., Antibodies to Domains II and III of the IL-1 Receptor Accessory Protein Inhibit IL-1R Activity But Not Binding: Regulation of IL-1 Responses Is Via Type I Receptor, Not the Accessory Protein. J Immunol. 1998; 160:3170-9.
Yoon, D.-Y. and Dinarello, C.A., Differential Effects of Anti-IL-1 R Accessory Protein Antibodies on IL-1a or IL-1 R-induced Production of PGE(2) and IL-6 from 3T3-L1 Cells. J Biochem Mol Biol. 2007; 40(4): 562-70.
Zhao et al., Construction of hybridoma cells with IL1RAP as a new marker for leukemia stem cells and detection of its monoclonal antibody, J Experimental Hematology, Dec. 2013, 12(6): 1390-1393.
Zubler, R.H. et al., Polyclonal B Cell Responses in the Presence of Defined Filler Cells: Complementary Effects of Lipopolysaccharide and Anti-Immunoglobulin Antibodies. Eur J Immunol. 1984; 14(4):357-63.
Paul, Fundamental Immunology, 3rd Edition, Raven Press, New York, 1993, pp. 292-295.
Zhao et al., Construction of hydridoma calls with ILIRAP as a new marker for leukemia stem cells and detection of its monoclonal antibody, Journal of Exp Hematology, 2013, 21(6): 1390-1393.
Zubler, Polyclonal B Cell Responses in the Presence of Defined Filler Cells: Complementary Effects of Lipopolysaccharide and Anti-Immunoglobulin Antibodies, Eur J Immunol., 1984, 14(4):,357-363.
Rudikoff et al., Single amino acid substitution altering antigen-binding specificity, PNAS USA, Mar. 1982, 79: 1979-1983.
Vajdos et al., Comprehensive Functional Maps of the Antigen-Binding Site of an Anti-ErbB2 Antibody Obtained with Shotgun Scanning Mutagenesis, Journal of Molecular Biology, 2002, 320: 415-428.
U.S. Appl. No. 15/739,410 2019/0106487 U.S. Pat. No. 10,906,971, filed Dec. 22, 2017 Apr. 11, 2019 Feb. 2, 2021, Stephan Fischer, Monoclonal Anti-IL-1RACP Antibodies.
U.S. Appl. No. 16/898,074 2020/0407438 U.S. Pat. No. 11,198,728, filed Jun. 10, 2020 Dec. 31, 2020 Dec. 14, 2021, Stephan Fischer, Monoclonal Anti-IL-1RACP Antibodies.
U.S. Appl. No. 17/522,600 2022/0169718, filed Nov. 9, 2021 Jun. 2, 2022, Stephan Fischer, Monoclonal Anti-IL-1RACP Antibodies.
U.S. Appl. No. 16/099,059 2019/0194336 U.S. Pat. No. 11,203,642, filed Nov. 5, 2018 Jun. 27, 2019 Dec. 21, 2021, Stephan Fischer, Humanized Anti-IL-1R3 Antibodies.
U.S. Appl. No. 16/612,052 2020/0140559 U.S. Pat. No. 11,639,392, filed Nov. 8, 2019 May 7, 2020 May 2, 2023, Stephan Fischer, Anti-IL-1R3 Antibodies For Use In Inflammatory Conditions.
U.S. Appl. No. 18/184,759, filed Mar. 16, 2023, Stephan Fischer, Anti-IL-1R3 Antibodies For Use In Inflammatory Conditions.

Fig. 1: Sequences (amino acids in one letter code)

VH complete:     SEQ ID NO: 1-34 and SEQ ID NO: 173
    VL complete:     SEQ ID NO: 35-68 and SEQ ID NO: 174

CDR-H1:     SEQ ID NO: 69-85
    CDR-H2:     SEQ ID NO: 86-102
    CDR-H3:     SEQ ID NO: 103-119

CDR-L1:     SEQ ID NO: 120-136
    CDR-L2:     SEQ ID NO: 137-153
    CDR-L3:     SEQ ID NO: 154-170 and 175

CR-L:     SEQ ID NO: 171
    CR-H:     SEQ ID NO: 172

| mAB name | SEQ ID NO. | Complete Heavy-chain VR sequence |
|---|---|---|
| MAB-15-0139 | 1 | EVQLEESGGGLVQPGGSLRLSCAASGFSFSSSYWICWVRQAPGKGLEWVSCIYTGSGGTYYASWEKGRFTISRDNSKNTLYLQMNSLRAEDTAVYFCARDPGYSSWLWGQGTLVTVSS |
| MAB-15-0106 | 2 | EVQLEESGGDLVQPGGSLRLSCAASGFSFSSSHYMCWVRQAPGKGLEWVSCIYAGSSGNTYYANWAKGRFTISRDNSKNTLYLQMNSLRAEDTAVYFCARVDASSSGSWDLWGQGTLVTVSS |
| MAB-15-0108 | 3 | EVQLEESGGRLVQPGGSLRLSCAVSGIDLSSYAMGWVRQAPGKGLEYVSVITSSATTYYASWAKGRFTISRDNSKNTLYLQMNSLRAEDTAVYFCARGGPGYSTNTHYAFDPWGQGTLVTVSS |
| MAB-15-0110 | 4 | EVQLEESGGRVVQPGRSLRLSCAVSGIDLDNYAMGWVRQAPGKGLEYVAVISSDGFFYDASWAKGRFTISRDNSKNTLYLQMNSLRAEDTAVYFCARDRGTSTGSLDLWGQGTLVTVSS |
| MAB-15-0117 | 5 | EVQLEESGGRLVQPGGSLRLSCAASGFSLSSYYMSWVRQAPGKGLEWVSIISGSASTYYATWAKGRFTISRDNSKNTLYLQMNSLRAEDTAVYFCARTHYAAVAGYGYASRLDLWGQGTLVTVSS |
| MAB-15-0121 | 6 | EVQLEESGGDLVQPGGSLRLSCAASGFSFSSNYWICWVRQAPGKGLELVSCIYTSTGNTWYASWAKGRFTISRDNSKNTLYLQMNSLRAEDTAVYFCARDLLVVTSFNLWGQGTLVTVSS |
| MAB-15-0140 | 7 | EVQLEESGGDLVQPGGSLRLSCAASGFSFSSSYYMCWVRQAPGKGLEWVSCIYAGSSGVTYYASWAKGRFTISRDNSKNTLYLQMNSLRAEDTAVYFCASETDGNYFNLWGQGTLVTVSS |
| MAB-15-0115 | 8 | EVQLEQSGGGLVQPGGSLRLSCAASGFSLSTSYWRCWVRQAPGKGLEWVSCIYAGSGDVTYYANWVNGRFTISRDNSKNTLYLQMNSLRAEDTAVYYCASGVGFGYFNLWGQGTLVTVSS |
| MAB-15-0125 | 9 | EVQLEESGGGLVQPGGSLRLSCAASGIDFSSYYYMCWVRQAPGKGLEWVSCIFIGYGDVTWYASWAKGRFTISRDNSKNTLYLQMNSLRAEDTAVYFCARALGSSGYRVNLWGQGTLVTVSS |
| MAB-15-0119 | 10 | EVQLEESGGRLVQPGGSLRLSCAASGFSLSSYWMSWVRQAPGKGLEWVSMIYGSGYTYYASWAKGRFTISRDNSKNTLYLQMNSLRAEDTAVYFCARDPQYFILWGQGTLVTVSS |
| MAB-15-0109 | 11 | EVQLEESGGRLVQPGGSLRLSCAVSGFSLSSYDMSWVRQAPGKGLEWVSTIYIGGTTAYASWPKGRFTISRDNSKNTLYLQMNSLRAEDTAVYFCARLQGANYYNSLALWGQGTLVTVSS |

| | | |
|---|---|---|
| MAB-15-0097 | 12 | EVQLVESGGGLVQPGGSLRLSCAASGFDFSSNYYMCWVRQAPGKGLELVSCIYTNSGNTWSASWAKGRFTISRDNSKNTLYLQMNSLRAEDTAVYFCARDLNYPDTSNLWGQGTLVTVSS |
| MAB-15-0135 | 13 | EVQLEESGGDLVQPGGSLRLSCAASGFSFSFGYYMCWVRQAPGKGLEWVSCIYGDSSDTLYANWAKGRFTISRDNSKNTLYLQMNSLRAEDTAVYFCARYPGGSYYNLWGQGTLVTVSS |
| MAB-15-0133 | 14 | EVQLEESGGDLVQPGGSLRLSCAASGFSFSSTYYMCWVRQAPGKGLEWVSCIYAGSSGSTYYASWAKGRFTISRDNSKNTLYLQMNSLRAEDTAVYFCARVDGSSSGSWDLWGQGTLVTVSS |
| MAB-15-0107 | 15 | EVQLEESGGDLVQPGGSLRLSCAASGISFSSSDFMCWVRQAPGKGLEWVSCIYAGSSVSIYYATWAKGRFTISRDNSKNTLYLQMNSLRAEDTAVYFCARSTGSVGRGFNLWGQGTLVTVSS |
| MAB-15-0128 | 16 | EVQLVESGGGLVQPGGSLRLSCAASGFSFSSIYYMCWVRQAPGKGLEWVSCIYTGNSDFTYYANWAKGRFTISRDNSKNTLYLQMNSLRAEDTAVYFCARFRDDYASLKLWGQGTLVTVSS |
| MAB-15-0116 | 17 | EVQLEESGGGLVQPGGSLRLSCAASGFSFSSGYDMCWVRQAPGKGLEWVSCIYTGSGSTYYANWAKGRFTISRDNSKNTLYLQMNSLRAEDTAVYFCARNSNDWMYFNLWGQGTLVTVSS |
| MAB-16-0004 | 18 | EVQLEQSGGGLVQPGGSLRLSCAASGFSFSSSYWICWVRQAPGKGLEWVACIYTGSGGTYYASWEKGRFTISKTSSTTLYLQMNSLRAEDTAVYFCARDPGYSSWLWGQGTLVTVSS |
| MAB-16-0009 | 19 | EVQLEESGGDLVQPGASLRLSCAASGFSFSSSHYMCWVRQAPGKGLEWVACIYAGSSGNTYYANWAKGRFTISKTNSKNTLYLQMNSLRAEDTAVYFCARVDASSSGSWDLWGQGTLVTVSS |
| MAB-16-0028 | 20 | EVQLLESGGRLVQPGTSLRLSCAVSGIDLSSYAMGWVRQAPGKGLEYVGVITSSATTYYASWAKGRFTISKTSSTTLYLQMNSLRAEDTAVYFCARGGPGYSTNTHYAFDPWGQGTLVTVSS |
| MAB-16-0031 | 21 | EVQLEESGGRVVQPGTSLRLSCAVSGIDLDNYAMGWVRQAPGKGLEYVAVISSDGFFYDASWAKGRFTISKANSKNTLYLQMNSLRAEDTAVYFCARDRGTSTGSLDLWGQGTLVTVSS |
| MAB-16-0043 | 22 | QVQLEESGGRLVQPGTSLRLSCAASGFSLSSYYMSWVRQAPGKGLEWVAIISGSASTYYATWAKGRFTISKTSTTLYLQMNSLRAEDTAVYFCARTHYAAVAGYGYASRLDLWGQGTLVTVSS |
| MAB-16-0049 | 23 | QVQLQESGGDLVQPGGSLRLSCAASGFSFSSNYWICWVRQAPGKGLELVACIYTSTGNTWYASWAKGRFTISRDNSKNTLYLQMNSLRAEDTAVYFCARDLLVVTSFNLWGQGTLVTVSS |
| MAB-16-0045 | 24 | EVQLVESGGDLVQPGASLRLSCAASGFSFSSSYYMCWVRQAPGKGLEWVACIYAGSSGVTYYASWAKGRFTISDTSSTTLYLQMNSLRAEDTAVYFCASETDGNYFNLWGQGTLVTVSS |
| MAB-16-0040 | 25 | EVQLEQSGGGLVQPGGSLRLSCAASGFSLSTSYWRCWVRQAPGKGLEWVACIYAGSGDVTYYANWVNGRFTISRDNSKSTLYLQMNSLRAEDTAVYYCASGVGFGYFNLWGQGTLVTVSS |
| MAB-16-0036 | 26 | EVQLEESGGGLVQPGGSLRLSCAASGIDFSSYYYMCWVRQAPGKGLEWVACIFIGYGDVTWYASWAKGRFTISKANSKNTLYLQMNSLRAEDTAVYFCARALGSSGYRVNLWGQGTLVTVSS |
| MAB-16-0046 | 27 | QVQLEESGGRLVQPGASLRLSCAASGFSLSSYWMSWVRQAPGKGLEWVAMIYGSGYTYYASWAKGRFTISTTSTTLYLQMNSLRAEDTAVYFCARDPQYFILWGQGTLVTVSS |
| MAB-16-0030 | 28 | EVQLEESGGRLVQPGTSLRLSCAVSGFSLSSYDMSWVRQAPGKGLEWVSTIYIGGTTAYASWPKGRFTISKTNSKNTLYLQMNSLRAEDTAVYFCARLQGANYYNSLALWGQGTLVTVSS |
| MAB-16-0021 | 29 | QVQLVESGGGLVQPGGSLRLSCAASGFDFSSNYYMCWVRQAPGKGLELVACIYTNSGNTWSASWAKGRFTISKTNSTTLYLQMNSLRAEDTAVYFCARDLNYPDTSNLWGQGTLVTVSS |

Fig. 1 (cont.)

| mAb Name | SEQ ID NO. | |
|---|---|---|
| MAB-16-0019 | 30 | EVQLEESGGDLVQPGGSLRLSCAASGFSFSFGYYMCWVRQAPGKGLEWVACIYGDSSDTLYANWAKGRFTISKTNSKNTLYLQMNSLRAEDTAVYFCARYPGGSYYNLWGQGTLVTVSS |
| MAB-16-0015 | 31 | QVQLQESGGDLVQPGASLRLSCAASGFSFSSTYYMCWVRQAPGKGLEWVACIYAGSSGSTYYASWAKGRFTISKNSSTLYLQMNSLRAEDTAVYFCARVDGSSSGSWDLWGQGTLVTVSS |
| MAB-16-0027 | 32 | EVQLEESGGDLVQPGASLRLSCAASGISFSSSDFMCWVRQAPGKGLEWVACIYAGSSVSIYYATWAKGRFTISKASSTTLYLQMNSLRAEDTAVYFCARSTGSVGRGFNLWGQGTLVTVSS |
| MAB-16-0048 | 33 | EVQLVESGGGLVQPGGSLRLSCAASGFSFSSIYYMCWVRQAPGKGLEWVGCIYTGNSDFTYYANWAKGRFTISRDNSKSTLYLQMNSLRAEDTAVYFCARFRDDYASLKLWGQGTLVTVSS |
| MAB-16-0041 | 34 | QVQLQESGGGLVQPGGSLRLSCTASGFSFSSGYDMCWVRQAPGKGLEWVGCIYTGSGSTYYANWAKGRFTISKDNSKTTLYLQMNSLRAEDTAVYFCARNSNDWMYFNLWGQGTLVTVSS |

| mAb Name | SEQ ID NO. | Complete k-Light chain VR sequence |
|---|---|---|
| MAB-15-0139 | 35 | DIVMTQSPSSLSASVGDRVTITCQASESISNYLSWYQQKPGQAPKLLIYLASTLASGVPSRFSGSGSGTDFTLTISSLQPEDFATYYCQNWWVIEHNGAAFGGGTKVVIK |
| MAB-15-0106 | 36 | DIQMTQSPSSLSASVGDRVTITCQASESIYSNLAWYQQKPGQAPKLLIYAASLLASGVPSRFSGSGSGTDFTLTISSLQPEDFATYYCQSASYSTGPDWTFGQGTKVVIK |
| MAB-15-0108 | 37 | DIQMTQSPSSLSASVGDRVTITCQASQSIYIYLSWYQQKPGQAPKLLIYDASKLASGVPSRFSGSGSGTDFTLTISSLQPEDFATYYCQQGATTYNVDNVFGQGTKVVIK |
| MAB-15-0110 | 38 | DIVMTQSPSSLSASVGDRVTITCQASENIGNGLAWYQQKPGQAPKLLIYGASTLASGVPSRFSGSGSGTDFTLTISSLQPEDFATYYCQCTYWNPDYIGGAFGGGTKVVIK |
| MAB-15-0117 | 39 | DIQMTQSPSSLSASVGDRVTITCLASEDIYSGISWYQQKPGKAPKLLIYAASNLESGVPSRFSGSGSGTDFTLTISSLQPEDFATYYCLGGYSYSNTGPTFGQGTKVEIK |
| MAB-15-0121 | 40 | DIVMTQSPSSLSASVGDRVTITCQASEDIYSNLAWFQQKPGQAPKLLIYGASTLASGVPSRFSGSGSGTEFTLTISSLQPEDFATYYCLGVCTDISTDDLYNAFGQGTKVVIK |
| MAB-15-0140 | 41 | DIVMTQSPSSLSASVGDRVTITCQASEDIYSNLAWFQQKPGQAPKLLIYRASTLASGVPSRFSGSGSGTEFTLTISSLQPEDFATYYCLGVYTYSTDIHAFGGGTKVVIK |
| MAB-15-0115 | 42 | DIVMTQSPSSLSASVGDRVTITCQASEDIYSNLAWFQQKPGQAPKLLIYDASTLASGVPSRFSGSGSGTEFTLTISSLQPEDFATYYCLGVYTHISADNAFGGGTKVVIK |
| MAB-15-0125 | 43 | DIQMTQSPSSLSASVGDRVTITCQASENIYSSLAWYQQKPGQAPKLLIYDASDLASGVPSRFSGSGSGTDFTLTISSLQPEDFATYYCQQGYYSGGTDNDVFGGGTKVVIK |
| MAB-15-0119 | 44 | DIVMTQSPSSLSASVGDRVTITCQSSQSVDGNNLLSWYQQKPGQAPKLLIYDASNLASGVPSRFSGSGSGTDFTLTISSLQPEDFATYYCQGSYYSSSWYNVFGQGTKVVIK |
| MAB-15-0109 | 45 | DIQMTQSPSSLSASVGDRVTITCQASQSIYSFLSWYQQKPGQAPKLLIYAASDLESGVPSRFSGSGSGTDFTLTISSLQPEDFATYYCQCNYIIDYGAFGQGTKVVIK |
| MAB-15-0097 | 46 | DIQMTQSPSSLSASVGDRVTITCQASQSIGYYLAWYQQKPGQAPKLLIYRASTLASGVPSRFSGSGSGTDFTLTISSLQPEDFATYYCQSYYNSDSDAFGQGTKVVIK |
| MAB-15-0135 | 47 | DIVMTQSPSSLSASVGDRVTITCQASQTISINLAWYQQKPGQAPKLLIYYASTLASGVPSRFSGSGSGTDFTLTISSLQPEDFATYYCQQGYTEDNIDNTFGQGTKVVIK |
| MAB-15-0133 | 48 | DIQMTQSPSSLSASVGDRVTITCQASQNIYSNLAWYQQKPGQAPKLLIYAASLLASGVPSRFSGSGSGTDFTLTISSLQPEDFATYYCQGAVYSGNTEWAFGQGTKVVIK |
| MAB-15-0107 | 49 | DIVMTQSPSSLSASVGDRVTITCQASQSVYNSNHLSWYQQKPGQAPKLLIYSASTLASGVPSRFSGSGSGTDFTLTISSLQPEDFATYYCQGEFSCVSADCIAFGGGTKVVIK |

Fig. 1 (cont.)

| | | |
|---|---|---|
| MAB-15-0128 | 50 | DIQMTQSPSSLSASVGDRVTITCQASQSISSYLSWYQQKPGQAPKLLIYGASNLASGVPSR FSGSGSGTDFTLTISSLQPEDFATYYCQCTYYDNNYGGAFGGGTKVVIK |
| MAB-15-0116 | 51 | DIVMTQSPSSLSASVGDRVTITCQASESISANYWSWYQQKPGQAPKLLIYGASTLASGVPS RFSGSGSGTDFTLTISSLQPEDFATYFCQSWYYSGSGSYHSWAFGQGTKVVIK |
| MAB-16-0004 | 52 | DIVMTQSPSSLSASVGDRVTITCQASESISNYLSWYQQKPGQAPKLLIYLASTLASGVPSRF SGSGSGTDFTLTISSLQPEDFATYYCQNWWVIEHNGAAFGGGTKVVIK |
| MAB-16-0009 | 53 | AIQMTQSPSSLSASVGDRVTITCQASESIYSNLAWYQQKPGQAPKLLIYAASLLASGVPSRF SGSGSGTDYTLTISSLQPEDFATYYCQSASYSTGPDWTFGQGTKVVIK |
| MAB-16-0028 | 54 | AIRMTQSPSSLSASVGDRVTITCQASQSIYIYLSWYQQKPGQAPKLLIYDASKLASGVPSRF SGSGSGTDFTLTISSLQPEDFATYYCQQGATTYNVDNVFGQGTKVVIK |
| MAB-16-0031 | 55 | ELVMTQSPSSLSASVGDRVTITCQASENIGNGLAWYQQKPGQAPKLLIYGASTLASGVPS RFSGSGSGTDFTLTISSLQPEDFATYYCQCTYWNPDYIGGAFGGGTKVVIK |
| MAB-16-0043 | 56 | AIQMTQSPSSLSASVGDRVTITCLASEDIYSGISWYQQKPGKAPKLLIYAASNLESGVPSRFS GSGSGTDYTLTISSLQPEDFATYYCLGGYSYSNTGPTFGQGTKVEIK |
| MAB-16-0049 | 57 | DIVMTQSPSSLSASVGDRVTITCQASEDIYSNLAWFQQKPGQAPKLLIYGASTLASGVPSR FSGSGSGTEFTLTISSLQPEDFATYYCLGVCTDISTDDLYNAFGQGTKVVIK |
| MAB-16-0045 | 58 | DIVMTQSPSSLSASVGDRVTITCQASEDIYSNLAWFQQKPGQAPKLLIYRASTLASGVPSR FSGSGSGTEFTLTISSLQPEDFATYYCLGVYTYSTDIHAFGGGTKVVIK |
| MAB-16-0040 | 59 | ELVMTQSPSSLSASVGDRVTITCQASEDIYSNLAWFQQKPGQAPKLLIYDASTLASGVPSR FSGSGSGTEFTLTISSLQPEDFATYYCLGVYTHISADNAFGGGTKVEIK |
| MAB-16-0036 | 60 | ALQMTQSPSSLSASVGDRVTITCQASENIYSSLAWYQQKPGQAPKLLIYDASDLASGVPSR FSGSGSGTDFTLTISSLQPEDFATYYCQQGYYSGGTDNDVFGGGTKVVIK |
| MAB-16-0046 | 61 | NIVMTQSPSSLSASVGDRVTITCQSSQSVDGNNLLSWYQQKPGQAPKLLIYDASNLASGV PSRFSGSGSGTDFTLTISSLQPEDFATYYCQGSYYSSSWYNVFGQGTKVVIK |
| MAB-16-0030 | 62 | DVQMTQSPSSLSASVGDRVTITCQASQSIYSFLSWYQQKPGQAPKLLIYAASDLESGVPSR FSGSGSGTDFTLTISSLQPEDFATYYCQCNYIIDYGAFGQGTKVVIK |
| MAB-16-0021 | 63 | DIQMTQSPSSLSASVGDRVTITCQASQSIGYYLAWYQQKPGQAPKLLIYRASTLASGVPSR FSGSGSGTDFTLTISSLQPEDFATYYCQSYYNSDSDAFGQGTKVVIK |
| MAB-16-0019 | 64 | AIVMTQSPSSLSASVGDRVTITCQASQTISNLAWYQQKPGQAPKLLIYYASTLASGVPSRF SGSGSGTDFTLTISSLQPEDFATYYCQQGYTEDNIDNTFGQGTKVVIK |
| MAB-16-0015 | 65 | AIQMTQSPSSLSASVGDRVTITCQASQNIYSNLAWYQQKPGQAPKLLIYAASLLASGVPSR FSGSGSGTDYTLTISSLQPEDFATYYCQGAVYSGNTEWAFGQGTKVVIK |
| MAB-16-0027 | 66 | DIVMTQSPSSLSASVGDRVTITCQASQSVYNSNHLSWYQQKPGQAPKLLIYSASTLASGVP SRFSGSGSGTDFTLTISSLQPEDFATYYCQGEFSCVSADCIAFGGGTKVVIK |
| MAB-16-0048 | 67 | DVVMTQSPSSLSASVGDRVTITCQASQSISSYLSWYQQKPGQAPKLLIYGASNLASGVPSR FSGSGSGTDFTLTISSLQPEDFATYYCQCTYYDNNYGGAFGGGTKVEIK |
| MAB-16-0041 | 68 | DIVMTQSPSSLSASVGDRVTITCQASESISANYWSWYQQKPGQAPKLLIYGASTLASGVPS RFSGSGSGTDFTLTISSLQPEDFATYFCQSWYYSGSGSYHSWAFGQGTKVVIK |

| mAB name | | SEQ ID NO. | CDR-H1 | SEQ ID NO. | CDR-H2 | SEQ ID NO. | CDR-H3 |
|---|---|---|---|---|---|---|---|
| MAB-15-0139 | MAB-16-0004 | 69 | SSYWIC | 86 | CIYTGSGGTYYASWEKG | 103 | DPGYSSWL |
| MAB-15-0106 | MAB-16-0009 | 70 | SSHYMC | 87 | CIYAGSSGNTYYANWAKG | 104 | VDASSSGSWDL |
| MAB-15-0108 | MAB-16-0028 | 71 | SYAMG | 88 | VITSSATTYYASWAKG | 105 | GGPGYSTNTHYAFDP |

Fig. 1 (cont.)

| mAB name | | SEQ ID NO. | CDR-H1 | SEQ ID NO. | CDR-H2 | SEQ ID NO. | CDR-H3 |
|---|---|---|---|---|---|---|---|
| MAB-15-0110 | MAB-16-0031 | 72 | NYAMG | 89 | VISSDGFFYDASWAKG | 106 | DRGTSTGSLDL |
| MAB-15-0117 | MAB-16-0043 | 73 | SYYMS | 90 | IISGSASTYYATWAKG | 107 | THYAAVAGYGYASRLDL |
| MAB-15-0121 | MAB-16-0049 | 74 | SNYWIC | 91 | CIYTSTGNTWYASWAKG | 108 | DLLVVTSFNL |
| MAB-15-0140 | MAB-16-0045 | 75 | SSYYMC | 92 | CIYAGSSGVTYYASWAKG | 109 | ETDGNYFNL |
| MAB-15-0115 | MAB-16-0040 | 76 | TSYWRC | 93 | CIYAGSGDVTYYANWVNG | 110 | GVGFGYFNL |
| MAB-15-0125 | MAB-16-0036 | 77 | SYYMC | 94 | CIFIGYGDVTWYASWAKG | 111 | ALGSSGYRVNL |
| MAB-15-0119 | MAB-16-0046 | 78 | SYWMS | 95 | MIYGSGYTYYASWAKG | 112 | DPQYFIL |
| MAB-15-0109 | MAB-16-0030 | 79 | SYDMS | 96 | TIYIGGTTAYASWPKG | 113 | LQGANYYNSLAL |
| MAB-15-0097 | MAB-16-0021 | 80 | SNYYMC | 97 | CIYTNSGNTWSASWAKG | 114 | DLNYPDTSNL |
| MAB-15-0135 | MAB-16-0019 | 81 | FGYYMC | 98 | CIYGDSSDTLYANWAKG | 115 | YPGGSYYNL |
| MAB-15-0133 | MAB-16-0015 | 82 | STYYMC | 99 | CIYAGSSGSTYYASWAKG | 116 | VDGSSSGSWDL |
| MAB-15-0107 | MAB-16-0027 | 83 | SSDFMC | 100 | CIYAGSSVSIYYATWAKG | 117 | STGSVGRGFNL |
| MAB-15-0128 | MAB-16-0048 | 84 | SIYYMC | 101 | CIYTGNSDFTYYANWAKG | 118 | FRDDYASLKL |
| MAB-15-0116 | MAB-16-0041 | 85 | SGYDMC | 102 | CIYTGSGSTYYANWAKG | 119 | NSNDWMYFNL |

| mAB name | | SEQ ID NO. | CDR-L1 | SEQ ID NO. | CDR-L2 | SEQ ID NO. | CDR-L3 |
|---|---|---|---|---|---|---|---|
| MAB-15-0139 | MAB-16-0004 | 120 | QASESISNYLS | 137 | LASTLAS | 154 | QNWWVIEHNGAA |

Fig. 1 (cont.)

| | | | | | | | |
|---|---|---|---|---|---|---|---|
| MAB-15-0106 | MAB-16-0009 | 121 | QASESIYSNLA | 138 | AASLLAS | 155 | QSASYSTGPDWT |
| MAB-15-0108 | MAB-16-0028 | 122 | QASQSIYIYLS | 139 | DASKLAS | 156 | QQGATTYNVDNV |
| MAB-15-0110 | MAB-16-0031 | 123 | QASENIGNGLA | 140 | GASTLAS | 157 | QCTYWNPDYIGGA |
| MAB-15-0117 | MAB-16-0043 | 124 | LASEDIYSGIS | 141 | AASNLES | 158 | LGGYSYSNTGPT |
| MAB-15-0121 | MAB-16-0049 | 125 | QASEDIYSNLA | 142 | GASTLAS | 159 | LGVCTDISTDDLYNA |
| MAB-15-0140 | MAB-16-0045 | 126 | QASEDIYSNLA | 143 | RASTLAS | 160 | LGVYTYSTDIHA |
| MAB-15-0115 | MAB-16-0040 | 127 | QASEDIYSNLA | 144 | DASTLAS | 161 | LGVYTHISADNA |
| MAB-15-0125 | MAB-16-0036 | 128 | QASENIYSSLA | 145 | DASDLAS | 162 | QQGYYSGGTDNDV |
| MAB-15-0119 | MAB-16-0046 | 129 | QSSQSVDGNNLLS | 146 | DASNLAS | 163 | QGSYYSSSWYNV |
| MAB-15-0109 | MAB-16-0030 | 130 | QASQSIYSFLS | 147 | AASDLES | 164 | QCNYIIDYGA |
| MAB-15-0097 | MAB-16-0021 | 131 | QASQSIGYYLA | 148 | RASTLAS | 165 | QSYYNSDSDA |
| MAB-15-0135 | MAB-16-0019 | 132 | QASQTISINLA | 149 | YASTLAS | 166 | QQGYTEDNIDNT |
| MAB-15-0133 | MAB-16-0015 | 133 | QASQNIYSNLA | 150 | AASLLAS | 167 | QGAVYSGNTEWA |
| MAB-15-0107 | MAB-16-0027 | 134 | QASQSVYNSNHLS | 151 | SASTLAS | 168 | QGEFSCVSADCIA |
| MAB-15-0128 | MAB-16-0048 | 135 | QASQSISSYLS | 152 | GASNLAS | 169 | QCTYYDNNYGGA |
| MAB-15-0116 | MAB-16-0041 | 136 | QASESISANYWS | 153 | GASTLAS | 170 | QSWYYSGSGSYHSWA |

Fig. 1 (cont.)

| SEQ ID NO. | Constant region sequences (CR) |
|---|---|
| 171 | RTVAAPSVFIFPPSDEQLKSGTASVVCLLNNFYPREAKVQWKVDNALQSGNSQESVTEQDSKDSTYSLS STLTLSKADYEKHKVYACEVTHQGLSSPVTKSFNRGEC |
| 172 | ASTKGPSVFPLAPSSKSTSGGTAALGCLVKDYFPEPVTVSWNSGALTSGVHTFPAVLQSSGLYSLSSVVT VPSSSLGTQTYICNVNHKPSNTKVDKKVEPKSCDKTHTCPPCPAPEAAGGPSVFLFPPKPKDTLMISRTP EVTCVVVDVSHEDPEVKFNWYVDGVEVHNAKTKPREEQYNSTYRVVSVLTVLHQDWLNGKEYKCKVS NKALPAPIEKTISKAKGQPREPQVYTLPPSREEMTKNQVSLTCLVKGFYPSDIAVEWESNGQPENNYKT TPPVLDSDGSFFLYSKLTVDKSRWQQGNVFSCSVMHEALHNHYTQKSLSLSPG |

| mAB name | SEQ ID NO. | Complete Heavy-chain VR seq |
|---|---|---|
| MAB-16-0150 | 173 | EVQLLESGGRLVQPGTSLRLSCAVSGIDLSSYAMGWVRQAPGKGLEYVGVITSSATTYYAS WAKGRFTISKTSSKNTLYLQMNSLRAEDTAVYFCARGGPGYSTNTHYAFDPWGQGTLVT VSS |

| mAB name | SEQ ID NO. | Complete light-chain VR seq |
|---|---|---|
| MAB-16-0149 | 174 | DVQMTQSPSSLSASVGDRVTITCQASQSIYSFLSWYQQKPGQAPKLLIYAASDLESGVPSR FSGSGSGTDFTLTISSLQPEDFATYYCQSNYIIDYGAFGQGTKVVIK |
| | | CDR-L3 |
| MAB-16-0149 | 175 | QSNYIIDYGA |

| mAB name | CDR-H1 SEQ ID NO. | CDR-H2 SEQ ID NO. | CDR-H3 SEQ ID NO. | CDR-L1 SEQ ID NO. | CDR-L2 SEQ ID NO. | CDR-L3 SEQ ID NO. | VH SEQ ID NO. | VL SEQ ID NO. |
|---|---|---|---|---|---|---|---|---|
| MAB-16-0150 | 71 | 88 | 105 | 122 | 139 | 156 | 173 | 54 |
| MAB-16-0149 | 79 | 96 | 113 | 130 | 147 | 175 | 28 | 174 |

Fig. 1 (cont.)

Fig.2: Human IL-1R3 ELISA

| Antibody ID | huIL1RaP ELISA EC50 [ng/ml] |
|---|---|
| MAB-16-0015 | 1,6 |
| MAB-16-0019 | 28,1 |
| MAB-16-0021 | 20,8 |
| MAB-16-0004 | 8,0 |
| MAB-16-0009 | 4,9 |
| MAB-16-0027 | 5,3 |
| MAB-16-0030 | 4,5 |
| MAB-16-0040 | 6,6 |
| MAB-16-0043 | 13,2 |
| MAB-16-0046 | 7,4 |
| MAB-16-0049 | 20,6 |
| MAB-16-0028 | 6,0 |
| MAB-16-0031 | 8,2 |
| MAB-16-0041 | 15,2 |
| MAB-16-0036 | 5,9 |
| MAB-16-0045 | 28,4 |
| MAB-16-0048 | 7,4 |
| Reference AF676 | 79,6 |

Fig.3: HEK293 reporter assay

| Antibody ID | HEK reporter assay (IL1b) EC50 [ng/ml] |
|---|---|
| MAB-16-0015 | 27,3 |
| MAB-16-0019 | 2,5 |
| MAB-16-0021 | 33,0 |
| MAB-16-0004 | 67,1 |
| MAB-16-0009 | 18,2 |
| MAB-16-0027 | 37,3 |
| MAB-16-0030 | 8,7 |
| MAB-16-0040 | 9,4 |
| MAB-16-0043 | 27,0 |
| MAB-16-0046 | 6,1 |
| MAB-16-0049 | 42,6 |
| MAB-16-0028 | 5,1 |
| MAB-16-0031 | 23,3 |
| MAB-16-0041 | 0,1 |
| MAB-16-0036 | 9,5 |
| MAB-16-0045 | 90,2 |
| MAB-16-0048 | 16,3 |
| Reference AF676 | 234 |

Fig. 4: NFkB luciferase reporter assay using an A549 stable cell line

| Antibody ID | Signosis NFkB A549 (IL-1b) EC50 [ng/ml] |
|---|---|
| MAB-16-0015 | + |
| MAB-16-0019 | ++ |
| MAB-16-0021 | + |
| MAB-16-0004 | ++ |
| MAB-16-0009 | +++ |
| MAB-16-0027 | ++ |
| MAB-16-0030 | +++ |
| MAB-16-0040 | + |
| MAB-16-0043 | + |
| MAB-16-0046 | +++ |
| MAB-16-0049 | + |
| MAB-16-0028 | +++ |
| MAB-16-0031 | + |
| MAB-16-0041 | + |
| MAB-16-0036 | +++ |
| MAB-16-0045 | + |
| MAB-16-0048 | + |
| Reference AF676 | + |

Fig. 5: Cell binding analysis: Binding to IL-1R3 expressing cells

| | NIH-3T3 | A549 | HEK-293 | SK-MEL-30 |
|---|---|---|---|---|
| Antibody | MFI – fold over isotype control | | | |
| MAB-16-0019 | 1,2 | 2,7 | 3,6 | 79,0 |
| MAB-16-0030 | 0,9 | 2,4 | 2,8 | 69,7 |
| MAB-16-0040 | 1,0 | 2,6 | 3,0 | 73,7 |
| MAB-16-0036 | 1,1 | 2,0 | 3,0 | 70,6 |
| MAB-16-0149 | 1,1 | 2,4 | 3,4 | 77,7 |
| MAB-16-0150 | 1,1 | 3,2 | 4,8 | 87,1 |

Fig. 6: Cell binding analysis: Cell binding on human-IL-1R3 high expressing cell line SK-MEL-30

| Antibody | EC50 (ng/mL) |
|---|---|
| MAB-16-0030 | 307 |
| MAB-16-0149 | 306 |

Fig. 7: Human-IL-1R3 biochemical ELISA

| Antibody | EC50 (ng/mL) |
|---|---|
| MAB-16-0149 | 16,3 |
| MAB-16-0150 | 29,1 |

Fig. 8: Inhibition of human IL-1a and IL-1b mediated NfKB signaling in A549-NFkB-RE-Luc cells

| Antibody | Stimulated with hIL-1a EC50 (ng/mL) | Stimulated with hIL-1b EC50 (ng/mL) |
|---|---|---|
| MAB-16-0019 | 56 | 140 |
| MAB-16-0030 | 156 | 149 |
| MAB-16-0040 | 969 | 636 |
| MAB-16-0036 | 199 | 25 |
| MAB-16-0149 | 167 | 109 |
| MAB-16-0150 | 211 | 11 |
| AF676 | 3134 | 919 |

Fig. 9: IL-1α and IL-1β functional neutralization assay - Inhibition of human IL-1a and IL-1b mediated IL-6 release by A-549 cells

| Antibody | Stimulated with hIL-1a EC50 (ng/mL) | Stimulated with hIL-1b EC50 (ng/mL) |
|---|---|---|
| MAB-16-0019 | 546 | 180 |
| MAB-16-0030 | 361 | 346 |
| MAB-16-0040 | 2246 | 234 |
| MAB-16-0036 | 378 | 253 |
| MAB-16-0149 | 266 | 108 |
| MAB-16-0150 | 1464 | 313 |
| AF676 | >10000 | >10000 |

Fig. 10: IL-33 functional neutralization assay - Inhibition of human IL-33 mediated NfkB-signaling in HEK-Blue-IL33™ cells

|  | Stimulated with hIL33 |
| --- | --- |
| Antibody | EC50 (ng/mL) |
| MAB-16-0019 | 376 |
| MAB-16-0030 | 909 |
| MAB-16-0040 | 17195 |
| MAB-16-0036 | 426 |
| MAB-16-0149 | 432 |
| MAB-16-0150 | 2115 |
| AF676 | 26114 |

Fig. 11: IL-36 functional neutralization assay - Inhibition of human IL-36 mediated NfkB-signaling in HEK-293/17-IF cells

|  | Stimulated with hIL36 |
| --- | --- |
| Antibody | EC50 (ng/mL) |
| MAB-16-0019 | 11 |
| MAB-16-0030 | 13 |
| MAB-16-0040 | 42 |
| MAB-16-0036 | 14 |
| MAB-16-0149 | 18 |
| MAB-16-0150 | 13 |
| AF676 | 502 |

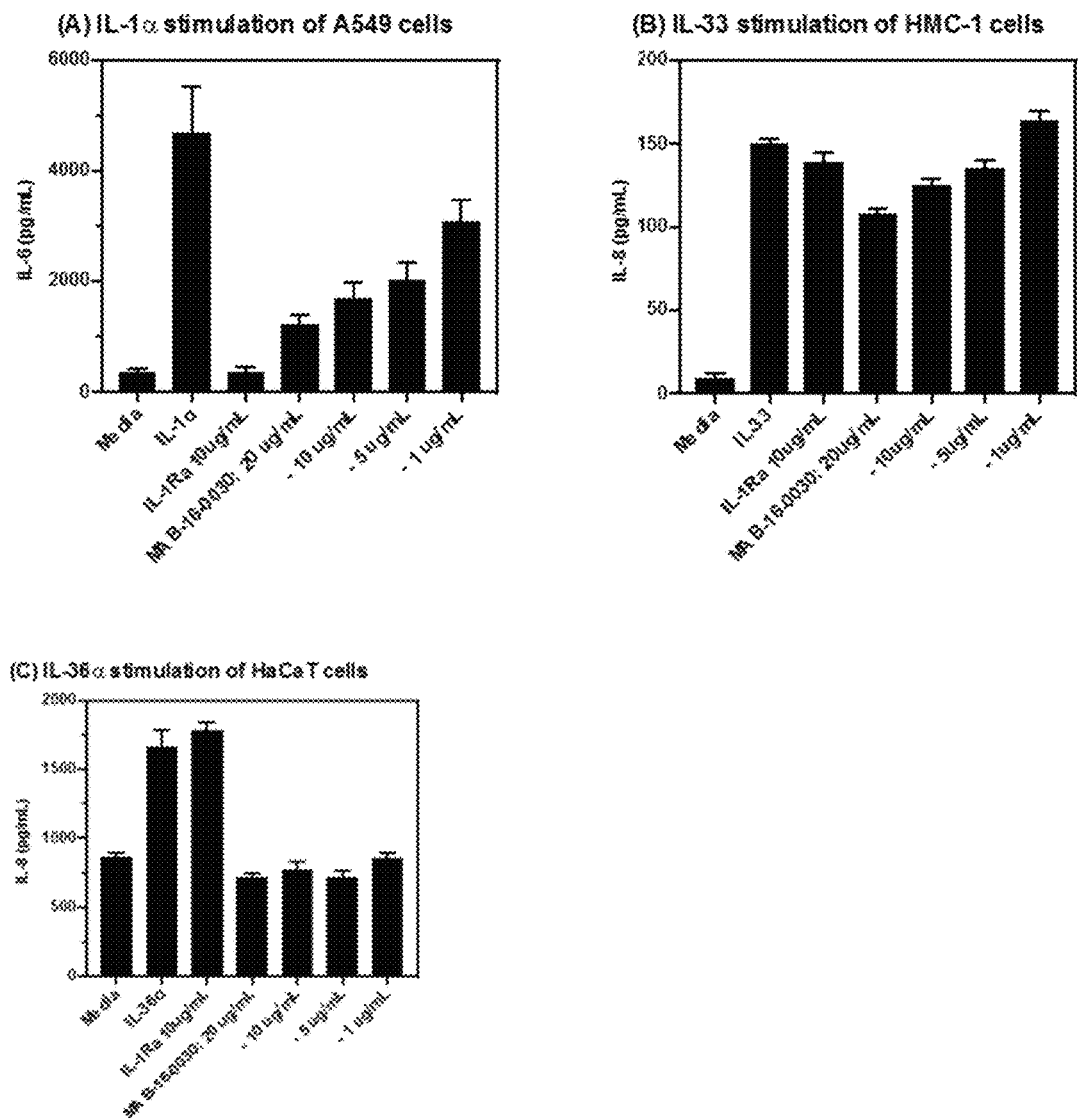
Fig. 12: Neutralization of IL-1a, IL-33 and IL-36a - Neutralization of IL-1a, IL-33 and IL-36a mediated cellular cytokine release by IL-1Ra and MAB-16-0030

Fig. 13: Viability and IL-6 release of unstimulated PBMC treated with humanized anti-IL-1R3 IgG1-LALA antibody MAB-16-0030
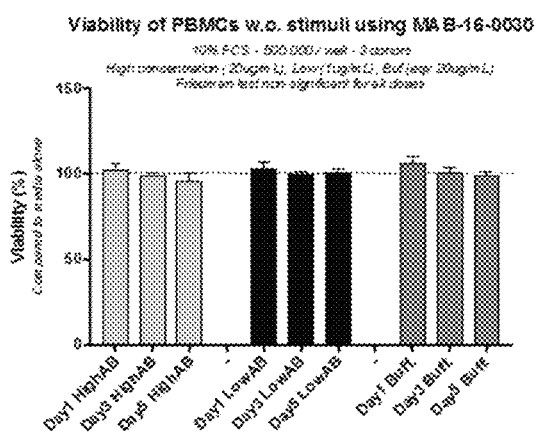
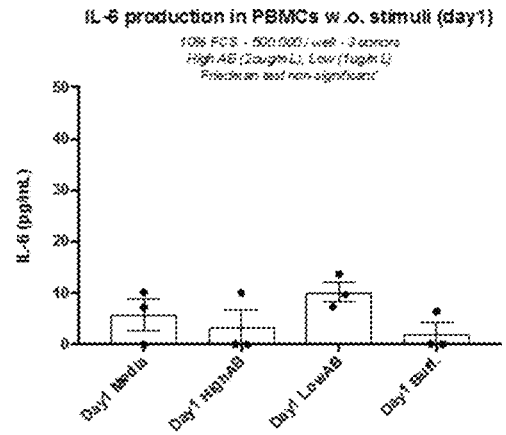
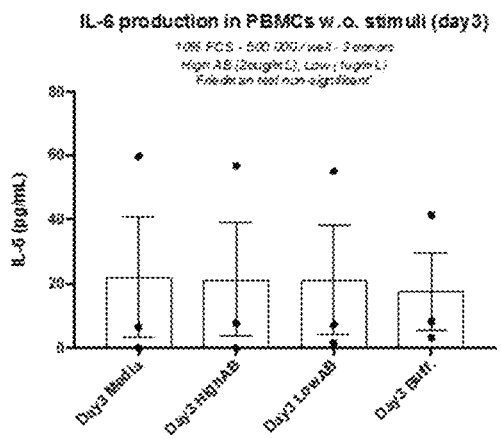
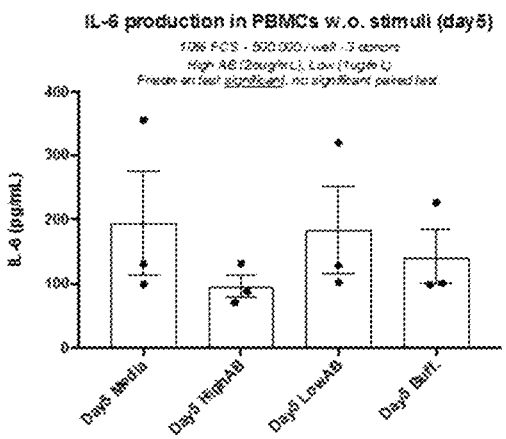

Fig. 14: Functional blockage of PBMCs activated with different stimuli
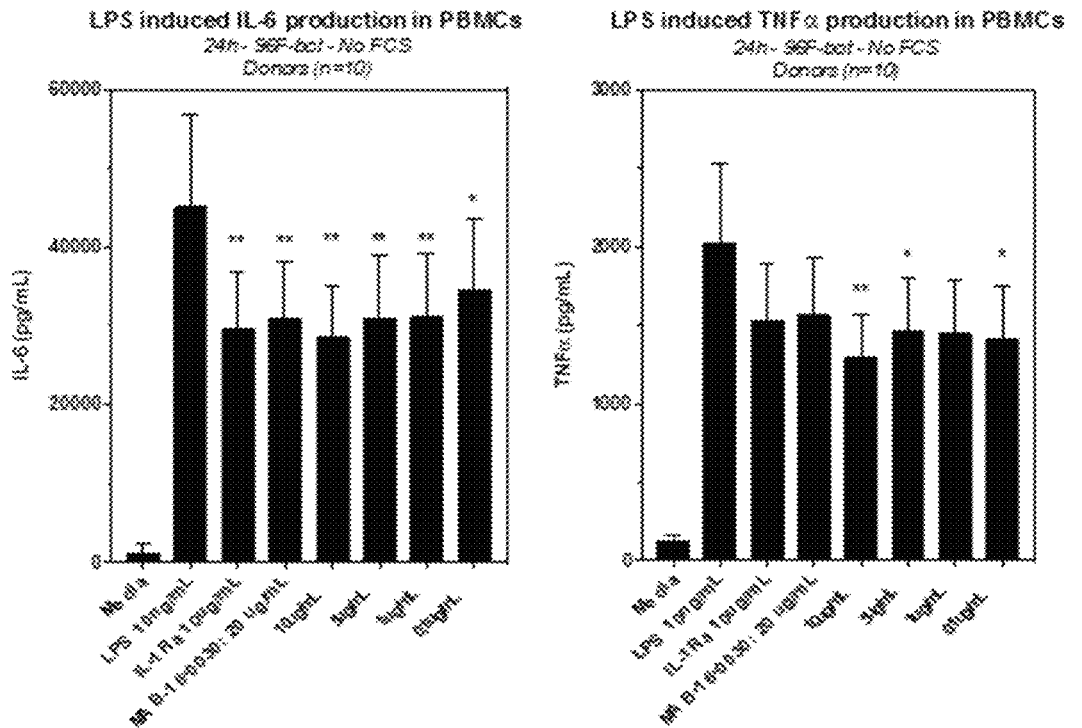
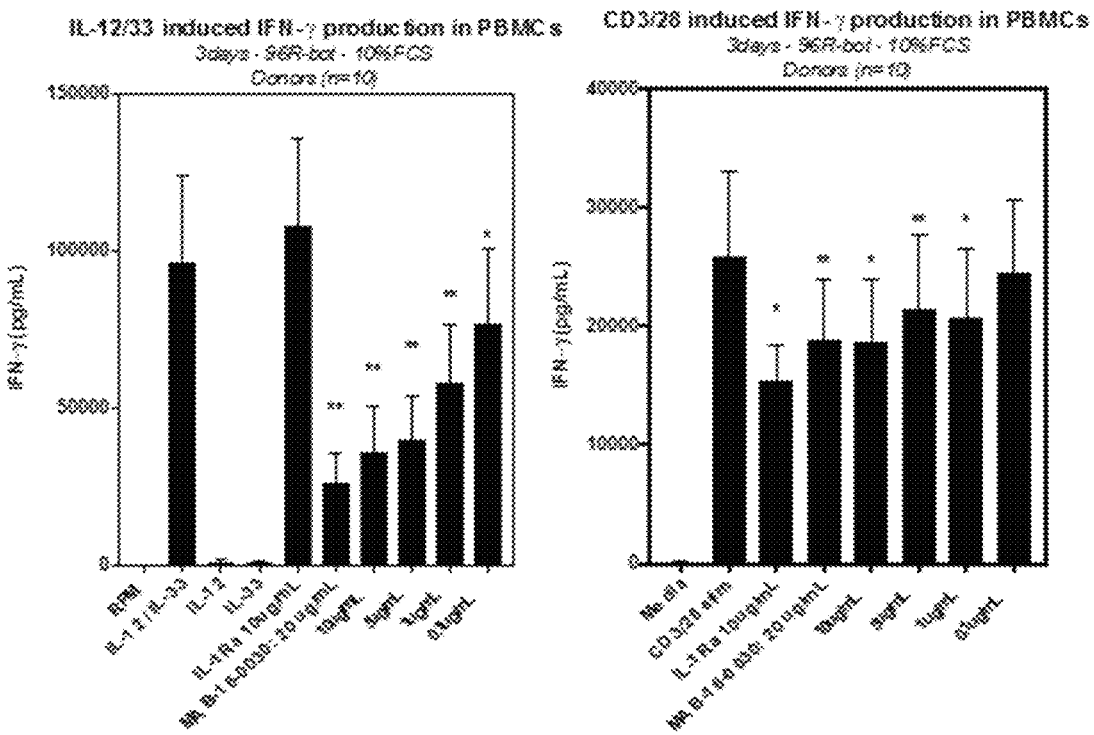

Fig. 15: Functional blockage of immune cells in whole blood activated with *Candida albicans*
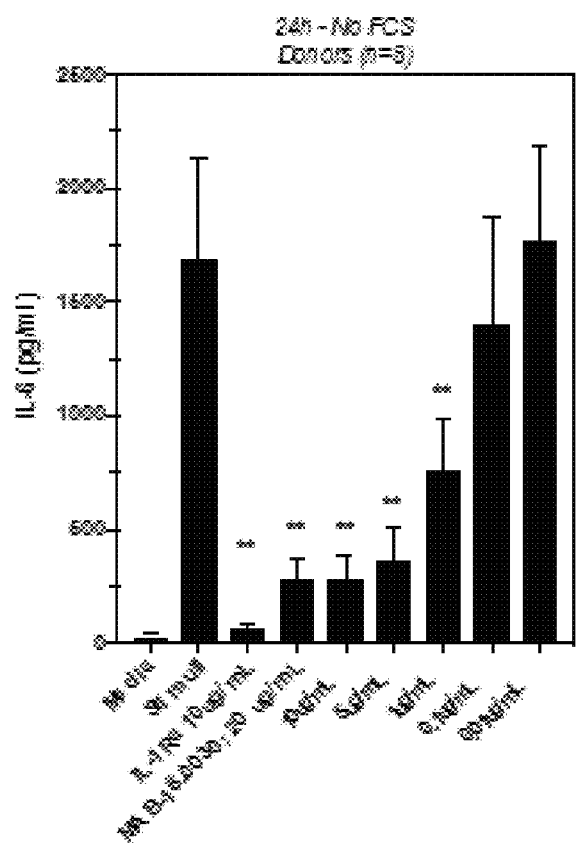

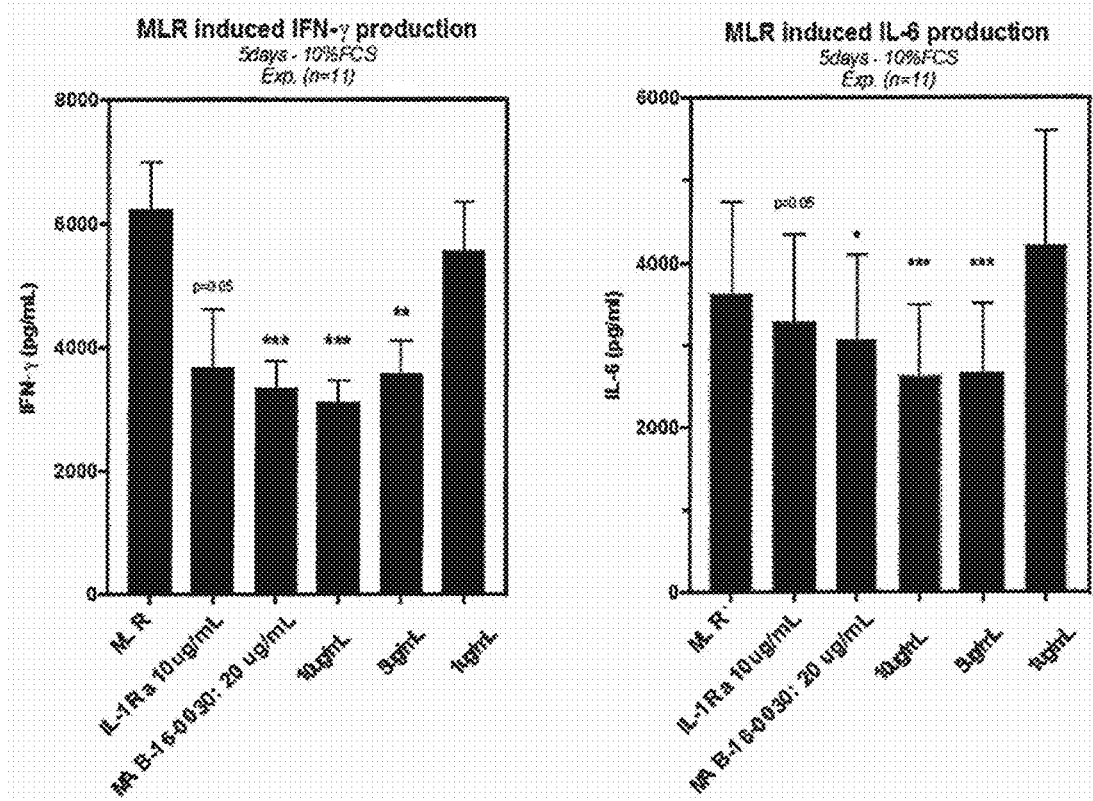

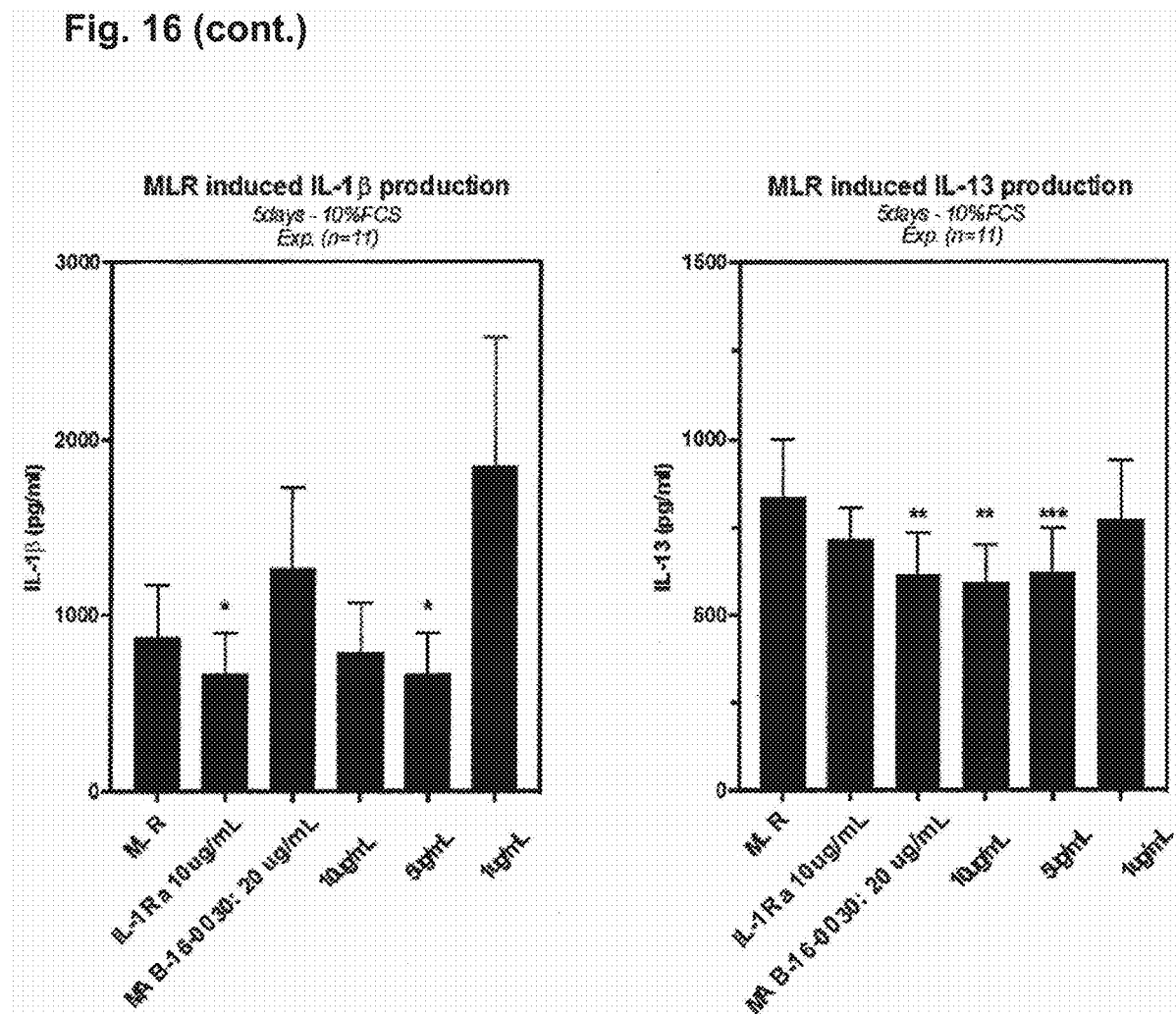

SEQUENCE LISTING

<160> NUMBER OF SEQ ID NOS: 175

<210> SEQ ID NO 1
<211> LENGTH: 118
<212> TYPE: PRT
<213> ORGANISM: Artificial Sequence
<220> FEATURE:
<223> OTHER INFORMATION: humanized antibody

<400> SEQUENCE: 1

Glu Val Gln Leu Glu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Ser
            20                  25                  30

Tyr Trp Ile Cys Trp Val Arg Gln Ala Pro Gly Lys Gly Leu Glu Trp
        35                  40                  45

Val Ser Cys Ile Tyr Thr Gly Ser Gly Gly Thr Tyr Tyr Ala Ser Trp
    50                  55                  60

Glu Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Phe
                85                  90                  95

Cys Ala Arg Asp Pro Gly Tyr Ser Ser Trp Leu Trp Gly Gln Gly Thr
            100                 105                 110

Leu Val Thr Val Ser Ser
        115

<210> SEQ ID NO 2
<211> LENGTH: 122
<212> TYPE: PRT
<213> ORGANISM: Artificial Sequence
<220> FEATURE:
<223> OTHER INFORMATION: humanized antibody

<400> SEQUENCE: 2

Glu Val Gln Leu Glu Glu Ser Gly Gly Asp Leu Val Gln Pro Gly Gly
1               5                   10                  15

Ser Leu Arg Leu Ser Cys Ala Ala Ser Gly Phe Ser Phe Ser Ser Ser
            20                  25                  30

His Tyr Met Cys Trp Val Arg Gln Ala Pro Gly Lys Gly Leu Glu Trp
        35                  40                  45

Val Ser Cys Ile Tyr Ala Gly Ser Ser Gly Asn Thr Tyr Tyr Ala Asn
    50                  55                  60

Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Phe Cys Ala Arg Val Asp Ala Ser Ser Ser Gly Ser Trp Asp Leu Trp
            100                 105                 110

Gly Gln Gly Thr Leu Val Thr Val Ser Ser
        115                 120

<210> SEQ ID NO 3
<211> LENGTH: 123
<212> TYPE: PRT
<213> ORGANISM: Artificial Sequence
<220> FEATURE:
<223> OTHER INFORMATION: humanized antibody

<400> SEQUENCE: 3

```
Glu Val Gln Leu Glu Glu Ser Gly Gly Arg Leu Val Gln Pro Gly Gly
1               5                   10                  15

Ser Leu Arg Leu Ser Cys Ala Val Ser Gly Ile Asp Leu Ser Ser Tyr
            20                  25                  30

Ala Met Gly Trp Val Arg Gln Ala Pro Gly Lys Gly Leu Glu Tyr Val
        35                  40                  45

Ser Val Ile Thr Ser Ser Ala Thr Thr Tyr Tyr Ala Ser Trp Ala Lys
    50                  55                  60

Gly Arg Phe Thr Ile Ser Arg Asp Asn Ser Lys Asn Thr Leu Tyr Leu
65              70                  75                  80

Gln Met Asn Ser Leu Arg Ala Glu Asp Thr Ala Val Tyr Phe Cys Ala
                85                  90                  95

Arg Gly Gly Pro Gly Tyr Ser Thr Asn Thr His Tyr Ala Phe Asp Pro
            100                 105                 110

Trp Gly Gln Gly Thr Leu Val Thr Val Ser Ser
            115                 120
```

<210> SEQ ID NO 4
<211> LENGTH: 119
<212> TYPE: PRT
<213> ORGANISM: Artificial Sequence
<220> FEATURE:
<223> OTHER INFORMATION: humanized antibody

<400> SEQUENCE: 4

```
Glu Val Gln Leu Glu Glu Ser Gly Gly Arg Val Val Gln Pro Gly Arg
1               5                   10                  15

Ser Leu Arg Leu Ser Cys Ala Val Ser Gly Ile Asp Leu Asp Asn Tyr
            20                  25                  30

Ala Met Gly Trp Val Arg Gln Ala Pro Gly Lys Gly Leu Glu Tyr Val
        35                  40                  45

Ala Val Ile Ser Ser Asp Gly Phe Phe Tyr Asp Ala Ser Trp Ala Lys
    50                  55                  60

Gly Arg Phe Thr Ile Ser Arg Asp Asn Ser Lys Asn Thr Leu Tyr Leu
65              70                  75                  80

Gln Met Asn Ser Leu Arg Ala Glu Asp Thr Ala Val Tyr Phe Cys Ala
                85                  90                  95

Arg Asp Arg Gly Thr Ser Thr Gly Ser Leu Asp Leu Trp Gly Gln Gly
            100                 105                 110

Thr Leu Val Thr Val Ser Ser
        115
```

<210> SEQ ID NO 5
<211> LENGTH: 125
<212> TYPE: PRT
<213> ORGANISM: Artificial Sequence
<220> FEATURE:
<223> OTHER INFORMATION: humanized antibody

<400> SEQUENCE: 5

```
Glu Val Gln Leu Glu Glu Ser Gly Gly Arg Leu Val Gln Pro Gly Gly
1               5                   10                  15

Ser Leu Arg Leu Ser Cys Ala Ala Ser Gly Phe Ser Leu Ser Ser Tyr
            20                  25                  30

Tyr Met Ser Trp Val Arg Gln Ala Pro Gly Lys Gly Leu Glu Trp Val
        35                  40                  45

Ser Ile Ile Ser Gly Ser Ala Ser Thr Tyr Tyr Ala Thr Trp Ala Lys
```

```
                    50                  55                  60
Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Phe Cys Ala
                     85                  90                  95

Arg Thr His Tyr Ala Ala Val Ala Gly Tyr Gly Tyr Ala Ser Arg Leu
                100                 105                 110

Asp Leu Trp Gly Gln Gly Thr Leu Val Thr Val Ser Ser
            115                 120                 125
```

<210> SEQ ID NO 6
<211> LENGTH: 120
<212> TYPE: PRT
<213> ORGANISM: Artificial Sequence
<220> FEATURE:
<223> OTHER INFORMATION: humanized antibody

<400> SEQUENCE: 6

```
Glu Val Gln Leu Glu Glu Ser Gly Gly Asp Leu Val Gln Pro Gly Gly
 1               5                  10                  15

Ser Leu Arg Leu Ser Cys Ala Ala Ser Gly Phe Ser Phe Ser Ser Asn
                20                  25                  30

Tyr Trp Ile Cys Trp Val Arg Gln Ala Pro Gly Lys Gly Leu Glu Leu
             35                  40                  45

Val Ser Cys Ile Tyr Thr Ser Thr Gly Asn Thr Trp Tyr Ala Ser Trp
         50                  55                  60

Ala Lys Gly Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Phe
                 85                  90                  95

Cys Ala Arg Asp Leu Leu Val Val Thr Ser Phe Asn Leu Trp Gly Gln
                100                 105                 110

Gly Thr Leu Val Thr Val Ser Ser
            115                 120
```

<210> SEQ ID NO 7
<211> LENGTH: 120
<212> TYPE: PRT
<213> ORGANISM: Artificial Sequence
<220> FEATURE:
<223> OTHER INFORMATION: humanized antibody

<400> SEQUENCE: 7

```
Glu Val Gln Leu Glu Glu Ser Gly Gly Asp Leu Val Gln Pro Gly Gly
 1               5                  10                  15

Ser Leu Arg Leu Ser Cys Ala Ala Ser Gly Phe Ser Phe Ser Ser Ser
                20                  25                  30

Tyr Tyr Met Cys Trp Val Arg Gln Ala Pro Gly Lys Gly Leu Glu Trp
             35                  40                  45

Val Ser Cys Ile Tyr Ala Gly Ser Ser Gly Val Thr Tyr Tyr Ala Ser
         50                  55                  60

Trp Ala Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Phe Cys Ala Ser Glu Thr Asp Gly Asn Tyr Phe Asn Leu Trp Gly Gln
                100                 105                 110
```

```
Gly Thr Leu Val Thr Val Ser Ser
        115                 120

<210> SEQ ID NO 8
<211> LENGTH: 120
<212> TYPE: PRT
<213> ORGANISM: Artificial Sequence
<220> FEATURE:
<223> OTHER INFORMATION: humanized antibody

<400> SEQUENCE: 8

Glu Val Gln Leu Glu Gln Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Tyr Trp Arg Cys Trp Val Arg Gln Ala Pro Gly Lys Gly Leu Glu Trp
        35                  40                  45

Val Ser Cys Ile Tyr Ala Gly Ser Gly Asp Val Thr Tyr Tyr Ala Asn
    50                  55                  60

Trp Val Asn Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Ser Gly Val Gly Phe Gly Tyr Phe Asn Leu Trp Gly Gln
            100                 105                 110

Gly Thr Leu Val Thr Val Ser Ser
        115                 120

<210> SEQ ID NO 9
<211> LENGTH: 122
<212> TYPE: PRT
<213> ORGANISM: Artificial Sequence
<220> FEATURE:
<223> OTHER INFORMATION: humanized antibody

<400> SEQUENCE: 9

Glu Val Gln Leu Glu Glu Ser Gly Gly Gly Leu Val Gln Pro Gly Gly
1               5                   10                  15

Ser Leu Arg Leu Ser Cys Ala Ala Ser Gly Ile Asp Phe Ser Ser Tyr
            20                  25                  30

Tyr Tyr Met Cys Trp Val Arg Gln Ala Pro Gly Lys Gly Leu Glu Trp
        35                  40                  45

Val Ser Cys Ile Phe Ile Gly Tyr Gly Asp Val Thr Trp Tyr Ala Ser
    50                  55                  60

Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Phe Cys Ala Arg Ala Leu Gly Ser Ser Gly Tyr Arg Val Asn Leu Trp
            100                 105                 110

Gly Gln Gly Thr Leu Val Thr Val Ser Ser
        115                 120

<210> SEQ ID NO 10
<211> LENGTH: 115
<212> TYPE: PRT
<213> ORGANISM: Artificial Sequence
<220> FEATURE:
<223> OTHER INFORMATION: humanized antibody
```

<400> SEQUENCE: 10

Glu Val Gln Leu Glu Glu Ser Gly Gly Arg Leu Val Gln Pro Gly Gly
1               5                   10                  15

Ser Leu Arg Leu Ser Cys Ala Ala Ser Gly Phe Ser Leu Ser Ser Tyr
            20                  25                  30

Trp Met Ser Trp Val Arg Gln Ala Pro Gly Lys Gly Leu Glu Trp Val
        35                  40                  45

Ser Met Ile Tyr Gly Ser Gly Tyr Thr Tyr Tyr Ala Ser Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Arg Asp Pro Gln Tyr Phe Ile Leu Trp Gly Gln Gly Thr Leu Val Thr
            100                 105                 110

Val Ser Ser
        115

<210> SEQ ID NO 11
<211> LENGTH: 120
<212> TYPE: PRT
<213> ORGANISM: Artificial Sequence
<220> FEATURE:
<223> OTHER INFORMATION: humanized antibody

<400> SEQUENCE: 11

Glu Val Gln Leu Glu Glu Ser Gly Gly Arg Leu Val Gln Pro Gly Gly
1               5                   10                  15

Ser Leu Arg Leu Ser Cys Ala Val Ser Gly Phe Ser Leu Ser Ser Tyr
            20                  25                  30

Asp Met Ser Trp Val Arg Gln Ala Pro Gly Lys Gly Leu Glu Trp Val
        35                  40                  45

Ser Thr Ile Tyr Ile Gly Gly Thr Thr Ala Tyr Ala Ser Trp Pro Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Arg Leu Gln Gly Ala Asn Tyr Tyr Asn Ser Leu Ala Leu Trp Gly Gln
            100                 105                 110

Gly Thr Leu Val Thr Val Ser Ser
        115                 120

<210> SEQ ID NO 12
<211> LENGTH: 120
<212> TYPE: PRT
<213> ORGANISM: Artificial Sequence
<220> FEATURE:
<223> OTHER INFORMATION: humanized antibody

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Ser Asn
            20                  25                  30

Tyr Tyr Met Cys Trp Val Arg Gln Ala Pro Gly Lys Gly Leu Glu Leu
        35                  40                  45

Val Ser Cys Ile Tyr Thr Asn Ser Gly Asn Thr Trp Ser Ala Ser Trp
            50                  55                  60

Ala Lys Gly Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Phe
                    85                  90                  95

Cys Ala Arg Asp Leu Asn Tyr Pro Asp Thr Ser Asn Leu Trp Gly Gln
                100                 105                 110

Gly Thr Leu Val Thr Val Ser Ser
            115                 120

<210> SEQ ID NO 13
<211> LENGTH: 119
<212> TYPE: PRT
<213> ORGANISM: Artificial Sequence
<220> FEATURE:
<223> OTHER INFORMATION: humanized antibody

<400> SEQUENCE: 13

Glu Val Gln Leu Glu Glu Ser Gly Gly Asp Leu Val Gln Pro Gly Gly
 1               5                  10                  15

Ser Leu Arg Leu Ser Cys Ala Ala Ser Gly Phe Ser Phe Ser Phe Gly
                20                  25                  30

Tyr Tyr Met Cys Trp Val Arg Gln Ala Pro Gly Lys Gly Leu Glu Trp
                35                  40                  45

Val Ser Cys Ile Tyr Gly Asp Ser Ser Asp Thr Leu Tyr Ala Asn Trp
            50                  55                  60

Ala Lys Gly Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Phe
                    85                  90                  95

Cys Ala Arg Tyr Pro Gly Gly Ser Tyr Tyr Asn Leu Trp Gly Gln Gly
                100                 105                 110

Thr Leu Val Thr Val Ser Ser
            115

<210> SEQ ID NO 14
<211> LENGTH: 122
<212> TYPE: PRT
<213> ORGANISM: Artificial Sequence
<220> FEATURE:
<223> OTHER INFORMATION: humanized antibody

<400> SEQUENCE: 14

Glu Val Gln Leu Glu Glu Ser Gly Gly Asp Leu Val Gln Pro Gly Gly
 1               5                  10                  15

Ser Leu Arg Leu Ser Cys Ala Ala Ser Gly Phe Ser Phe Ser Ser Thr
                20                  25                  30

Tyr Tyr Met Cys Trp Val Arg Gln Ala Pro Gly Lys Gly Leu Glu Trp
                35                  40                  45

Val Ser Cys Ile Tyr Ala Gly Ser Ser Gly Ser Thr Tyr Tyr Ala Ser
            50                  55                  60

Trp Ala Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                    85                  90                  95

Phe Cys Ala Arg Val Asp Gly Ser Ser Gly Ser Trp Ser Asp Leu Trp
                100                 105                 110

Gly Gln Gly Thr Leu Val Thr Val Ser Ser
        115                 120

<210> SEQ ID NO 15
<211> LENGTH: 122
<212> TYPE: PRT
<213> ORGANISM: Artificial Sequence
<220> FEATURE:
<223> OTHER INFORMATION: humanized antibody

<400> SEQUENCE: 15

Glu Val Gln Leu Glu Glu Ser Gly Gly Asp Leu Val Gln Pro Gly Gly
1               5                   10                  15

Ser Leu Arg Leu Ser Cys Ala Ala Ser Gly Ile Ser Phe Ser Ser Ser
            20                  25                  30

Asp Phe Met Cys Trp Val Arg Gln Ala Pro Gly Lys Gly Leu Glu Trp
        35                  40                  45

Val Ser Cys Ile Tyr Ala Gly Ser Ser Val Ser Ile Tyr Tyr Ala Thr
    50                  55                  60

Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Phe Cys Ala Arg Ser Thr Gly Ser Val Gly Arg Gly Phe Asn Leu Trp
            100                 105                 110

Gly Gln Gly Thr Leu Val Thr Val Ser Ser
        115                 120

<210> SEQ ID NO 16
<211> LENGTH: 121
<212> TYPE: PRT
<213> ORGANISM: Artificial Sequence
<220> FEATURE:
<223> OTHER INFORMATION: humanized antibody

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Ile
            20                  25                  30

Tyr Tyr Met Cys Trp Val Arg Gln Ala Pro Gly Lys Gly Leu Glu Trp
        35                  40                  45

Val Ser Cys Ile Tyr Thr Gly Asn Ser Asp Phe Thr Tyr Tyr Ala Asn
    50                  55                  60

Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Phe Cys Ala Arg Phe Arg Asp Asp Tyr Ala Ser Leu Lys Leu Trp Gly
            100                 105                 110

Gln Gly Thr Leu Val Thr Val Ser Ser
        115                 120

<210> SEQ ID NO 17
<211> LENGTH: 120
<212> TYPE: PRT
<213> ORGANISM: Artificial Sequence
<220> FEATURE:
<223> OTHER INFORMATION: humanized antibody

<400> SEQUENCE: 17

Glu Val Gln Leu Glu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Gly
            20                  25                  30

Tyr Asp Met Cys Trp Val Arg Gln Ala Pro Gly Lys Gly Leu Glu Trp
        35                  40                  45

Val Ser Cys Ile Tyr Thr Gly Ser Gly Ser Thr Tyr Tyr Ala Asn Trp
50                  55                  60

Ala Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Phe
                85                  90                  95

Cys Ala Arg Asn Ser Asn Asp Trp Met Tyr Phe Asn Leu Trp Gly Gln
            100                 105                 110

Gly Thr Leu Val Thr Val Ser Ser
            115                 120

<210> SEQ ID NO 18
<211> LENGTH: 117
<212> TYPE: PRT
<213> ORGANISM: Artificial Sequence
<220> FEATURE:
<223> OTHER INFORMATION: humanized antibody

<400> SEQUENCE: 18

Glu Val Gln Leu Glu Gln Ser Gly Gly Gly Leu Val Gln Pro Gly Gly
1               5                   10                  15

Ser Leu Arg Leu Ser Cys Ala Ala Ser Gly Phe Ser Phe Ser Ser Ser
            20                  25                  30

Tyr Trp Ile Cys Trp Val Arg Gln Ala Pro Gly Lys Gly Leu Glu Trp
        35                  40                  45

Val Ala Cys Ile Tyr Thr Gly Ser Gly Gly Thr Tyr Tyr Ala Ser Trp
50                  55                  60

Glu Lys Gly Arg Phe Thr Ile Ser Lys Thr Ser Ser Thr Thr Leu Tyr
65                  70                  75                  80

Leu Gln Met Asn Ser Leu Arg Ala Glu Asp Thr Ala Val Tyr Phe Cys
                85                  90                  95

Ala Arg Asp Pro Gly Tyr Ser Ser Trp Leu Trp Gly Gln Gly Thr Leu
            100                 105                 110

Val Thr Val Ser Ser
        115

<210> SEQ ID NO 19
<211> LENGTH: 122
<212> TYPE: PRT
<213> ORGANISM: Artificial Sequence
<220> FEATURE:
<223> OTHER INFORMATION: humanized antibody

<400> SEQUENCE: 19

Glu Val Gln Leu Glu Glu Ser Gly Gly Asp Leu Val Gln Pro Gly Ala
1               5                   10                  15

Ser Leu Arg Leu Ser Cys Ala Ala Ser Gly Phe Ser Phe Ser Ser Ser
            20                  25                  30

His Tyr Met Cys Trp Val Arg Gln Ala Pro Gly Lys Gly Leu Glu Trp
        35                  40                  45

```
Val Ala Cys Ile Tyr Ala Gly Ser Ser Gly Asn Thr Tyr Tyr Ala Asn
        50                  55                  60

Trp Ala Lys Gly Arg Phe Thr Ile Ser Lys Thr Asn Ser Lys Asn Thr
 65                  70                  75                  80

Leu Tyr Leu Gln Met Asn Ser Leu Arg Ala Glu Asp Thr Ala Val Tyr
                     85                  90                  95

Phe Cys Ala Arg Val Asp Ala Ser Ser Gly Ser Trp Asp Leu Trp
                100                 105                 110

Gly Gln Gly Thr Leu Val Thr Val Ser Ser
            115                 120
```

<210> SEQ ID NO 20
<211> LENGTH: 122
<212> TYPE: PRT
<213> ORGANISM: Artificial Sequence
<220> FEATURE:
<223> OTHER INFORMATION: humanized antibody

<400> SEQUENCE: 20

```
Glu Val Gln Leu Leu Glu Ser Gly Gly Arg Leu Val Gln Pro Gly Thr
 1                   5                  10                  15

Ser Leu Arg Leu Ser Cys Ala Val Ser Gly Ile Asp Leu Ser Ser Tyr
                    20                  25                  30

Ala Met Gly Trp Val Arg Gln Ala Pro Gly Lys Gly Leu Glu Tyr Val
                35                  40                  45

Gly Val Ile Thr Ser Ser Ala Thr Thr Tyr Tyr Ala Ser Trp Ala Lys
        50                  55                  60

Gly Arg Phe Thr Ile Ser Lys Thr Ser Thr Thr Leu Tyr Leu Gln
 65                  70                  75                  80

Met Asn Ser Leu Arg Ala Glu Asp Thr Ala Val Tyr Phe Cys Ala Arg
                     85                  90                  95

Gly Gly Pro Gly Tyr Ser Thr Asn Thr His Tyr Ala Phe Asp Pro Trp
                100                 105                 110

Gly Gln Gly Thr Leu Val Thr Val Ser Ser
            115                 120
```

<210> SEQ ID NO 21
<211> LENGTH: 119
<212> TYPE: PRT
<213> ORGANISM: Artificial Sequence
<220> FEATURE:
<223> OTHER INFORMATION: humanized antibody

<400> SEQUENCE: 21

```
Glu Val Gln Leu Glu Glu Ser Gly Gly Arg Val Val Gln Pro Gly Thr
 1                   5                  10                  15

Ser Leu Arg Leu Ser Cys Ala Val Ser Gly Ile Asp Leu Asp Asn Tyr
                    20                  25                  30

Ala Met Gly Trp Val Arg Gln Ala Pro Gly Lys Gly Leu Glu Tyr Val
                35                  40                  45

Ala Val Ile Ser Ser Asp Gly Phe Phe Tyr Asp Ala Ser Trp Ala Lys
        50                  55                  60

Gly Arg Phe Thr Ile Ser Lys Ala Asn Ser Lys Asn Thr Leu Tyr Leu
 65                  70                  75                  80

Gln Met Asn Ser Leu Arg Ala Glu Asp Thr Ala Val Tyr Phe Cys Ala
                     85                  90                  95

Arg Asp Arg Gly Thr Ser Thr Gly Ser Leu Asp Leu Trp Gly Gln Gly
```

Thr Leu Val Thr Val Ser Ser
        115

<210> SEQ ID NO 22
<211> LENGTH: 123
<212> TYPE: PRT
<213> ORGANISM: Artificial Sequence
<220> FEATURE:
<223> OTHER INFORMATION: humanized antibody

<400> SEQUENCE: 22

Gln Val Gln Leu Glu Glu Ser Gly Gly Arg Leu Val Gln Pro Gly Thr
1               5                   10                  15

Ser Leu Arg Leu Ser Cys Ala Ala Ser Gly Phe Ser Leu Ser Ser Tyr
            20                  25                  30

Tyr Met Ser Trp Val Arg Gln Ala Pro Gly Lys Gly Leu Glu Trp Val
        35                  40                  45

Ala Ile Ile Ser Gly Ser Ala Ser Thr Tyr Tyr Ala Thr Trp Ala Lys
    50                  55                  60

Gly Arg Phe Thr Ile Ser Lys Thr Ser Thr Thr Leu Tyr Leu Gln Met
65                  70                  75                  80

Asn Ser Leu Arg Ala Glu Asp Thr Ala Val Tyr Phe Cys Ala Arg Thr
                85                  90                  95

His Tyr Ala Ala Val Ala Gly Tyr Gly Tyr Ala Ser Arg Leu Asp Leu
            100                 105                 110

Trp Gly Gln Gly Thr Leu Val Thr Val Ser Ser
        115                 120

<210> SEQ ID NO 23
<211> LENGTH: 120
<212> TYPE: PRT
<213> ORGANISM: Artificial Sequence
<220> FEATURE:
<223> OTHER INFORMATION: humanized antibody

<400> SEQUENCE: 23

Gln Val Gln Leu Gln Glu Ser Gly Gly Asp Leu Val Gln Pro Gly Gly
1               5                   10                  15

Ser Leu Arg Leu Ser Cys Ala Ala Ser Gly Phe Ser Phe Ser Ser Asn
            20                  25                  30

Tyr Trp Ile Cys Trp Val Arg Gln Ala Pro Gly Lys Gly Leu Glu Leu
        35                  40                  45

Val Ala Cys Ile Tyr Thr Thr Ser Thr Gly Asn Thr Trp Tyr Ala Ser Trp
    50                  55                  60

Ala Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Phe
                85                  90                  95

Cys Ala Arg Asp Leu Leu Val Val Thr Ser Phe Asn Leu Trp Gly Gln
            100                 105                 110

Gly Thr Leu Val Thr Val Ser Ser
        115                 120

<210> SEQ ID NO 24
<211> LENGTH: 119
<212> TYPE: PRT
<213> ORGANISM: Artificial Sequence
<220> FEATURE:

<223> OTHER INFORMATION: humanized antibody

<400> SEQUENCE: 24

Glu Val Gln Leu Val Glu Ser Gly Gly Asp Leu Val Gln Pro Gly Ala
1               5                   10                  15

Ser Leu Arg Leu Ser Cys Ala Ala Ser Gly Phe Ser Phe Ser Ser Ser
            20                  25                  30

Tyr Tyr Met Cys Trp Val Arg Gln Ala Pro Gly Lys Gly Leu Glu Trp
        35                  40                  45

Val Ala Cys Ile Tyr Ala Gly Ser Ser Gly Val Thr Tyr Tyr Ala Ser
    50                  55                  60

Trp Ala Lys Gly Arg Phe Thr Ile Ser Asp Thr Ser Ser Thr Thr Leu
65                  70                  75                  80

Tyr Leu Gln Met Asn Ser Leu Arg Ala Glu Asp Thr Ala Val Tyr Phe
                85                  90                  95

Cys Ala Ser Glu Thr Asp Gly Asn Tyr Phe Asn Leu Trp Gly Gln Gly
            100                 105                 110

Thr Leu Val Thr Val Ser Ser
        115

<210> SEQ ID NO 25
<211> LENGTH: 120
<212> TYPE: PRT
<213> ORGANISM: Artificial Sequence
<220> FEATURE:
<223> OTHER INFORMATION: humanized antibody

<400> SEQUENCE: 25

Glu Val Gln Leu Glu Gln Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Tyr Trp Arg Cys Trp Val Arg Gln Ala Pro Gly Lys Gly Leu Glu Trp
        35                  40                  45

Val Ala Cys Ile Tyr Ala Gly Ser Gly Asp Val Thr Tyr Tyr Ala Asn
    50                  55                  60

Trp Val Asn Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Val Tyr
                85                  90                  95

Tyr Cys Ala Ser Gly Val Gly Phe Gly Tyr Phe Asn Leu Trp Gly Gln
            100                 105                 110

Gly Thr Leu Val Thr Val Ser Ser
        115                 120

<210> SEQ ID NO 26
<211> LENGTH: 122
<212> TYPE: PRT
<213> ORGANISM: Artificial Sequence
<220> FEATURE:
<223> OTHER INFORMATION: humanized antibody

<400> SEQUENCE: 26

Glu Val Gln Leu Glu Ser Gly Gly Gly Leu Val Gln Pro Gly Gly
1               5                   10                  15

Ser Leu Arg Leu Ser Cys Ala Ala Ser Gly Ile Asp Phe Ser Ser Tyr
            20                  25                  30

Tyr Tyr Met Cys Trp Val Arg Gln Ala Pro Gly Lys Gly Leu Glu Trp

```
                35                  40                  45
Val Ala Cys Ile Phe Ile Gly Tyr Gly Asp Val Thr Trp Tyr Ala Ser
            50                  55                  60

Trp Ala Lys Gly Arg Phe Thr Ile Ser Lys Ala Asn Ser Lys Asn Thr
 65                  70                  75                  80

Leu Tyr Leu Gln Met Asn Ser Leu Arg Ala Glu Asp Thr Ala Val Tyr
                85                  90                  95

Phe Cys Ala Arg Ala Leu Gly Ser Ser Gly Tyr Arg Val Asn Leu Trp
                100                 105                 110

Gly Gln Gly Thr Leu Val Thr Val Ser Ser
                115                 120
```

<210> SEQ ID NO 27
<211> LENGTH: 113
<212> TYPE: PRT
<213> ORGANISM: Artificial Sequence
<220> FEATURE:
<223> OTHER INFORMATION: humanized antibody

<400> SEQUENCE: 27

```
Gln Val Gln Leu Glu Glu Ser Gly Gly Arg Leu Val Gln Pro Gly Ala
 1               5                   10                  15

Ser Leu Arg Leu Ser Cys Ala Ala Ser Gly Phe Ser Leu Ser Ser Tyr
                20                  25                  30

Trp Met Ser Trp Val Arg Gln Ala Pro Gly Lys Gly Leu Glu Trp Val
            35                  40                  45

Ala Met Ile Tyr Gly Ser Gly Tyr Thr Tyr Tyr Ala Ser Trp Ala Lys
        50                  55                  60

Gly Arg Phe Thr Ile Ser Thr Thr Ser Thr Thr Leu Tyr Leu Gln Met
 65                  70                  75                  80

Asn Ser Leu Arg Ala Glu Asp Thr Ala Val Tyr Phe Cys Ala Arg Asp
                85                  90                  95

Pro Gln Tyr Phe Ile Leu Trp Gly Gln Gly Thr Leu Val Thr Val Ser
                100                 105                 110

Ser
```

<210> SEQ ID NO 28
<211> LENGTH: 120
<212> TYPE: PRT
<213> ORGANISM: Artificial Sequence
<220> FEATURE:
<223> OTHER INFORMATION: humanized antibody

<400> SEQUENCE: 28

```
Glu Val Gln Leu Glu Glu Ser Gly Gly Arg Leu Val Gln Pro Gly Thr
 1               5                   10                  15

Ser Leu Arg Leu Ser Cys Ala Val Ser Gly Phe Ser Leu Ser Ser Tyr
                20                  25                  30

Asp Met Ser Trp Val Arg Gln Ala Pro Gly Lys Gly Leu Glu Trp Val
            35                  40                  45

Ser Thr Ile Tyr Ile Gly Gly Thr Thr Ala Tyr Ala Ser Trp Pro Lys
        50                  55                  60

Gly Arg Phe Thr Ile Ser Lys Thr Asn Ser Lys Asn Thr Leu Tyr Leu
 65                  70                  75                  80

Gln Met Asn Ser Leu Arg Ala Glu Asp Thr Ala Val Tyr Phe Cys Ala
                85                  90                  95

Arg Leu Gln Gly Ala Asn Tyr Tyr Asn Ser Leu Ala Leu Trp Gly Gln
```

Gly Thr Leu Val Thr Val Ser Ser
        115                 120

<210> SEQ ID NO 29
<211> LENGTH: 119
<212> TYPE: PRT
<213> ORGANISM: Artificial Sequence
<220> FEATURE:
<223> OTHER INFORMATION: humanized antibody

<400> SEQUENCE: 29

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Ser Asn
            20                  25                  30

Tyr Tyr Met Cys Trp Val Arg Gln Ala Pro Gly Lys Gly Leu Glu Leu
        35                  40                  45

Val Ala Cys Ile Tyr Thr Asn Ser Gly Asn Thr Trp Ser Ala Ser Trp
    50                  55                  60

Ala Lys Gly Arg Phe Thr Ile Ser Lys Thr Asn Ser Thr Thr Leu Tyr
65                  70                  75                  80

Leu Gln Met Asn Ser Leu Arg Ala Glu Asp Thr Ala Val Tyr Phe Cys
                85                  90                  95

Ala Arg Asp Leu Asn Tyr Pro Asp Thr Ser Asn Leu Trp Gly Gln Gly
            100                 105                 110

Thr Leu Val Thr Val Ser Ser
        115

<210> SEQ ID NO 30
<211> LENGTH: 119
<212> TYPE: PRT
<213> ORGANISM: Artificial Sequence
<220> FEATURE:
<223> OTHER INFORMATION: humanized antibody

<400> SEQUENCE: 30

Glu Val Gln Leu Glu Glu Ser Gly Gly Asp Leu Val Gln Pro Gly Gly
1               5                   10                  15

Ser Leu Arg Leu Ser Cys Ala Ala Ser Gly Phe Ser Phe Ser Phe Gly
            20                  25                  30

Tyr Tyr Met Cys Trp Val Arg Gln Ala Pro Gly Lys Gly Leu Glu Trp
        35                  40                  45

Val Ala Cys Ile Tyr Gly Asp Ser Ser Asp Thr Leu Tyr Ala Asn Trp
    50                  55                  60

Ala Lys Gly Arg Phe Thr Ile Ser Lys Thr Asn Ser Lys Asn Thr Leu
65                  70                  75                  80

Tyr Leu Gln Met Asn Ser Leu Arg Ala Glu Asp Thr Ala Val Tyr Phe
                85                  90                  95

Cys Ala Arg Tyr Pro Gly Gly Ser Tyr Tyr Asn Leu Trp Gly Gln Gly
            100                 105                 110

Thr Leu Val Thr Val Ser Ser
        115

<210> SEQ ID NO 31
<211> LENGTH: 120
<212> TYPE: PRT
<213> ORGANISM: Artificial Sequence
<220> FEATURE:

<223> OTHER INFORMATION: humanized antibody

<400> SEQUENCE: 31

Gln Val Gln Leu Gln Glu Ser Gly Gly Asp Leu Val Gln Pro Gly Ala
1               5                   10                  15

Ser Leu Arg Leu Ser Cys Ala Ala Ser Gly Phe Ser Phe Ser Ser Thr
            20                  25                  30

Tyr Tyr Met Cys Trp Val Arg Gln Ala Pro Gly Lys Gly Leu Glu Trp
        35                  40                  45

Val Ala Cys Ile Tyr Ala Gly Ser Ser Gly Ser Thr Tyr Tyr Ala Ser
    50                  55                  60

Trp Ala Lys Gly Arg Phe Thr Ile Ser Lys Asn Ser Ser Thr Leu Tyr
65                  70                  75                  80

Leu Gln Met Asn Ser Leu Arg Ala Glu Asp Thr Ala Val Tyr Phe Cys
                85                  90                  95

Ala Arg Val Asp Gly Ser Ser Gly Ser Trp Asp Leu Trp Gly Gln
            100                 105                 110

Gly Thr Leu Val Thr Val Ser Ser
        115                 120

<210> SEQ ID NO 32
<211> LENGTH: 121
<212> TYPE: PRT
<213> ORGANISM: Artificial Sequence
<220> FEATURE:
<223> OTHER INFORMATION: humanized antibody

<400> SEQUENCE: 32

Glu Val Gln Leu Glu Glu Ser Gly Gly Asp Leu Val Gln Pro Gly Ala
1               5                   10                  15

Ser Leu Arg Leu Ser Cys Ala Ala Ser Gly Ile Ser Phe Ser Ser Ser
            20                  25                  30

Asp Phe Met Cys Trp Val Arg Gln Ala Pro Gly Lys Gly Leu Glu Trp
        35                  40                  45

Val Ala Cys Ile Tyr Ala Gly Ser Ser Val Ser Ile Tyr Tyr Ala Thr
    50                  55                  60

Trp Ala Lys Gly Arg Phe Thr Ile Ser Lys Ala Ser Ser Thr Thr Leu
65                  70                  75                  80

Tyr Leu Gln Met Asn Ser Leu Arg Ala Glu Asp Thr Ala Val Tyr Phe
                85                  90                  95

Cys Ala Arg Ser Thr Gly Ser Val Gly Arg Gly Phe Asn Leu Trp Gly
            100                 105                 110

Gln Gly Thr Leu Val Thr Val Ser Ser
        115                 120

<210> SEQ ID NO 33
<211> LENGTH: 121
<212> TYPE: PRT
<213> ORGANISM: Artificial Sequence
<220> FEATURE:
<223> OTHER INFORMATION: humanized antibody

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Ile
            20                  25                  30

Tyr Tyr Met Cys Trp Val Arg Gln Ala Pro Gly Lys Gly Leu Glu Trp

```
                35                  40                  45
Val Gly Cys Ile Tyr Thr Gly Asn Ser Asp Phe Thr Tyr Tyr Ala Asn
        50                  55                  60

Trp Ala Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Val Tyr
                85                  90                  95

Phe Cys Ala Arg Phe Arg Asp Asp Tyr Ala Ser Leu Lys Leu Trp Gly
                100                 105                 110

Gln Gly Thr Leu Val Thr Val Ser Ser
        115                 120

<210> SEQ ID NO 34
<211> LENGTH: 120
<212> TYPE: PRT
<213> ORGANISM: Artificial Sequence
<220> FEATURE:
<223> OTHER INFORMATION: humanized antibody

<400> SEQUENCE: 34

Gln Val Gln Leu Gln Glu Ser Gly Gly Gly Leu Val Gln Pro Gly Gly
1               5                   10                  15

Ser Leu Arg Leu Ser Cys Thr Ala Ser Gly Phe Ser Phe Ser Ser Gly
                20                  25                  30

Tyr Asp Met Cys Trp Val Arg Gln Ala Pro Gly Lys Gly Leu Glu Trp
                35                  40                  45

Val Gly Cys Ile Tyr Thr Gly Ser Gly Ser Thr Tyr Tyr Ala Asn Trp
        50                  55                  60

Ala Lys Gly Arg Phe Thr Ile Ser Lys Asp Asn Ser Lys Thr Thr Leu
65                  70                  75                  80

Tyr Leu Gln Met Asn Ser Leu Arg Ala Glu Asp Thr Ala Val Tyr Phe
                85                  90                  95

Cys Ala Arg Asn Ser Asn Asp Trp Met Tyr Phe Asn Leu Trp Gly Gln
                100                 105                 110

Gly Thr Leu Val Thr Val Ser Ser
        115                 120

<210> SEQ ID NO 35
<211> LENGTH: 110
<212> TYPE: PRT
<213> ORGANISM: Artificial Sequence
<220> FEATURE:
<223> OTHER INFORMATION: humanized antibody

<400> SEQUENCE: 35

Asp Ile Val Met Thr Gln Ser Pro Ser Ser Leu Ser Ala Ser Val Gly
1               5                   10                  15

Asp Arg Val Thr Ile Thr Cys Gln Ala Ser Glu Ser Ile Ser Asn Tyr
                20                  25                  30

Leu Ser Trp Tyr Gln Gln Lys Pro Gly Gln Ala Pro Lys Leu Leu Ile
                35                  40                  45

Tyr Leu Ala Ser Thr Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Trp Trp Val Ile Glu His
                85                  90                  95
```

```
Asn Gly Ala Ala Phe Gly Gly Gly Thr Lys Val Val Ile Lys
            100                 105                 110

<210> SEQ ID NO 36
<211> LENGTH: 110
<212> TYPE: PRT
<213> ORGANISM: Artificial Sequence
<220> FEATURE:
<223> OTHER INFORMATION: humanized antibody

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Ser Ile Tyr Ser Asn
            20                  25                  30

Leu Ala Trp Tyr Gln Gln Lys Pro Gly Gln Ala Pro Lys Leu Leu Ile
        35                  40                  45

Tyr Ala Ala Ser Leu Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ala Ser Tyr Ser Thr Gly
                85                  90                  95

Pro Asp Trp Thr Phe Gly Gln Gly Thr Lys Val Val Ile Lys
            100                 105                 110

<210> SEQ ID NO 37
<211> LENGTH: 110
<212> TYPE: PRT
<213> ORGANISM: Artificial Sequence
<220> FEATURE:
<223> OTHER INFORMATION: humanized antibody

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Tyr Ile Tyr
            20                  25                  30

Leu Ser Trp Tyr Gln Gln Lys Pro Gly Gln Ala Pro Lys Leu Leu Ile
        35                  40                  45

Tyr Asp Ala Ser Lys Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ala Thr Thr Tyr Asn
                85                  90                  95

Val Asp Asn Val Phe Gly Gln Gly Thr Lys Val Val Ile Lys
            100                 105                 110

<210> SEQ ID NO 38
<211> LENGTH: 111
<212> TYPE: PRT
<213> ORGANISM: Artificial Sequence
<220> FEATURE:
<223> OTHER INFORMATION: humanized antibody

<400> SEQUENCE: 38

Asp Ile Val Met Thr Gln Ser Pro Ser Ser Leu Ser Ala Ser Val Gly
1               5                   10                  15

Asp Arg Val Thr Ile Thr Cys Gln Ala Ser Glu Asn Ile Gly Asn Gly
```

```
                    20                  25                  30

Leu Ala Trp Tyr Gln Gln Lys Pro Gly Gln Ala Pro Lys Leu Leu Ile
                35                  40                  45

Tyr Gly Ala Ser Thr Leu Ala Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Cys Thr Tyr Trp Asn Pro Asp
                85                  90                  95

Tyr Ile Gly Gly Ala Phe Gly Gly Thr Lys Val Val Ile Lys
                100                 105                 110

<210> SEQ ID NO 39
<211> LENGTH: 110
<212> TYPE: PRT
<213> ORGANISM: Artificial Sequence
<220> FEATURE:
<223> OTHER INFORMATION: humanized antibody

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Asp Ile Tyr Ser Gly
                20                  25                  30

Ile Ser Trp Tyr Gln Gln Lys Pro Gly Lys Ala Pro Lys Leu Leu Ile
                35                  40                  45

Tyr Ala Ala Ser Asn Leu Glu Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gly Gly Tyr Ser Tyr Ser Asn
                85                  90                  95

Thr Gly Pro Thr Phe Gly Gln Gly Thr Lys Val Glu Ile Lys
                100                 105                 110

<210> SEQ ID NO 40
<211> LENGTH: 113
<212> TYPE: PRT
<213> ORGANISM: Artificial Sequence
<220> FEATURE:
<223> OTHER INFORMATION: humanized antibody

<400> SEQUENCE: 40

Asp Ile Val Met Thr Gln Ser Pro Ser Ser Leu Ser Ala Ser Val Gly
1               5                   10                  15

Asp Arg Val Thr Ile Thr Cys Gln Ala Ser Glu Asp Ile Tyr Ser Asn
                20                  25                  30

Leu Ala Trp Phe Gln Gln Lys Pro Gly Gln Ala Pro Lys Leu Leu Ile
                35                  40                  45

Tyr Gly Ala Ser Thr Leu Ala Ser Gly Val Pro Ser Arg Phe Ser Gly
            50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gly Val Cys Thr Asp Ile Ser
                85                  90                  95

Thr Asp Asp Leu Tyr Asn Ala Phe Gly Gln Gly Thr Lys Val Val Ile
                100                 105                 110
```

Lys

<210> SEQ ID NO 41
<211> LENGTH: 110
<212> TYPE: PRT
<213> ORGANISM: Artificial Sequence
<220> FEATURE:
<223> OTHER INFORMATION: humanized antibody

<400> SEQUENCE: 41

Asp Ile Val Met Thr Gln Ser Pro Ser Ser Leu Ser Ala Ser Val Gly
1               5                   10                  15

Asp Arg Val Thr Ile Thr Cys Gln Ala Ser Glu Asp Ile Tyr Ser Asn
            20                  25                  30

Leu Ala Trp Phe Gln Gln Lys Pro Gly Gln Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gly Val Tyr Thr Tyr Ser Thr
                85                  90                  95

Asp Ile His Ala Phe Gly Gly Gly Thr Lys Val Val Ile Lys
            100                 105                 110

<210> SEQ ID NO 42
<211> LENGTH: 110
<212> TYPE: PRT
<213> ORGANISM: Artificial Sequence
<220> FEATURE:
<223> OTHER INFORMATION: humanized antibody

<400> SEQUENCE: 42

Asp Ile Val Met Thr Gln Ser Pro Ser Ser Leu Ser Ala Ser Val Gly
1               5                   10                  15

Asp Arg Val Thr Ile Thr Cys Gln Ala Ser Glu Asp Ile Tyr Ser Asn
            20                  25                  30

Leu Ala Trp Phe Gln Gln Lys Pro Gly Gln Ala Pro Lys Leu Leu Ile
        35                  40                  45

Tyr Asp Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gly Val Tyr Thr His Ile Ser
                85                  90                  95

Ala Asp Asn Ala Phe Gly Gly Gly Thr Lys Val Val Ile Lys
            100                 105                 110

<210> SEQ ID NO 43
<211> LENGTH: 111
<212> TYPE: PRT
<213> ORGANISM: Artificial Sequence
<220> FEATURE:
<223> OTHER INFORMATION: humanized antibody

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Ser
            20                  25                  30

Leu Ala Trp Tyr Gln Gln Lys Pro Gly Gln Ala Pro Lys Leu Leu Ile
            35                  40                  45

Tyr Asp Ala Ser Asp Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Tyr Ser Gly Gly
                85                  90                  95

Thr Asp Asn Asp Val Phe Gly Gly Gly Thr Lys Val Val Ile Lys
                100                 105                 110

<210> SEQ ID NO 44
<211> LENGTH: 112
<212> TYPE: PRT
<213> ORGANISM: Artificial Sequence
<220> FEATURE:
<223> OTHER INFORMATION: humanized antibody

<400> SEQUENCE: 44

Asp Ile Val Met Thr Gln Ser Pro Ser Ser Leu Ser Ala Ser Val Gly
1               5                   10                  15

Asp Arg Val Thr Ile Thr Cys Gln Ser Ser Gln Ser Val Asp Gly Asn
            20                  25                  30

Asn Leu Leu Ser Trp Tyr Gln Gln Lys Pro Gly Gln Ala Pro Lys Leu
        35                  40                  45

Leu Ile Tyr Asp Ala Ser Asn Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gly Ser Tyr Tyr Ser
                85                  90                  95

Ser Ser Trp Tyr Asn Val Phe Gly Gln Gly Thr Lys Val Val Ile Lys
                100                 105                 110

<210> SEQ ID NO 45
<211> LENGTH: 108
<212> TYPE: PRT
<213> ORGANISM: Artificial Sequence
<220> FEATURE:
<223> OTHER INFORMATION: humanized antibody

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Tyr Ser Phe
            20                  25                  30

Leu Ser Trp Tyr Gln Gln Lys Pro Gly Gln Ala Pro Lys Leu Leu Ile
        35                  40                  45

Tyr Ala Ala Ser Asp Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Cys Asn Tyr Ile Ile Asp Tyr
                85                  90                  95

Gly Ala Phe Gly Gln Gly Thr Lys Val Val Ile Lys
                100                 105

```
<210> SEQ ID NO 46
<211> LENGTH: 108
<212> TYPE: PRT
<213> ORGANISM: Artificial Sequence
<220> FEATURE:
<223> OTHER INFORMATION: humanized antibody

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Gly Tyr Tyr
            20                  25                  30

Leu Ala Trp Tyr Gln Gln Lys Pro Gly Gln Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Tyr Asn Ser Asp Ser
                85                  90                  95

Asp Ala Phe Gly Gln Gly Thr Lys Val Val Ile Lys
            100                 105

<210> SEQ ID NO 47
<211> LENGTH: 110
<212> TYPE: PRT
<213> ORGANISM: Artificial Sequence
<220> FEATURE:
<223> OTHER INFORMATION: humanized antibody

<400> SEQUENCE: 47

Asp Ile Val Met Thr Gln Ser Pro Ser Ser Leu Ser Ala Ser Val Gly
1               5                   10                  15

Asp Arg Val Thr Ile Thr Cys Gln Ala Ser Gln Thr Ile Ser Ile Asn
            20                  25                  30

Leu Ala Trp Tyr Gln Gln Lys Pro Gly Gln Ala Pro Lys Leu Leu Ile
        35                  40                  45

Tyr Tyr Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Thr Glu Asp Asn
                85                  90                  95

Ile Asp Asn Thr Phe Gly Gln Gly Thr Lys Val Val Ile Lys
            100                 105                 110

<210> SEQ ID NO 48
<211> LENGTH: 110
<212> TYPE: PRT
<213> ORGANISM: Artificial Sequence
<220> FEATURE:
<223> OTHER INFORMATION: humanized antibody

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asn Ile Tyr Ser Asn
            20                  25                  30

Leu Ala Trp Tyr Gln Gln Lys Pro Gly Gln Ala Pro Lys Leu Leu Ile
        35                  40                  45
```

```
Tyr Ala Ala Ser Leu Leu Ala Ser Gly Val Pro Ser Arg Phe Ser Gly
     50                  55                  60

Ser Gly Ser Gly Thr Asp Phe Thr Leu Thr Ile Ser Ser Leu Gln Pro
 65              70                  75                      80

Glu Asp Phe Ala Thr Tyr Tyr Cys Gln Gly Ala Val Tyr Ser Gly Asn
                 85                  90                  95

Thr Glu Trp Ala Phe Gly Gln Gly Thr Lys Val Val Ile Lys
            100                 105                 110
```

<210> SEQ ID NO 49
<211> LENGTH: 113
<212> TYPE: PRT
<213> ORGANISM: Artificial Sequence
<220> FEATURE:
<223> OTHER INFORMATION: humanized antibody

<400> SEQUENCE: 49

```
Asp Ile Val Met Thr Gln Ser Pro Ser Ser Leu Ser Ala Ser Val Gly
  1               5                  10                  15

Asp Arg Val Thr Ile Thr Cys Gln Ala Ser Gln Ser Val Tyr Asn Ser
                 20                  25                  30

Asn His Leu Ser Trp Tyr Gln Gln Lys Pro Gly Gln Ala Pro Lys Leu
             35                  40                  45

Leu Ile Tyr Ser Ala Ser Thr Leu Ala Ser Gly Val Pro Ser Arg Phe
     50                  55                  60

Ser Gly Ser Gly Ser Gly Thr Asp Phe Thr Leu Thr Ile Ser Ser Leu
 65              70                  75                      80

Gln Pro Glu Asp Phe Ala Thr Tyr Tyr Cys Gln Gly Glu Phe Ser Cys
                 85                  90                  95

Val Ser Ala Asp Cys Ile Ala Phe Gly Gly Gly Thr Lys Val Val Ile
                100                 105                 110

Lys
```

<210> SEQ ID NO 50
<211> LENGTH: 110
<212> TYPE: PRT
<213> ORGANISM: Artificial Sequence
<220> FEATURE:
<223> OTHER INFORMATION: humanized antibody

<400> SEQUENCE: 50

```
Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Ser Ile Ser Ser Tyr
                 20                  25                  30

Leu Ser Trp Tyr Gln Gln Lys Pro Gly Gln Ala Pro Lys Leu Leu Ile
             35                  40                  45

Tyr Gly Ala Ser Asn Leu Ala Ser Gly Val Pro Ser Arg Phe Ser Gly
     50                  55                  60

Ser Gly Ser Gly Thr Asp Phe Thr Leu Thr Ile Ser Ser Leu Gln Pro
 65              70                  75                      80

Glu Asp Phe Ala Thr Tyr Tyr Cys Gln Cys Thr Tyr Tyr Asp Asn Asn
                 85                  90                  95

Tyr Gly Gly Ala Phe Gly Gly Gly Thr Lys Val Val Ile Lys
            100                 105                 110
```

<210> SEQ ID NO 51

```
<211> LENGTH: 114
<212> TYPE: PRT
<213> ORGANISM: Artificial Sequence
<220> FEATURE:
<223> OTHER INFORMATION: humanized antibody

<400> SEQUENCE: 51

Asp Ile Val Met Thr Gln Ser Pro Ser Ser Leu Ser Ala Ser Val Gly
1               5                   10                  15

Asp Arg Val Thr Ile Thr Cys Gln Ala Ser Glu Ser Ile Ser Ala Asn
            20                  25                  30

Tyr Trp Ser Trp Tyr Gln Gln Lys Pro Gly Gln Ala Pro Lys Leu Leu
        35                  40                  45

Ile Tyr Gly Ala Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Phe Cys Gln Ser Trp Tyr Tyr Ser Gly
                85                  90                  95

Ser Gly Ser Tyr His Ser Trp Ala Phe Gly Gln Gly Thr Lys Val Val
            100                 105                 110

Ile Lys

<210> SEQ ID NO 52
<211> LENGTH: 110
<212> TYPE: PRT
<213> ORGANISM: Artificial Sequence
<220> FEATURE:
<223> OTHER INFORMATION: humanized antibody

<400> SEQUENCE: 52

Asp Ile Val Met Thr Gln Ser Pro Ser Ser Leu Ser Ala Ser Val Gly
1               5                   10                  15

Asp Arg Val Thr Ile Thr Cys Gln Ala Ser Glu Ser Ile Ser Asn Tyr
            20                  25                  30

Leu Ser Trp Tyr Gln Gln Lys Pro Gly Gln Ala Pro Lys Leu Leu Ile
        35                  40                  45

Tyr Leu Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Trp Trp Val Ile Glu His
                85                  90                  95

Asn Gly Ala Ala Phe Gly Gly Gly Thr Lys Val Val Ile Lys
            100                 105                 110

<210> SEQ ID NO 53
<211> LENGTH: 110
<212> TYPE: PRT
<213> ORGANISM: Artificial Sequence
<220> FEATURE:
<223> OTHER INFORMATION: humanized antibody

<400> SEQUENCE: 53

Ala Ile Gln Met Thr Gln Ser Pro Ser Ser Leu Ser Ala Ser Val Gly
1               5                   10                  15

Asp Arg Val Thr Ile Thr Cys Gln Ala Ser Glu Ser Ile Tyr Ser Asn
            20                  25                  30

Leu Ala Trp Tyr Gln Gln Lys Pro Gly Gln Ala Pro Lys Leu Leu Ile
```

```
                35                  40                  45
Tyr Ala Ala Ser Leu Leu Ala Ser Gly Val Pro Ser Arg Phe Ser Gly
         50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Ser Ala Ser Tyr Ser Thr Gly
                 85                  90                  95

Pro Asp Trp Thr Phe Gly Gln Gly Thr Lys Val Val Ile Lys
                100                 105                 110

<210> SEQ ID NO 54
<211> LENGTH: 110
<212> TYPE: PRT
<213> ORGANISM: Artificial Sequence
<220> FEATURE:
<223> OTHER INFORMATION: humanized antibody

<400> SEQUENCE: 54

Ala Ile Arg Met Thr Gln Ser Pro Ser Ser Leu Ser Ala Ser Val Gly
 1               5                  10                  15

Asp Arg Val Thr Ile Thr Cys Gln Ala Ser Gln Ser Ile Tyr Ile Tyr
                 20                  25                  30

Leu Ser Trp Tyr Gln Gln Lys Pro Gly Gln Ala Pro Lys Leu Leu Ile
             35                  40                  45

Tyr Asp Ala Ser Lys Leu Ala Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Ala Thr Thr Tyr Asn
                 85                  90                  95

Val Asp Asn Val Phe Gly Gln Gly Thr Lys Val Val Ile Lys
                100                 105                 110

<210> SEQ ID NO 55
<211> LENGTH: 111
<212> TYPE: PRT
<213> ORGANISM: Artificial Sequence
<220> FEATURE:
<223> OTHER INFORMATION: humanized antibody

<400> SEQUENCE: 55

Glu Leu Val Met Thr Gln Ser Pro Ser Ser Leu Ser Ala Ser Val Gly
 1               5                  10                  15

Asp Arg Val Thr Ile Thr Cys Gln Ala Ser Glu Asn Ile Gly Asn Gly
                 20                  25                  30

Leu Ala Trp Tyr Gln Gln Lys Pro Gly Gln Ala Pro Lys Leu Leu Ile
             35                  40                  45

Tyr Gly Ala Ser Thr Leu Ala Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Cys Thr Tyr Trp Asn Pro Asp
                 85                  90                  95

Tyr Ile Gly Gly Ala Phe Gly Gly Gly Thr Lys Val Val Ile Lys
                100                 105                 110

<210> SEQ ID NO 56
<211> LENGTH: 110
```

```
<212> TYPE: PRT
<213> ORGANISM: Artificial Sequence
<220> FEATURE:
<223> OTHER INFORMATION: humanized antibody

<400> SEQUENCE: 56

Ala Ile Gln Met Thr Gln Ser Pro Ser Ser Leu Ser Ala Ser Val Gly
1               5                   10                  15

Asp Arg Val Thr Ile Thr Cys Leu Ala Ser Glu Asp Ile Tyr Ser Gly
            20                  25                  30

Ile Ser Trp Tyr Gln Gln Lys Pro Gly Lys Ala Pro Lys Leu Leu Ile
        35                  40                  45

Tyr Ala Ala Ser Asn Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gly Gly Tyr Ser Tyr Ser Asn
                85                  90                  95

Thr Gly Pro Thr Phe Gly Gln Gly Thr Lys Val Glu Ile Lys
                100                 105                 110

<210> SEQ ID NO 57
<211> LENGTH: 113
<212> TYPE: PRT
<213> ORGANISM: Artificial Sequence
<220> FEATURE:
<223> OTHER INFORMATION: humanized antibody

<400> SEQUENCE: 57

Asp Ile Val Met Thr Gln Ser Pro Ser Ser Leu Ser Ala Ser Val Gly
1               5                   10                  15

Asp Arg Val Thr Ile Thr Cys Gln Ala Ser Glu Asp Ile Tyr Ser Asn
            20                  25                  30

Leu Ala Trp Phe Gln Gln Lys Pro Gly Gln Ala Pro Lys Leu Leu Ile
        35                  40                  45

Tyr Gly Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gly Val Cys Thr Asp Ile Ser
                85                  90                  95

Thr Asp Asp Leu Tyr Asn Ala Phe Gly Gln Gly Thr Lys Val Val Ile
                100                 105                 110

Lys

<210> SEQ ID NO 58
<211> LENGTH: 110
<212> TYPE: PRT
<213> ORGANISM: Artificial Sequence
<220> FEATURE:
<223> OTHER INFORMATION: humanized antibody

<400> SEQUENCE: 58

Asp Ile Val Met Thr Gln Ser Pro Ser Ser Leu Ser Ala Ser Val Gly
1               5                   10                  15

Asp Arg Val Thr Ile Thr Cys Gln Ala Ser Glu Asp Ile Tyr Ser Asn
            20                  25                  30

Leu Ala Trp Phe Gln Gln Lys Pro Gly Gln Ala Pro Lys Leu Leu Ile
        35                  40                  45
```

Tyr Arg Ala Ser Thr Leu Ala Ser Gly Val Pro Ser Arg Phe Ser Gly
                50                  55                  60

Ser Gly Ser Gly Thr Glu Phe Thr Leu Thr Ile Ser Ser Leu Gln Pro
65                      70                  75                  80

Glu Asp Phe Ala Thr Tyr Tyr Cys Leu Gly Val Tyr Thr Tyr Ser Thr
                        85                  90                  95

Asp Ile His Ala Phe Gly Gly Gly Thr Lys Val Val Ile Lys
                100                 105                 110

<210> SEQ ID NO 59
<211> LENGTH: 110
<212> TYPE: PRT
<213> ORGANISM: Artificial Sequence
<220> FEATURE:
<223> OTHER INFORMATION: humanized antibody

<400> SEQUENCE: 59

Glu Leu Val Met Thr Gln Ser Pro Ser Ser Leu Ser Ala Ser Val Gly
1               5                   10                  15

Asp Arg Val Thr Ile Thr Cys Gln Ala Ser Glu Asp Ile Tyr Ser Asn
                20                  25                  30

Leu Ala Trp Phe Gln Gln Lys Pro Gly Gln Ala Pro Lys Leu Leu Ile
            35                  40                  45

Tyr Asp Ala Ser Thr Leu Ala Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gly Val Tyr Thr His Ile Ser
                85                  90                  95

Ala Asp Asn Ala Phe Gly Gly Gly Thr Lys Val Glu Ile Lys
            100                 105                 110

<210> SEQ ID NO 60
<211> LENGTH: 111
<212> TYPE: PRT
<213> ORGANISM: Artificial Sequence
<220> FEATURE:
<223> OTHER INFORMATION: humanized antibody

<400> SEQUENCE: 60

Ala Leu Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Ser
                20                  25                  30

Leu Ala Trp Tyr Gln Gln Lys Pro Gly Gln Ala Pro Lys Leu Leu Ile
            35                  40                  45

Tyr Asp Ala Ser Asp Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Tyr Ser Gly Gly
                85                  90                  95

Thr Asp Asn Asp Val Phe Gly Gly Gly Thr Lys Val Val Ile Lys
            100                 105                 110

<210> SEQ ID NO 61
<211> LENGTH: 112
<212> TYPE: PRT

```
<213> ORGANISM: Artificial Sequence
<220> FEATURE:
<223> OTHER INFORMATION: humanized antibody

<400> SEQUENCE: 61

Asn Ile Val Met Thr Gln Ser Pro Ser Ser Leu Ser Ala Ser Val Gly
1               5                   10                  15

Asp Arg Val Thr Ile Thr Cys Gln Ser Ser Gln Ser Val Asp Gly Asn
            20                  25                  30

Asn Leu Leu Ser Trp Tyr Gln Gln Lys Pro Gly Gln Ala Pro Lys Leu
        35                  40                  45

Leu Ile Tyr Asp Ala Ser Asn Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gly Ser Tyr Tyr Ser
                85                  90                  95

Ser Ser Trp Tyr Asn Val Phe Gly Gln Gly Thr Lys Val Val Ile Lys
            100                 105                 110

<210> SEQ ID NO 62
<211> LENGTH: 108
<212> TYPE: PRT
<213> ORGANISM: Artificial Sequence
<220> FEATURE:
<223> OTHER INFORMATION: humanized antibody

<400> SEQUENCE: 62

Asp Val Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Tyr Ser Phe
            20                  25                  30

Leu Ser Trp Tyr Gln Gln Lys Pro Gly Gln Ala Pro Lys Leu Leu Ile
        35                  40                  45

Tyr Ala Ala Ser Asp Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Cys Asn Tyr Ile Ile Asp Tyr
                85                  90                  95

Gly Ala Phe Gly Gln Gly Thr Lys Val Val Ile Lys
            100                 105

<210> SEQ ID NO 63
<211> LENGTH: 108
<212> TYPE: PRT
<213> ORGANISM: Artificial Sequence
<220> FEATURE:
<223> OTHER INFORMATION: humanized antibody

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Gly Tyr Tyr
            20                  25                  30

Leu Ala Trp Tyr Gln Gln Lys Pro Gly Gln Ala Pro Lys Leu Leu Ile
        35                  40                  45

Tyr Arg Ala Ser Thr Leu Ala Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Ser Tyr Tyr Asn Ser Asp Ser
                 85                  90                  95

Asp Ala Phe Gly Gln Gly Thr Lys Val Val Ile Lys
            100                 105
```

<210> SEQ ID NO 64
<211> LENGTH: 110
<212> TYPE: PRT
<213> ORGANISM: Artificial Sequence
<220> FEATURE:
<223> OTHER INFORMATION: humanized antibody

<400> SEQUENCE: 64

```
Ala Ile Val Met Thr Gln Ser Pro Ser Ser Leu Ser Ala Ser Val Gly
  1               5                  10                  15

Asp Arg Val Thr Ile Thr Cys Gln Ala Ser Gln Thr Ile Ser Ile Asn
                 20                  25                  30

Leu Ala Trp Tyr Gln Gln Lys Pro Gly Gln Ala Pro Lys Leu Leu Ile
             35                  40                  45

Tyr Tyr Ala Ser Thr Leu Ala Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Tyr Thr Glu Asp Asn
                 85                  90                  95

Ile Asp Asn Thr Phe Gly Gln Gly Thr Lys Val Val Ile Lys
            100                 105                 110
```

<210> SEQ ID NO 65
<211> LENGTH: 110
<212> TYPE: PRT
<213> ORGANISM: Artificial Sequence
<220> FEATURE:
<223> OTHER INFORMATION: humanized antibody

<400> SEQUENCE: 65

```
Ala Ile Gln Met Thr Gln Ser Pro Ser Ser Leu Ser Ala Ser Val Gly
  1               5                  10                  15

Asp Arg Val Thr Ile Thr Cys Gln Ala Ser Gln Asn Ile Tyr Ser Asn
                 20                  25                  30

Leu Ala Trp Tyr Gln Gln Lys Pro Gly Gln Ala Pro Lys Leu Leu Ile
             35                  40                  45

Tyr Ala Ala Ser Leu Leu Ala Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gly Ala Val Tyr Ser Gly Asn
                 85                  90                  95

Thr Glu Trp Ala Phe Gly Gln Gly Thr Lys Val Val Ile Lys
            100                 105                 110
```

<210> SEQ ID NO 66
<211> LENGTH: 113
<212> TYPE: PRT
<213> ORGANISM: Artificial Sequence
<220> FEATURE:
<223> OTHER INFORMATION: humanized antibody

```
<400> SEQUENCE: 66

Asp Ile Val Met Thr Gln Ser Pro Ser Ser Leu Ser Ala Ser Val Gly
1               5                   10                  15

Asp Arg Val Thr Ile Thr Cys Gln Ala Ser Gln Ser Val Tyr Asn Ser
            20                  25                  30

Asn His Leu Ser Trp Tyr Gln Gln Lys Pro Gly Gln Ala Pro Lys Leu
        35                  40                  45

Leu Ile Tyr Ser Ala Ser Thr Leu Ala Ser Gly Val Pro Ser Arg Phe
50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gly Glu Phe Ser Cys
                85                  90                  95

Val Ser Ala Asp Cys Ile Ala Phe Gly Gly Gly Thr Lys Val Val Ile
            100                 105                 110

Lys

<210> SEQ ID NO 67
<211> LENGTH: 110
<212> TYPE: PRT
<213> ORGANISM: Artificial Sequence
<220> FEATURE:
<223> OTHER INFORMATION: humanized antibody

<400> SEQUENCE: 67

Asp Val Val Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30

Leu Ser Trp Tyr Gln Gln Lys Pro Gly Gln Ala Pro Lys Leu Leu Ile
        35                  40                  45

Tyr Gly Ala Ser Asn Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Cys Thr Tyr Tyr Asp Asn Asn
                85                  90                  95

Tyr Gly Gly Ala Phe Gly Gly Gly Thr Lys Val Glu Ile Lys
            100                 105                 110

<210> SEQ ID NO 68
<211> LENGTH: 114
<212> TYPE: PRT
<213> ORGANISM: Artificial Sequence
<220> FEATURE:
<223> OTHER INFORMATION: humanized antibody

<400> SEQUENCE: 68

Asp Ile Val Met Thr Gln Ser Pro Ser Ser Leu Ser Ala Ser Val Gly
1               5                   10                  15

Asp Arg Val Thr Ile Thr Cys Gln Ala Ser Glu Ser Ile Ser Ala Asn
            20                  25                  30

Tyr Trp Ser Trp Tyr Gln Gln Lys Pro Gly Gln Ala Pro Lys Leu Leu
        35                  40                  45

Ile Tyr Gly Ala Ser Thr Leu Ala Ser Gly Val Pro Ser Arg Phe Ser
50                  55                  60
```

```
Gly Ser Gly Ser Gly Thr Asp Phe Thr Leu Thr Ile Ser Ser Leu Gln
 65                  70                  75                  80

Pro Glu Asp Phe Ala Thr Tyr Phe Cys Gln Ser Trp Tyr Ser Gly
                 85                  90                  95

Ser Gly Ser Tyr His Ser Trp Ala Phe Gly Gln Gly Thr Lys Val Val
            100                 105                 110

Ile Lys

<210> SEQ ID NO 69
<211> LENGTH: 6
<212> TYPE: PRT
<213> ORGANISM: Artificial Sequence
<220> FEATURE:
<223> OTHER INFORMATION: humanized antibody

<400> SEQUENCE: 69

Ser Ser Tyr Trp Ile Cys
1               5

<210> SEQ ID NO 70
<211> LENGTH: 6
<212> TYPE: PRT
<213> ORGANISM: Artificial Sequence
<220> FEATURE:
<223> OTHER INFORMATION: humanized antibody

<400> SEQUENCE: 70

Ser Ser His Tyr Met Cys
1               5

<210> SEQ ID NO 71
<211> LENGTH: 5
<212> TYPE: PRT
<213> ORGANISM: Artificial Sequence
<220> FEATURE:
<223> OTHER INFORMATION: humanized antibody

<400> SEQUENCE: 71

Ser Tyr Ala Met Gly
1               5

<210> SEQ ID NO 72
<211> LENGTH: 5
<212> TYPE: PRT
<213> ORGANISM: Artificial Sequence
<220> FEATURE:
<223> OTHER INFORMATION: humanized antibody

<400> SEQUENCE: 72

Asn Tyr Ala Met Gly
1               5

<210> SEQ ID NO 73
<211> LENGTH: 5
<212> TYPE: PRT
<213> ORGANISM: Artificial Sequence
<220> FEATURE:
<223> OTHER INFORMATION: humanized antibody

<400> SEQUENCE: 73

Ser Tyr Tyr Met Ser
1               5

<210> SEQ ID NO 74
<211> LENGTH: 6
```

<212> TYPE: PRT
<213> ORGANISM: Artificial Sequence
<220> FEATURE:
<223> OTHER INFORMATION: humanized antibody

<400> SEQUENCE: 74

Ser Asn Tyr Trp Ile Cys
1               5

<210> SEQ ID NO 75
<211> LENGTH: 6
<212> TYPE: PRT
<213> ORGANISM: Artificial Sequence
<220> FEATURE:
<223> OTHER INFORMATION: humanized antibody

<400> SEQUENCE: 75

Ser Ser Tyr Tyr Met Cys
1               5

<210> SEQ ID NO 76
<211> LENGTH: 6
<212> TYPE: PRT
<213> ORGANISM: Artificial Sequence
<220> FEATURE:
<223> OTHER INFORMATION: humanized antibody

<400> SEQUENCE: 76

Thr Ser Tyr Trp Arg Cys
1               5

<210> SEQ ID NO 77
<211> LENGTH: 6
<212> TYPE: PRT
<213> ORGANISM: Artificial Sequence
<220> FEATURE:
<223> OTHER INFORMATION: humanized antibody

<400> SEQUENCE: 77

Ser Tyr Tyr Tyr Met Cys
1               5

<210> SEQ ID NO 78
<211> LENGTH: 5
<212> TYPE: PRT
<213> ORGANISM: Artificial Sequence
<220> FEATURE:
<223> OTHER INFORMATION: humanized antibody

<400> SEQUENCE: 78

Ser Tyr Trp Met Ser
1               5

<210> SEQ ID NO 79
<211> LENGTH: 5
<212> TYPE: PRT
<213> ORGANISM: Artificial Sequence
<220> FEATURE:
<223> OTHER INFORMATION: humanized antibody

<400> SEQUENCE: 79

Ser Tyr Asp Met Ser
1               5

<210> SEQ ID NO 80
<211> LENGTH: 6
<212> TYPE: PRT

```
<213> ORGANISM: Artificial Sequence
<220> FEATURE:
<223> OTHER INFORMATION: humanized antibody

<400> SEQUENCE: 80

Ser Asn Tyr Tyr Met Cys
1               5

<210> SEQ ID NO 81
<211> LENGTH: 6
<212> TYPE: PRT
<213> ORGANISM: Artificial Sequence
<220> FEATURE:
<223> OTHER INFORMATION: humanized antibody

<400> SEQUENCE: 81

Phe Gly Tyr Tyr Met Cys
1               5

<210> SEQ ID NO 82
<211> LENGTH: 6
<212> TYPE: PRT
<213> ORGANISM: Artificial Sequence
<220> FEATURE:
<223> OTHER INFORMATION: humanized antibody

<400> SEQUENCE: 82

Ser Thr Tyr Tyr Met Cys
1               5

<210> SEQ ID NO 83
<211> LENGTH: 6
<212> TYPE: PRT
<213> ORGANISM: Artificial Sequence
<220> FEATURE:
<223> OTHER INFORMATION: humanized antibody

<400> SEQUENCE: 83

Ser Ser Asp Phe Met Cys
1               5

<210> SEQ ID NO 84
<211> LENGTH: 6
<212> TYPE: PRT
<213> ORGANISM: Artificial Sequence
<220> FEATURE:
<223> OTHER INFORMATION: humanized antibody

<400> SEQUENCE: 84

Ser Ile Tyr Tyr Met Cys
1               5

<210> SEQ ID NO 85
<211> LENGTH: 6
<212> TYPE: PRT
<213> ORGANISM: Artificial Sequence
<220> FEATURE:
<223> OTHER INFORMATION: humanized antibody

<400> SEQUENCE: 85

Ser Gly Tyr Asp Met Cys
1               5

<210> SEQ ID NO 86
<211> LENGTH: 17
<212> TYPE: PRT
<213> ORGANISM: Artificial Sequence
```

<220> FEATURE:
<223> OTHER INFORMATION: humanized antibody

<400> SEQUENCE: 86

Cys Ile Tyr Thr Gly Ser Gly Thr Tyr Tyr Ala Ser Trp Glu Lys
1               5                   10                  15

Gly

<210> SEQ ID NO 87
<211> LENGTH: 18
<212> TYPE: PRT
<213> ORGANISM: Artificial Sequence
<220> FEATURE:
<223> OTHER INFORMATION: humanized antibody

<400> SEQUENCE: 87

Cys Ile Tyr Ala Gly Ser Ser Gly Asn Thr Tyr Tyr Ala Asn Trp Ala
1               5                   10                  15

Lys Gly

<210> SEQ ID NO 88
<211> LENGTH: 16
<212> TYPE: PRT
<213> ORGANISM: Artificial Sequence
<220> FEATURE:
<223> OTHER INFORMATION: humanized antibody

<400> SEQUENCE: 88

Val Ile Thr Ser Ser Ala Thr Thr Tyr Tyr Ala Ser Trp Ala Lys Gly
1               5                   10                  15

<210> SEQ ID NO 89
<211> LENGTH: 16
<212> TYPE: PRT
<213> ORGANISM: Artificial Sequence
<220> FEATURE:
<223> OTHER INFORMATION: humanized antibody

<400> SEQUENCE: 89

Val Ile Ser Ser Asp Gly Phe Phe Tyr Asp Ala Ser Trp Ala Lys Gly
1               5                   10                  15

<210> SEQ ID NO 90
<211> LENGTH: 16
<212> TYPE: PRT
<213> ORGANISM: Artificial Sequence
<220> FEATURE:
<223> OTHER INFORMATION: humanized antibody

<400> SEQUENCE: 90

Ile Ile Ser Gly Ser Ala Ser Thr Tyr Tyr Ala Thr Trp Ala Lys Gly
1               5                   10                  15

<210> SEQ ID NO 91
<211> LENGTH: 17
<212> TYPE: PRT
<213> ORGANISM: Artificial Sequence
<220> FEATURE:
<223> OTHER INFORMATION: humanized antibody

<400> SEQUENCE: 91

Cys Ile Tyr Thr Ser Thr Gly Asn Thr Trp Tyr Ala Ser Trp Ala Lys
1               5                   10                  15

Gly

```
<210> SEQ ID NO 92
<211> LENGTH: 18
<212> TYPE: PRT
<213> ORGANISM: Artificial Sequence
<220> FEATURE:
<223> OTHER INFORMATION: humanized antibody

<400> SEQUENCE: 92

Cys Ile Tyr Ala Gly Ser Ser Gly Val Thr Tyr Tyr Ala Ser Trp Ala
1               5                   10                  15

Lys Gly

<210> SEQ ID NO 93
<211> LENGTH: 18
<212> TYPE: PRT
<213> ORGANISM: Artificial Sequence
<220> FEATURE:
<223> OTHER INFORMATION: humanized antibody

<400> SEQUENCE: 93

Cys Ile Tyr Ala Gly Ser Gly Asp Val Thr Tyr Tyr Ala Asn Trp Val
1               5                   10                  15

Asn Gly

<210> SEQ ID NO 94
<211> LENGTH: 18
<212> TYPE: PRT
<213> ORGANISM: Artificial Sequence
<220> FEATURE:
<223> OTHER INFORMATION: humanized antibody

<400> SEQUENCE: 94

Cys Ile Phe Ile Gly Tyr Gly Asp Val Thr Trp Tyr Ala Ser Trp Ala
1               5                   10                  15

Lys Gly

<210> SEQ ID NO 95
<211> LENGTH: 16
<212> TYPE: PRT
<213> ORGANISM: Artificial Sequence
<220> FEATURE:
<223> OTHER INFORMATION: humanized antibody

<400> SEQUENCE: 95

Met Ile Tyr Gly Ser Gly Tyr Thr Tyr Tyr Ala Ser Trp Ala Lys Gly
1               5                   10                  15

<210> SEQ ID NO 96
<211> LENGTH: 16
<212> TYPE: PRT
<213> ORGANISM: Artificial Sequence
<220> FEATURE:
<223> OTHER INFORMATION: humanized antibody

<400> SEQUENCE: 96

Thr Ile Tyr Ile Gly Gly Thr Thr Ala Tyr Ala Ser Trp Pro Lys Gly
1               5                   10                  15

<210> SEQ ID NO 97
<211> LENGTH: 17
<212> TYPE: PRT
<213> ORGANISM: Artificial Sequence
<220> FEATURE:
<223> OTHER INFORMATION: humanized antibody
```

```
<400> SEQUENCE: 97

Cys Ile Tyr Thr Asn Ser Gly Asn Thr Trp Ser Ala Ser Trp Ala Lys
1               5                   10                  15

Gly

<210> SEQ ID NO 98
<211> LENGTH: 17
<212> TYPE: PRT
<213> ORGANISM: Artificial Sequence
<220> FEATURE:
<223> OTHER INFORMATION: humanized antibody

<400> SEQUENCE: 98

Cys Ile Tyr Gly Asp Ser Ser Asp Thr Leu Tyr Ala Asn Trp Ala Lys
1               5                   10                  15

Gly

<210> SEQ ID NO 99
<211> LENGTH: 18
<212> TYPE: PRT
<213> ORGANISM: Artificial Sequence
<220> FEATURE:
<223> OTHER INFORMATION: humanized antibody

<400> SEQUENCE: 99

Cys Ile Tyr Ala Gly Ser Ser Gly Ser Thr Tyr Tyr Ala Ser Trp Ala
1               5                   10                  15

Lys Gly

<210> SEQ ID NO 100
<211> LENGTH: 18
<212> TYPE: PRT
<213> ORGANISM: Artificial Sequence
<220> FEATURE:
<223> OTHER INFORMATION: humanized antibody

<400> SEQUENCE: 100

Cys Ile Tyr Ala Gly Ser Ser Val Ser Ile Tyr Tyr Ala Thr Trp Ala
1               5                   10                  15

Lys Gly

<210> SEQ ID NO 101
<211> LENGTH: 18
<212> TYPE: PRT
<213> ORGANISM: Artificial Sequence
<220> FEATURE:
<223> OTHER INFORMATION: humanized antibody

<400> SEQUENCE: 101

Cys Ile Tyr Thr Gly Asn Ser Asp Phe Thr Tyr Tyr Ala Asn Trp Ala
1               5                   10                  15

Lys Gly

<210> SEQ ID NO 102
<211> LENGTH: 17
<212> TYPE: PRT
<213> ORGANISM: Artificial Sequence
<220> FEATURE:
<223> OTHER INFORMATION: humanized antibody

<400> SEQUENCE: 102

Cys Ile Tyr Thr Gly Ser Gly Ser Thr Tyr Tyr Ala Asn Trp Ala Lys
1               5                   10                  15
```

Gly

<210> SEQ ID NO 103
<211> LENGTH: 8
<212> TYPE: PRT
<213> ORGANISM: Artificial Sequence
<220> FEATURE:
<223> OTHER INFORMATION: humanized antibody

<400> SEQUENCE: 103

Asp Pro Gly Tyr Ser Ser Trp Leu
1               5

<210> SEQ ID NO 104
<211> LENGTH: 11
<212> TYPE: PRT
<213> ORGANISM: Artificial Sequence
<220> FEATURE:
<223> OTHER INFORMATION: humanized antibody

<400> SEQUENCE: 104

Val Asp Ala Ser Ser Ser Gly Ser Trp Asp Leu
1               5                   10

<210> SEQ ID NO 105
<211> LENGTH: 15
<212> TYPE: PRT
<213> ORGANISM: Artificial Sequence
<220> FEATURE:
<223> OTHER INFORMATION: humanized antibody

<400> SEQUENCE: 105

Gly Gly Pro Gly Tyr Ser Thr Asn Thr His Tyr Ala Phe Asp Pro
1               5                   10                  15

<210> SEQ ID NO 106
<211> LENGTH: 11
<212> TYPE: PRT
<213> ORGANISM: Artificial Sequence
<220> FEATURE:
<223> OTHER INFORMATION: humanized antibody

<400> SEQUENCE: 106

Asp Arg Gly Thr Ser Thr Gly Ser Leu Asp Leu
1               5                   10

<210> SEQ ID NO 107
<211> LENGTH: 17
<212> TYPE: PRT
<213> ORGANISM: Artificial Sequence
<220> FEATURE:
<223> OTHER INFORMATION: humanized antibody

<400> SEQUENCE: 107

Thr His Tyr Ala Ala Val Ala Gly Tyr Gly Tyr Ala Ser Arg Leu Asp
1               5                   10                  15
Leu

<210> SEQ ID NO 108
<211> LENGTH: 10
<212> TYPE: PRT
<213> ORGANISM: Artificial Sequence
<220> FEATURE:
<223> OTHER INFORMATION: humanized antibody

<400> SEQUENCE: 108

```
Asp Leu Leu Val Val Thr Ser Phe Asn Leu
1               5                   10
```

<210> SEQ ID NO 109
<211> LENGTH: 9
<212> TYPE: PRT
<213> ORGANISM: Artificial Sequence
<220> FEATURE:
<223> OTHER INFORMATION: humanized antibody

<400> SEQUENCE: 109

```
Glu Thr Asp Gly Asn Tyr Phe Asn Leu
1               5
```

<210> SEQ ID NO 110
<211> LENGTH: 9
<212> TYPE: PRT
<213> ORGANISM: Artificial Sequence
<220> FEATURE:
<223> OTHER INFORMATION: humanized antibody

<400> SEQUENCE: 110

```
Gly Val Gly Phe Gly Tyr Phe Asn Leu
1               5
```

<210> SEQ ID NO 111
<211> LENGTH: 11
<212> TYPE: PRT
<213> ORGANISM: Artificial Sequence
<220> FEATURE:
<223> OTHER INFORMATION: humanized antibody

<400> SEQUENCE: 111

```
Ala Leu Gly Ser Ser Gly Tyr Arg Val Asn Leu
1               5                   10
```

<210> SEQ ID NO 112
<211> LENGTH: 7
<212> TYPE: PRT
<213> ORGANISM: Artificial Sequence
<220> FEATURE:
<223> OTHER INFORMATION: humanized antibody

<400> SEQUENCE: 112

```
Asp Pro Gln Tyr Phe Ile Leu
1               5
```

<210> SEQ ID NO 113
<211> LENGTH: 12
<212> TYPE: PRT
<213> ORGANISM: Artificial Sequence
<220> FEATURE:
<223> OTHER INFORMATION: humanized antibody

<400> SEQUENCE: 113

```
Leu Gln Gly Ala Asn Tyr Tyr Asn Ser Leu Ala Leu
1               5                   10
```

<210> SEQ ID NO 114
<211> LENGTH: 10
<212> TYPE: PRT
<213> ORGANISM: Artificial Sequence
<220> FEATURE:
<223> OTHER INFORMATION: humanized antibody

<400> SEQUENCE: 114

Asp Leu Asn Tyr Pro Asp Thr Ser Asn Leu
1               5                   10

<210> SEQ ID NO 115
<211> LENGTH: 9
<212> TYPE: PRT
<213> ORGANISM: Artificial Sequence
<220> FEATURE:
<223> OTHER INFORMATION: humanized antibody

<400> SEQUENCE: 115

Tyr Pro Gly Gly Ser Tyr Tyr Asn Leu
1               5

<210> SEQ ID NO 116
<211> LENGTH: 11
<212> TYPE: PRT
<213> ORGANISM: Artificial Sequence
<220> FEATURE:
<223> OTHER INFORMATION: humanized antibody

<400> SEQUENCE: 116

Val Asp Gly Ser Ser Ser Gly Ser Trp Asp Leu
1               5                   10

<210> SEQ ID NO 117
<211> LENGTH: 11
<212> TYPE: PRT
<213> ORGANISM: Artificial Sequence
<220> FEATURE:
<223> OTHER INFORMATION: humanized antibody

<400> SEQUENCE: 117

Ser Thr Gly Ser Val Gly Arg Gly Phe Asn Leu
1               5                   10

<210> SEQ ID NO 118
<211> LENGTH: 10
<212> TYPE: PRT
<213> ORGANISM: Artificial Sequence
<220> FEATURE:
<223> OTHER INFORMATION: humanized antibody

<400> SEQUENCE: 118

Phe Arg Asp Asp Tyr Ala Ser Leu Lys Leu
1               5                   10

<210> SEQ ID NO 119
<211> LENGTH: 10
<212> TYPE: PRT
<213> ORGANISM: Artificial Sequence
<220> FEATURE:
<223> OTHER INFORMATION: humanized antibody

<400> SEQUENCE: 119

Asn Ser Asn Asp Trp Met Tyr Phe Asn Leu
1               5                   10

<210> SEQ ID NO 120
<211> LENGTH: 11
<212> TYPE: PRT
<213> ORGANISM: Artificial Sequence
<220> FEATURE:
<223> OTHER INFORMATION: humanized antibody

<400> SEQUENCE: 120

Gln Ala Ser Glu Ser Ile Ser Asn Tyr Leu Ser

```
1               5                   10
```

<210> SEQ ID NO 121
<211> LENGTH: 11
<212> TYPE: PRT
<213> ORGANISM: Artificial Sequence
<220> FEATURE:
<223> OTHER INFORMATION: humanized antibody

<400> SEQUENCE: 121

```
Gln Ala Ser Glu Ser Ile Tyr Ser Asn Leu Ala
1               5                   10
```

<210> SEQ ID NO 122
<211> LENGTH: 11
<212> TYPE: PRT
<213> ORGANISM: Artificial Sequence
<220> FEATURE:
<223> OTHER INFORMATION: humanized antibody

<400> SEQUENCE: 122

```
Gln Ala Ser Gln Ser Ile Tyr Ile Tyr Leu Ser
1               5                   10
```

<210> SEQ ID NO 123
<211> LENGTH: 11
<212> TYPE: PRT
<213> ORGANISM: Artificial Sequence
<220> FEATURE:
<223> OTHER INFORMATION: humanized antibody

<400> SEQUENCE: 123

```
Gln Ala Ser Glu Asn Ile Gly Asn Gly Leu Ala
1               5                   10
```

<210> SEQ ID NO 124
<211> LENGTH: 11
<212> TYPE: PRT
<213> ORGANISM: Artificial Sequence
<220> FEATURE:
<223> OTHER INFORMATION: humanized antibody

<400> SEQUENCE: 124

```
Leu Ala Ser Glu Asp Ile Tyr Ser Gly Ile Ser
1               5                   10
```

<210> SEQ ID NO 125
<211> LENGTH: 11
<212> TYPE: PRT
<213> ORGANISM: Artificial Sequence
<220> FEATURE:
<223> OTHER INFORMATION: humanized antibody

<400> SEQUENCE: 125

```
Gln Ala Ser Glu Asp Ile Tyr Ser Asn Leu Ala
1               5                   10
```

<210> SEQ ID NO 126
<211> LENGTH: 11
<212> TYPE: PRT
<213> ORGANISM: Artificial Sequence
<220> FEATURE:
<223> OTHER INFORMATION: humanized antibody

<400> SEQUENCE: 126

```
Gln Ala Ser Glu Asp Ile Tyr Ser Asn Leu Ala
1               5                   10
```

```
<210> SEQ ID NO 127
<211> LENGTH: 11
<212> TYPE: PRT
<213> ORGANISM: Artificial Sequence
<220> FEATURE:
<223> OTHER INFORMATION: humanized antibody

<400> SEQUENCE: 127

Gln Ala Ser Glu Asp Ile Tyr Ser Asn Leu Ala
1               5                   10

<210> SEQ ID NO 128
<211> LENGTH: 11
<212> TYPE: PRT
<213> ORGANISM: Artificial Sequence
<220> FEATURE:
<223> OTHER INFORMATION: humanized antibody

<400> SEQUENCE: 128

Gln Ala Ser Glu Asn Ile Tyr Ser Ser Leu Ala
1               5                   10

<210> SEQ ID NO 129
<211> LENGTH: 13
<212> TYPE: PRT
<213> ORGANISM: Artificial Sequence
<220> FEATURE:
<223> OTHER INFORMATION: humanized antibody

<400> SEQUENCE: 129

Gln Ser Ser Gln Ser Val Asp Gly Asn Asn Leu Leu Ser
1               5                   10

<210> SEQ ID NO 130
<211> LENGTH: 11
<212> TYPE: PRT
<213> ORGANISM: Artificial Sequence
<220> FEATURE:
<223> OTHER INFORMATION: humanized antibody

<400> SEQUENCE: 130

Gln Ala Ser Gln Ser Ile Tyr Ser Phe Leu Ser
1               5                   10

<210> SEQ ID NO 131
<211> LENGTH: 11
<212> TYPE: PRT
<213> ORGANISM: Artificial Sequence
<220> FEATURE:
<223> OTHER INFORMATION: humanized antibody

<400> SEQUENCE: 131

Gln Ala Ser Gln Ser Ile Gly Tyr Tyr Leu Ala
1               5                   10

<210> SEQ ID NO 132
<211> LENGTH: 11
<212> TYPE: PRT
<213> ORGANISM: Artificial Sequence
<220> FEATURE:
<223> OTHER INFORMATION: humanized antibody

<400> SEQUENCE: 132

Gln Ala Ser Gln Thr Ile Ser Ile Asn Leu Ala
1               5                   10
```

<210> SEQ ID NO 133
<211> LENGTH: 11
<212> TYPE: PRT
<213> ORGANISM: Artificial Sequence
<220> FEATURE:
<223> OTHER INFORMATION: humanized antibody

<400> SEQUENCE: 133

Gln Ala Ser Gln Asn Ile Tyr Ser Asn Leu Ala
1               5                   10

<210> SEQ ID NO 134
<211> LENGTH: 13
<212> TYPE: PRT
<213> ORGANISM: Artificial Sequence
<220> FEATURE:
<223> OTHER INFORMATION: humanized antibody

<400> SEQUENCE: 134

Gln Ala Ser Gln Ser Val Tyr Asn Ser Asn His Leu Ser
1               5                   10

<210> SEQ ID NO 135
<211> LENGTH: 11
<212> TYPE: PRT
<213> ORGANISM: Artificial Sequence
<220> FEATURE:
<223> OTHER INFORMATION: humanized antibody

<400> SEQUENCE: 135

Gln Ala Ser Gln Ser Ile Ser Ser Tyr Leu Ser
1               5                   10

<210> SEQ ID NO 136
<211> LENGTH: 12
<212> TYPE: PRT
<213> ORGANISM: Artificial Sequence
<220> FEATURE:
<223> OTHER INFORMATION: humanized antibody

<400> SEQUENCE: 136

Gln Ala Ser Glu Ser Ile Ser Ala Asn Tyr Trp Ser
1               5                   10

<210> SEQ ID NO 137
<211> LENGTH: 7
<212> TYPE: PRT
<213> ORGANISM: Artificial Sequence
<220> FEATURE:
<223> OTHER INFORMATION: humanized antibody

<400> SEQUENCE: 137

Leu Ala Ser Thr Leu Ala Ser
1               5

<210> SEQ ID NO 138
<211> LENGTH: 7
<212> TYPE: PRT
<213> ORGANISM: Artificial Sequence
<220> FEATURE:
<223> OTHER INFORMATION: humanized antibody

<400> SEQUENCE: 138

Ala Ala Ser Leu Leu Ala Ser
1               5

```
<210> SEQ ID NO 139
<211> LENGTH: 7
<212> TYPE: PRT
<213> ORGANISM: Artificial Sequence
<220> FEATURE:
<223> OTHER INFORMATION: humanized antibody

<400> SEQUENCE: 139

Asp Ala Ser Lys Leu Ala Ser
1               5

<210> SEQ ID NO 140
<211> LENGTH: 7
<212> TYPE: PRT
<213> ORGANISM: Artificial Sequence
<220> FEATURE:
<223> OTHER INFORMATION: humanized antibody

<400> SEQUENCE: 140

Gly Ala Ser Thr Leu Ala Ser
1               5

<210> SEQ ID NO 141
<211> LENGTH: 7
<212> TYPE: PRT
<213> ORGANISM: Artificial Sequence
<220> FEATURE:
<223> OTHER INFORMATION: humanized antibody

<400> SEQUENCE: 141

Ala Ala Ser Asn Leu Glu Ser
1               5

<210> SEQ ID NO 142
<211> LENGTH: 7
<212> TYPE: PRT
<213> ORGANISM: Artificial Sequence
<220> FEATURE:
<223> OTHER INFORMATION: humanized antibody

<400> SEQUENCE: 142

Gly Ala Ser Thr Leu Ala Ser
1               5

<210> SEQ ID NO 143
<211> LENGTH: 7
<212> TYPE: PRT
<213> ORGANISM: Artificial Sequence
<220> FEATURE:
<223> OTHER INFORMATION: humanized antibody

<400> SEQUENCE: 143

Arg Ala Ser Thr Leu Ala Ser
1               5

<210> SEQ ID NO 144
<211> LENGTH: 7
<212> TYPE: PRT
<213> ORGANISM: Artificial Sequence
<220> FEATURE:
<223> OTHER INFORMATION: humanized antibody

<400> SEQUENCE: 144

Asp Ala Ser Thr Leu Ala Ser
1               5

<210> SEQ ID NO 145
```

```
<211> LENGTH: 7
<212> TYPE: PRT
<213> ORGANISM: Artificial Sequence
<220> FEATURE:
<223> OTHER INFORMATION: humanized antibody

<400> SEQUENCE: 145

Asp Ala Ser Asp Leu Ala Ser
1               5

<210> SEQ ID NO 146
<211> LENGTH: 7
<212> TYPE: PRT
<213> ORGANISM: Artificial Sequence
<220> FEATURE:
<223> OTHER INFORMATION: humanized antibody

<400> SEQUENCE: 146

Asp Ala Ser Asn Leu Ala Ser
1               5

<210> SEQ ID NO 147
<211> LENGTH: 7
<212> TYPE: PRT
<213> ORGANISM: Artificial Sequence
<220> FEATURE:
<223> OTHER INFORMATION: humanized antibody

<400> SEQUENCE: 147

Ala Ala Ser Asp Leu Glu Ser
1               5

<210> SEQ ID NO 148
<211> LENGTH: 7
<212> TYPE: PRT
<213> ORGANISM: Artificial Sequence
<220> FEATURE:
<223> OTHER INFORMATION: humanized antibody

<400> SEQUENCE: 148

Arg Ala Ser Thr Leu Ala Ser
1               5

<210> SEQ ID NO 149
<211> LENGTH: 7
<212> TYPE: PRT
<213> ORGANISM: Artificial Sequence
<220> FEATURE:
<223> OTHER INFORMATION: humanized antibody

<400> SEQUENCE: 149

Tyr Ala Ser Thr Leu Ala Ser
1               5

<210> SEQ ID NO 150
<211> LENGTH: 7
<212> TYPE: PRT
<213> ORGANISM: Artificial Sequence
<220> FEATURE:
<223> OTHER INFORMATION: humanized antibody

<400> SEQUENCE: 150

Ala Ala Ser Leu Leu Ala Ser
1               5

<210> SEQ ID NO 151
<211> LENGTH: 7
```

```
<212> TYPE: PRT
<213> ORGANISM: Artificial Sequence
<220> FEATURE:
<223> OTHER INFORMATION: humanized antibody

<400> SEQUENCE: 151

Ser Ala Ser Thr Leu Ala Ser
1               5

<210> SEQ ID NO 152
<211> LENGTH: 7
<212> TYPE: PRT
<213> ORGANISM: Artificial Sequence
<220> FEATURE:
<223> OTHER INFORMATION: humanized antibody

<400> SEQUENCE: 152

Gly Ala Ser Asn Leu Ala Ser
1               5

<210> SEQ ID NO 153
<211> LENGTH: 7
<212> TYPE: PRT
<213> ORGANISM: Artificial Sequence
<220> FEATURE:
<223> OTHER INFORMATION: humanized antibody

<400> SEQUENCE: 153

Gly Ala Ser Thr Leu Ala Ser
1               5

<210> SEQ ID NO 154
<211> LENGTH: 12
<212> TYPE: PRT
<213> ORGANISM: Artificial Sequence
<220> FEATURE:
<223> OTHER INFORMATION: humanized antibody

<400> SEQUENCE: 154

Gln Asn Trp Trp Val Ile Glu His Asn Gly Ala Ala
1               5                   10

<210> SEQ ID NO 155
<211> LENGTH: 12
<212> TYPE: PRT
<213> ORGANISM: Artificial Sequence
<220> FEATURE:
<223> OTHER INFORMATION: humanized antibody

<400> SEQUENCE: 155

Gln Ser Ala Ser Tyr Ser Thr Gly Pro Asp Trp Thr
1               5                   10

<210> SEQ ID NO 156
<211> LENGTH: 12
<212> TYPE: PRT
<213> ORGANISM: Artificial Sequence
<220> FEATURE:
<223> OTHER INFORMATION: humanized antibody

<400> SEQUENCE: 156

Gln Gln Gly Ala Thr Thr Tyr Asn Val Asp Asn Val
1               5                   10

<210> SEQ ID NO 157
<211> LENGTH: 13
<212> TYPE: PRT
```

```
<213> ORGANISM: Artificial Sequence
<220> FEATURE:
<223> OTHER INFORMATION: humanized antibody

<400> SEQUENCE: 157

Gln Cys Thr Tyr Trp Asn Pro Asp Tyr Ile Gly Gly Ala
1               5                   10

<210> SEQ ID NO 158
<211> LENGTH: 12
<212> TYPE: PRT
<213> ORGANISM: Artificial Sequence
<220> FEATURE:
<223> OTHER INFORMATION: humanized antibody

<400> SEQUENCE: 158

Leu Gly Gly Tyr Ser Tyr Ser Asn Thr Gly Pro Thr
1               5                   10

<210> SEQ ID NO 159
<211> LENGTH: 15
<212> TYPE: PRT
<213> ORGANISM: Artificial Sequence
<220> FEATURE:
<223> OTHER INFORMATION: humanized antibody

<400> SEQUENCE: 159

Leu Gly Val Cys Thr Asp Ile Ser Thr Asp Asp Leu Tyr Asn Ala
1               5                   10                  15

<210> SEQ ID NO 160
<211> LENGTH: 12
<212> TYPE: PRT
<213> ORGANISM: Artificial Sequence
<220> FEATURE:
<223> OTHER INFORMATION: humanized antibody

<400> SEQUENCE: 160

Leu Gly Val Tyr Thr Tyr Ser Thr Asp Ile His Ala
1               5                   10

<210> SEQ ID NO 161
<211> LENGTH: 12
<212> TYPE: PRT
<213> ORGANISM: Artificial Sequence
<220> FEATURE:
<223> OTHER INFORMATION: humanized antibody

<400> SEQUENCE: 161

Leu Gly Val Tyr Thr His Ile Ser Ala Asp Asn Ala
1               5                   10

<210> SEQ ID NO 162
<211> LENGTH: 13
<212> TYPE: PRT
<213> ORGANISM: Artificial Sequence
<220> FEATURE:
<223> OTHER INFORMATION: humanized antibody

<400> SEQUENCE: 162

Gln Gln Gly Tyr Tyr Ser Gly Gly Thr Asp Asn Asp Val
1               5                   10

<210> SEQ ID NO 163
<211> LENGTH: 12
<212> TYPE: PRT
<213> ORGANISM: Artificial Sequence
```

```
<220> FEATURE:
<223> OTHER INFORMATION: humanized antibody

<400> SEQUENCE: 163

Gln Gly Ser Tyr Tyr Ser Ser Trp Tyr Asn Val
1               5                   10

<210> SEQ ID NO 164
<211> LENGTH: 10
<212> TYPE: PRT
<213> ORGANISM: Artificial Sequence
<220> FEATURE:
<223> OTHER INFORMATION: humanized antibody

<400> SEQUENCE: 164

Gln Cys Asn Tyr Ile Ile Asp Tyr Gly Ala
1               5                   10

<210> SEQ ID NO 165
<211> LENGTH: 10
<212> TYPE: PRT
<213> ORGANISM: Artificial Sequence
<220> FEATURE:
<223> OTHER INFORMATION: humanized antibody

<400> SEQUENCE: 165

Gln Ser Tyr Tyr Asn Ser Asp Ser Asp Ala
1               5                   10

<210> SEQ ID NO 166
<211> LENGTH: 12
<212> TYPE: PRT
<213> ORGANISM: Artificial Sequence
<220> FEATURE:
<223> OTHER INFORMATION: humanized antibody

<400> SEQUENCE: 166

Gln Gln Gly Tyr Thr Glu Asp Asn Ile Asp Asn Thr
1               5                   10

<210> SEQ ID NO 167
<211> LENGTH: 12
<212> TYPE: PRT
<213> ORGANISM: Artificial Sequence
<220> FEATURE:
<223> OTHER INFORMATION: humanized antibody

<400> SEQUENCE: 167

Gln Gly Ala Val Tyr Ser Gly Asn Thr Glu Trp Ala
1               5                   10

<210> SEQ ID NO 168
<211> LENGTH: 13
<212> TYPE: PRT
<213> ORGANISM: Artificial Sequence
<220> FEATURE:
<223> OTHER INFORMATION: humanized antibody

<400> SEQUENCE: 168

Gln Gly Glu Phe Ser Cys Val Ser Ala Asp Cys Ile Ala
1               5                   10

<210> SEQ ID NO 169
<211> LENGTH: 12
<212> TYPE: PRT
<213> ORGANISM: Artificial Sequence
<220> FEATURE:
```

<223> OTHER INFORMATION: humanized antibody

<400> SEQUENCE: 169

```
Gln Cys Thr Tyr Tyr Asp Asn Asn Tyr Gly Gly Ala
1               5                   10
```

<210> SEQ ID NO 170
<211> LENGTH: 15
<212> TYPE: PRT
<213> ORGANISM: Artificial Sequence
<220> FEATURE:
<223> OTHER INFORMATION: humanized antibody

<400> SEQUENCE: 170

```
Gln Ser Trp Tyr Tyr Ser Gly Ser Gly Ser Tyr His Ser Trp Ala
1               5                   10                  15
```

<210> SEQ ID NO 171
<211> LENGTH: 107
<212> TYPE: PRT
<213> ORGANISM: Homo sapiens

<400> SEQUENCE: 171

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 172
<211> LENGTH: 329
<212> TYPE: PRT
<213> ORGANISM: Homo sapiens

<400> SEQUENCE: 172

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
```

```
              115                 120                 125
Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 173
<211> LENGTH: 123
<212> TYPE: PRT
<213> ORGANISM: Artificial Sequence
<220> FEATURE:
<223> OTHER INFORMATION: humanized antibody

<400> SEQUENCE: 173

Glu Val Gln Leu Leu Glu Ser Gly Gly Arg Leu Val Gln Pro Gly Thr
1               5                   10                  15

Ser Leu Arg Leu Ser Cys Ala Val Ser Gly Ile Asp Leu Ser Ser Tyr
            20                  25                  30

Ala Met Gly Trp Val Arg Gln Ala Pro Gly Lys Gly Leu Glu Tyr Val
        35                  40                  45

Gly Val Ile Thr Ser Ser Ala Thr Thr Tyr Tyr Ala Ser Trp Ala Lys
    50                  55                  60

Gly Arg Phe Thr Ile Ser Lys Thr Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Arg Gly Gly Pro Gly Tyr Ser Thr Asn Thr His Tyr Ala Phe Asp Pro
            100                 105                 110

Trp Gly Gln Gly Thr Leu Val Thr Val Ser Ser
        115                 120

<210> SEQ ID NO 174
<211> LENGTH: 108
<212> TYPE: PRT
```

```
<213> ORGANISM: Artificial Sequence
<220> FEATURE:
<223> OTHER INFORMATION: Humanized antibody

<400> SEQUENCE: 174

Asp Val Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Tyr Ser Phe
            20                  25                  30

Leu Ser Trp Tyr Gln Gln Lys Pro Gly Gln Ala Pro Lys Leu Leu Ile
        35                  40                  45

Tyr Ala Ala Ser Asp Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Asn Tyr Ile Ile Asp Tyr
                85                  90                  95

Gly Ala Phe Gly Gln Gly Thr Lys Val Val Ile Lys
            100                 105

<210> SEQ ID NO 175
<211> LENGTH: 10
<212> TYPE: PRT
<213> ORGANISM: Artificial Sequence
<220> FEATURE:
<223> OTHER INFORMATION: Humanized antibody

<400> SEQUENCE: 175

Gln Ser Asn Tyr Ile Ile Asp Tyr Gly Ala
1               5                   10
```

HUMANIZED ANTI-IL-1R3 ANTIBODIES

RELATED APPLICATIONS

This application is a divisional of U.S. patent application Ser. No. 16/099,059, filed Nov. 5, 2018, now U.S. Pat. No. 11,203,642, which is a 35 U.S.C. § 371 filing of International Patent Application No. PCT/EP2017/060925, filed May 8, 2017, which claims priority to European Patent Application No. 16168617.5, filed May 6, 2016, the entire disclosures of which are hereby incorporated herein by reference.

SEQUENCE LISTING

The instant application contains a Sequence Listing which has been submitted electronically in ASCII format and is hereby incorporated by reference in its entirety. Said ASCII copy, created on Jul. 28, 2021, is named 720826_SA9-298USCON_ST25.txt and is 102,478 bytes in size.

FIELD OF INVENTION

The present invention relates to humanized anti-IL-1R3 antibodies and the use thereof.

BACKGROUND

The interleukin 1 receptor accessory protein (IL1RAP), also called IL1R3, is a coreceptor of type 1 interleukin 1 receptor (IL1R1) and is indispensable for transmission of IL-1 signaling. Upon binding of IL-1, IL-1R1 associates with IL-1RAcP forming a functional signaling receptor complex, which stimulates NFkB activity.

IL-33, its receptor ST2, and IL-1RAcP form also a complex (IL-33/ST2/IL-1RAcP) with a similar activity in regard to NFkB activation as the IL-1β/IL-1R1/IL-1RAcP complex. IL-36 (IL-36α (IL-1F6), IL-36β (IL-1F8), and IL-36γ (IL-1F9)), their receptor IL-36R, and IL-1RAcP form also a complex (IL-36/Il-36R/IL-1RAcP) with a similar activity in regard to NFkB activation as the IL-1β/IL-1R1/IL-1RAcP complex.

Human NF-kB is an important regulator of expression of several genes involved in inflammation, immune response and apoptosis. Therefore, the dysfunction of NFkB is involved in the in the pathology of various diseases, including autoimmune diseases, neurodegenerative diseases, inflammation, and cancers. For example, in the treatment of osteoarthritis (OA), the NF-kB pathway is an important target. Thus, agents that regulate the human NFkB pathway via inhibiting the signaling activity of the human IL-1R1/IL-1RAcP complex represent possible treatments for various human diseases. In particular, high affinity neutralizing antibodies would make excellent therapeutic agents.

Since more than 15 years, attempts have been made to generate functional monoclonal antibodies against human IL1RAcP. However, many attempts failed and existing antibodies still exhibit various drawbacks. WO199623067 relates to an IL-1RAcP antibody, which binds specifically to murine IL-1 receptor accessory protein. Examples 15 and 16 describe the attempt to generate anti-human IL-1RAcP antibodies, which neutralize IL-1 biological activity. However, no such antibody is provided by WO199623067 and example 16, describing an IL-1 induced IL-6 assay is only hypothetical. Do-Young Yoon D-Y and Charles A. Dinarello C A describe in J. Immunol. 1998; 160:3170-3179 polyclonal antibodies to domains II and III of the murine IL-1RAcP which inhibit IL-1beta activity but not binding. However, at higher concentrations of IL-1beta (1000 pg/ml), this polyclonal antiserum did not block the proliferation of D10S cells. (D10S is a subclone of the murine D10.G4.1 helper T-cell which proliferates to subfemtomolar (attomolar) concentrations of IL-1 beta or alpha in the absence of mitogens, cf. Orencole S F and Dinarello C A; Cytokine 1 (1989) 14-22). Jaras M. et al., PNAS 107 (2010) 16280-16285 describe the use of rabbit polyclonal anti-IL1RAcP antibody KMT-1 for killing CML stems cell. This antibody induces ADCC in an IL1RAcP-independent manner caused by its rabbit Fc part. Jaras et al. expect that "potential future therapeutic IL1RAP-targeting antibodies are expected to show low toxicity on normal hematopoietic cells". Polyclonal rabbit antibodies against murine IL-1RAcP were also mentioned in Do-Young Yoon and Charles A. Dinarello, Journal of Biochemistry and Molecular Biology, Vol. 40, No. 4, July 2007, pp. 562-570.

WO2002064630 relates also to IL-1RAcP and its use, but no antibodies against IL-1RAcP are described. WO2004022718 and WO2009120903 mention theoretically that antibodies against CSF1R, IL13RA1, IL1RAP, IFNAR1, IL5R, INSR, IL1RL1, LTK, and TACSTD1 could be generated according to the state of the art. However, here also no antibody against IL-1RAcP is described. WO2011021014 and WO 2012098407 (US20140017167) relate to the polyclonal rabbit anti-human IL-1RAcP antiserum KMT-1 (see Jaras et al. 2010) and its use. WO2014100772 relates to an anti-IL-1RAcP antibody binding to IL-1RAcP. However, no activity in regard to inhibition of any functional signaling receptor complex (like IL-1β/IL-1R1/IL-1RAcP) which stimulates NFkB activity is described. U.S. Pat. No. 6,280,955 relates to IL-1RAcP and its use, but again no antibodies against IL-1RAcP are described. U.S. Pat. No. 7,390,880 mentions a N-terminal fragment of IL1RAcP, but describe also no antibodies against IL-1RAcP.

WO2004100987 relates to the use of an interleukin-I (IL-1) antagonist in the preparation of a medicament for the treatment of neointimal hyperplasia and to the use of an IL-1 antagonist for the treatment of neointimal hyperplasia. As such an antagonist an anti-IL-1RAcP antibody is suggested but not further described. US2003026806 relates to antibodies binding to IL-1. WO2002064630 relates also to an IL-1 antagonist ant to IL-1RAcP protein. Though to the use of IL-1RAcP for screening for IL-1RAcP antagonists are mentioned, no such method or antagonist is disclosed.

This shows that it has been exceedingly difficult to identify monoclonal antibodies with high affinity, high specificity, and potent neutralizing activity against IL-1R3. The present invention encompasses humanized IL-1R3 antibody, with high affinity and specificity for IL-1R 3, with potent IL-1R3 neutralizing activity 3, and improved stability.

SUMMARY OF INVENTION

The present invention relates to a humanized IgG1$_{LALA}$ antibody that specifically binds to IL-1R3 or a fragment or derivative thereof or a polypeptide that contains at least a portion of said antibody that is sufficient to confer IL-1R3 binding specificity. Said antibody inhibits IL-1R3 induced NFkB activity. It also inhibits IL-1alpha, IL-1beta, IL-33, and/or IL-36 stimulated NFkB activity.

The invention further relates to an antibody according to the invention for the use in treating a IL-1R3 mediated disease.

The invention further encompasses a method of treating an IL-1R3 mediated disease in a patient, comprising administering to a patient a pharmaceutically effective amount of said antibody.

The present invention also comprises a pharmaceutical composition comprising a pharmaceutically acceptable carrier and a therapeutically effective amount of said antibody.

Definitions

The term "rabbit" according to the invention means an animal of the members of the taxonomic order Lagomorpha, which includes the families (hares and rabbits) and Ochotonidae (pikas), preferably of genus Oryctolagus.

The term "antibody" encompasses the various forms of antibody structures including, but not being limited to, whole antibodies and antibody fragments as long as it shows the properties according to the invention.

The term "rabbit monoclonal antibody" according to the invention means a monoclonal antibody produced by immunizing a rabbit and isolated from a antigen producing cell of said rabbit as well as such an antibody which is further modified, preferably a humanized antibody, a chimeric antibody, a fragment thereof, or a further genetically engineered and recombinant produced antibody as long as the characteristic properties according to the invention are retained. Preferably the antibody is from a B cell or a rabbit hybridoma cell of said rabbit.

The term "antibody producing cell" according to the invention means a rabbit B cell which produce antibodies, preferably a B cell or rabbit hybridoma cell.

"Native antibodies" are usually heterotetrameric glycoproteins composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software.

The term "VL (or VH) region" has the same meaning as VL (or VH) domain.

The terms "Fc receptor" or "FcR" according to the invention refers to a human receptor that binds to the Fc region of an antibody. FcRs bind IgG antibodies and include receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daeron, Annu. Rev. Immunol. 15:203-234 (1997)). FcRIIIA (CD16a) mediates ADCC. FcRs are reviewed in Ravetch and Kinet, Annu. Rev. Immunol 9:457-92 (1991); Capel et al, Immunomethods 4:25-34 (1994); and de Haas et al, J. Lab. CHn. Med. 126:330-41 (1995). These and all other FcRs are encompassed by the term "FcR" herein. The term also includes the neonatal receptor, FcRn, which is responsible for the transfer of maternal IgGs to the fetus (Guyer et al, J. Immunol. 117:587 (1976) and Kim et al, J. Immunol. 24:249 (1994)) and mediates slower catabolism, thus longer half-life.

The term "antibody effector function(s)," or "effector function" as used herein refers to a function contributed by an Fc effector domain(s) of an IgG (e.g., the Fc region of an immunoglobulin). Such function can be effected by, for example, binding of an Fc effector domain(s) to an Fc receptor on an immune cell with phagocytic or lytic activity or by binding of an Fc effector domain(s) to components of the complement system. Typical effector functions are ADCC, ADCP and CDC.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

"Antibody-dependent cell-mediated cytotoxicity" and "ADCC" refer to a cell-mediated reaction in which nonspecific cytotoxic cells that express FcRs (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FCYRIII.

The term "Antibody-dependent cellular phagocytosis" and "ADCP" refer to a process by which antibody-coated cells are internalized, either in whole or in part, by phagocytic immune cells (e.g., macrophages, neutrophils and dendritic cells) that bind to an immunoglobulin Fc region.

C1q" is a polypeptide that includes a binding site for the Fc region of an immunoglobulin. C1q together with two serine proteases, C1r and C1s, forms the complex C1, the first component of the complement dependent cytotoxicity (CDC) pathway. Human C1q can be purchased commercially from, e.g. Quidel, San Diego, Calif.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgGi, $IgG_2$, $IgG_3$, $IgG_4$, IgAi, and IgA₂. The heavy chain constant domains that correspond to the different classes of immunoglobulins are called α, δ, ε, γ, and μ, respectively.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. Unless otherwise specified herein, numbering of amino acid residues in the Fc region or constant region is according to the EU numbering system, also called the EU index, as described in Kabat, et al., Sequences of Proteins of Immunological Interest, 5th Ed. Public Health Service, National Institutes of Health, Bethesda, MD (1991).

A "variant Fc region" comprises an amino acid sequence which differs from that of a "native" or "wildtype" sequence Fc region by virtue of at least one "amino acid modification" as herein defined. The term "Fc-variant" as used herein refers to a polypeptide comprising a modification in an Fc domain. The Fc variants of the present invention are defined according to the amino acid modifications that compose them. Thus, for example, P329G is an Fc variant with the substitution of proline with glycine at position 329 relative to the parent Fc polypeptide, wherein the numbering is according to the EU index. The identity of the wildtype amino acid may be unspecified, in which case the aforementioned variant is referred to as P329G. For all positions discussed in the present invention, numbering is according to the EU index. The EU index or EU index as in Kabat or EU numbering scheme refers to the numbering of the EU antibody (Edelman, et al., Proc Natl Acad Sci USA 63 (1969) 78-85, hereby entirely incorporated by reference.) The modification can be an addition, deletion, or substitution. Substitutions can include naturally occurring amino acids and non-naturally occurring amino acids. Variants may comprise non-natural amino acids. Examples include U.S. Pat. No. 6,586,207; WO 98/48032; WO 03/073238; US 2004/0214988 A1; WO 05/35727 A2; WO 05/74524 A2; Chin, J. W., et al., Journal of the American Chemical Society 124 (2002) 9026-9027; Chin, J. W., and Schultz, P. G., ChemBioChem 11 (2002) 1135-1137; Chin, J. W., et al., PICAS United States of America 99 (2002) 11020-11024; and, Wang, L., and Schultz, P. G., Chem. (2002) 1-10, all entirely incorporated by reference.

The term "Fc region-containing polypeptide" refers to a polypeptide, such as an antibody or immunoadhesin (see definitions below), which comprises an Fc region.

The terms "Fc receptor" or "FcR" are used to describe a receptor that binds to the Fc region of an antibody. A FcR which binds an IgG antibody (a gamma receptor) includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain, (see review in Daeron, M., Annu. Rev. Immunol. 15 (1997) 203-234). FcRs are reviewed in Ravetch, and Kinet, Annu. Rev. Immunol 9 (1991) 457-492; Capel, et al., Immunomethods 4 (1994) 25-34; and de Haas, et al., J. Lab. Clin. Med. 126 (1995) 330-41. Other FcRs, including those to be identified in the future, are encompassed by the term "FcR" herein. The term also includes the neonatal receptor, FcRn, which is responsible for the transfer of maternal IgGs to the fetus (Guyer, et al., J. Immunol. 117 (1976) 587 and Kim, et al., J. Immunol. 24 (1994) 249).

By "IgG Fc ligand" as used herein is meant a molecule, preferably a polypeptide, from any organism that binds to the Fc region of an IgG antibody to form an Fc/Fc ligand complex. Fc ligands include but are not limited to FcγRs, FcγRs, FcγRs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (Davis, et al., Immunological Reviews 190 (2002) 123-136, entirely incorporated by reference). Fc ligands may include undiscovered molecules that bind Fc. Particular IgG Fc ligands are FcRn and Fc gamma receptors. By "Fc ligand" as used herein is meant a molecule, preferably a polypeptide, from any organism that binds to the Fc region of an antibody to form an Fc/Fc ligand complex.

By "Fc gamma receptor", "FcγR" or "FcgammaR" as used herein is meant any member of the family of proteins that bind the IgG antibody Fc region and is encoded by an FcγR gene. In humans this family includes but is not limited to FcγRI (CD64), including isoforms FcγRIA, FcγRIB, and FcγRIC; FcγRII (CD32), including isoforms FcγRIIA (including allotypes H131 and R131), FcγRIIB (including FcγRIIB-1 and FcγRIIB-2), and FcγRIIc; and FcγRIII (CD 16), including isoforms FcγRIIIA (including allotypes VI 58 and F158) and FcγRIIIb (including allotypes FcγRIIB-NA1 and FcγRIIB-NA2) (Jefferis, et al., Immunol Lett 82 (2002) 57-65, entirely incorporated by reference), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD 16), and FCYRIII-2 (CD 16-2), as well as any undiscovered mouse FcγRs or FcγR isoforms or allotypes.

By "FcRn" or "neonatal Fc Receptor" as used herein is meant a protein that binds the IgG antibody Fc region and is encoded at least in part by an FcRn gene. The FcRn may be from any organism, including but not limited to humans, mice, rats, rabbits, and monkeys. As is known in the art, the functional FcRn protein comprises two polypeptides, often referred to as the heavy chain and light chain. The light chain is beta-2-microglobulin and the heavy chain is encoded by the FcRn gene. Unless otherwise noted herein, FcRn or an FcRn protein refers to the complex of FcRn heavy chain with beta-2-microglobulin.

An "immunoconjugate" means an antibody conjugated to one or more cytotoxic agents, such as a chemotherapeutic agent, a drug, a growth inhibitory agent, a toxin, another antibody or a radioactive isotope.

"Antibody fragments" comprise a portion of a full length antibody, preferably the variable regions thereof, or at least the antigen binding site thereof. Examples of antibody fragments include diabodies, Fab fragments, and single-chain antibody molecules. scFv antibodies are, e.g., described in Huston, J. S., Methods in Enzymol. 203 (1991) 46-88.

The terms "monoclonal antibody" or "monoclonal antibody composition" as used herein refer to a preparation of antibody molecules of a single amino acid composition.

The term "humanized antibody" or "humanized version of an antibody" refers to antibodies in which a human variable region has been modified to comprise the CDRs of an antibody according to the invention. In a preferred embodiment, the CDRs of the VH and VL are grafted into the framework region of human antibody to prepare the "humanized antibody." See e.g. Riechmann, L., et al, Nature 332 (1988) 323-327; and Neuberger, M. S., et al, Nature 314 (1985) 268-270. The heavy and light chain variable framework regions can be derived from the same or different human antibody sequences. The human antibody sequences can be the sequences of naturally occurring human antibodies. Human heavy and light chain variable framework regions are listed e.g. in Lefranc, M.-P., Current Protocols in Immunology (2000)—Appendix IP A.1P.1-A.1P.37 and are accessible via IMGT, the international ImMunoGeneTics information System® (http://imgt.cines.fr) or via http://vbase.mrc-cpe.cam.ac.uk.

The terms "specifically binding, against target, or anti-target antibody", as used herein, refer to binding of the antibody to the respective antigen (target), measured by ELISA, wherein said ELISA preferably comprises coating the respective antigen to a solid support, adding said antibody under conditions to allow the formation of an immune complex with the respective antigen or protein, detecting said immune complex by measuring the Optical Density values (OD) using a secondary antibody binding to an antibody according to the invention and using a peroxidase-mediated color development.

The term "antigen" according to the invention refers to the antigen used for immunization or a protein comprising said antigen as part of its protein sequence. For example, for immunization a fragment of the extracellular domain of a protein (e.g. the first 20 amino acids) can be used and for detection/assay and the like the extracellular domain of the protein or the full length protein can be used.

The term "specifically binding" or "specifically recognized" herein means that an antibody exhibits appreciable affinity for an antigen and, preferably, does not exhibit significant cross-reactivity.

"Appreciable" binding affinity includes binding with an affinity of at least $10\exp 7 M^{-1}$, specifically at least $10\exp 8 M^{-1}$, more specifically at least $10\exp 9 M^{-1}$, or even more specifically at least $10\exp 10 M^{-1}$.

An antibody that "does not exhibit significant cross-reactivity" is one that will not appreciably bind to an undesirable other protein. An antibody specific for an epitope according to the invention will, for example, not significantly cross-react with other epitopes on IL-1R3. Specific binding can be determined according to any art-recognized means for determining such binding, e.g. by competitive binding assays (e.g. ELISA).

All protein terms as used herein refers to the human proteins. If a protein from another species is meant, this is explicitly mentioned.

The term "IL-1alpha", as used herein, refers to human IL-1 (UniProtKB P01583). The term "IL-1beta", as used herein, refer to human IL-1beta (UniProtKB P01584). IL-1 stimulates thymocyte proliferation by inducing IL-2 release, B-cell maturation and proliferation, and fibroblast growth factor activity. IL-1 proteins are involved in the inflammatory response, being identified as endogenous pyrogens (UniProtKB).

The term "IL-33", as used herein, refers to human IL-33 (UniProtKB 095760), a cytokine that binds to and signals through the IL1RL1/ST2 receptor which in turn activates NF-kappa-B and MAPK signaling pathways in target cells (UniProtKB).

The term "IL-36", as used herein, refers to human IL-36alpha (UniProtKB Q9UHA7, IL-36beta (UniProtKB Q9NZH7) and or IL-36gamma (UniProtKB Q9NZH8). IL-36 are cytokines that bind to and signal through the IL1RL2/IL-36R receptor which in turn activates NF-kappa-B and MAPK signaling pathways in target cells linked to a pro-inflammatory response. IL-36 seems to be involved in skin inflammatory response by acting on keratinocytes, dendritic cells and indirectly on T cells to drive tissue infiltration, cell maturation and cell proliferation (UniProtKB).

The term "NFkB" as used herein, refer to human nuclear factor NF-kappa-B, which consists of p105 subunit (P19838) and p100 subunit (Q00653).

"Inhibition of NFkB" is measured according to the invention as inhibition of NFkB dependent luciferase gene expression in human cells. Such methods are e.g. described in Windheim M. et al., Mol. Cell. Biol. 28 (2008) 1783-1791; Huang J. et al. PNAS USA 94 (1997) 12829-12832; Xiaoxia L. et al., Mol. Cell, Biol. 19 (1999) 4643-4652. If murine NFkB is meant herein it is explicitly mentioned.

The "variable region (or domain) of an antibody according to the invention" (variable region of a light chain (VL), variable region of a heavy chain (VH)) as used herein denotes each of the pair of light and heavy chain regions which are involved directly in binding the antibody to the antigen. The variable light and heavy chain regions have the same general structure and each region comprises four framework (FR) regions whose sequences are widely conserved, connected by three complementary determining regions, CDRs. The antibody according to the invention comprises a VH region and a VL region or parts thereof, which are both together sufficient for the specific binding to the respective antigen.

The term "antigen-binding portion of an antibody" when used herein refer to the amino acid residues of an antibody which are responsible for antigen-binding. The antigen-binding portion of an antibody comprises preferably amino acid residues from the "complementary determining regions" or "CDRs". The CDR sequences are defined according to Kabat et al, Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable region.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

The term "cancer" as used herein may be, for example, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, lymphoma, lymphocytic leukemia, including refractory versions of any of the above cancers, or a combination of one or more of the above cancers.

DETAILED DESCRIPTION OF THE INVENTION

The humanization of antibodies that originate from immunized mammals is required as quality feature in development, when said antibodies are meant for use as human therapeutics. Goal of the humanization is to keep the original characteristics (binding specificity, activity) of the antibody as far as possible, while reducing the immunological side effects that may occur when introducing non-humanized antibodies derived from other organisms, into humans. The present invention is based on the known humanization strategy of CDR grafting. Here, a large amount of active humanized antibodies was produced in parallel and top candidates were chosen for further assessment.

As outlined in the introduction of this application, it is exceedingly difficult to identify monoclonal antibodies with high affinity, high specificity, and potent neutralizing activity against IL-1R3. The present invention encompasses humanized IL-1R3 antibody, with high affinity and specificity for IL-1R 3, with potent IL-1R3 neutralizing activity 3, and improved stability.

In particular, the present invention relates to humanized antibody that specifically binds to IL-1R3 or a fragment or derivative thereof that contains at least a portion of said antibody that is sufficient to confer IL-1R3 binding specificity, comprising:
a) a heavy chain variable region (VH) comprising the complementary determining regions comprising CDR-H1, CDR-H2, and CDR-H3
wherein the CDR-H1 region comprises an amino acid sequence selected from the group of SEQ ID NO: 69-85,
wherein the CDR-H2 region comprises an amino acid sequence selected from the group of SEQ ID NO: 86-102,
and wherein the CDR-H3 region comprises an amino acid sequence selected from the group of SEQ ID NO: 103-119; and
b) a light chain variable region (VL) comprising the complementary determining regions comprising CDR-L1, CDR-L2, and CDR-L3
wherein the CDR-L1 region comprises an amino acid sequence selected from the group of SEQ ID NO: 120-136,
wherein the CDR-L2 region comprises an amino acid sequence selected from the group of SEQ ID NO: 137-153, and
wherein the CDR-L3 region comprises an amino acid sequence selected from the group of SEQ ID NO: 154-170 and 175.

In one embodiment, the antibody of the invention comprises a substitution at position 2 of CDR-L3. Said substitution may be a cysteine to serine substitution.

Moreover, the present invention encompasses a humanized antibody that specifically binds to IL-1R3 or a fragment or derivative thereof that contains at least a portion of said antibody that is sufficient to confer IL-1R3 binding specificity, wherein the antibody comprises a heavy chain variable (VH) region that is least 60% identical, preferably at least 70% identical, more preferably at least 80% identical, more preferably at least 90% identical to a VH region selected from the group consisting of VH regions of SEQ ID NO: 1 to 34 and SEQ ID NO:173.

In one embodiment, the humanized antibody that specifically binds to IL-1R3 or a fragment or derivative thereof that contains at least a portion of said antibody that is sufficient to confer IL-1R3 binding specificity, comprises a heavy chain variable region (VH) sequence having at least 90%, 91%, 92%, 93%, 94%, 95%, 96%, 97%, 98%, 99%, or 100% sequence identity to an amino acid sequence selected from the group of VH sequences according to the invention.

In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, whereby the antibody retains the ability to bind specifically according to the invention to the respective antigen.

The present invention also relates to a humanized antibody that specifically binds to IL-1R3 or a fragment or derivative thereof that contains at least a portion of said antibody that is sufficient to confer IL-1R3 binding specificity, wherein the antibody comprises a light chain variable (VL) region that is least 60% identical, preferably at least 70% identical, more preferably at least 80% identical, more preferably at least 90% identical to a VL region selected from the group consisting of VL regions of SEQ ID NO: 35 to 68 and 174.

In another embodiment the humanized antibody that specifically binds to IL-1R3 or a fragment or derivative thereof that contains at least a portion of said antibody that is sufficient to confer IL-1R3 binding specificity, comprises a light chain variable region (VL) having at least 90%, 91%, 92%, 93%, 94%, 95%, 96%, 97%, 98%, 99%, or 100% sequence identity to the amino acid sequence of the VL sequences according to the invention.

In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, whereby the antibody retains the ability to bind specifically to the respective antigen.

In certain embodiments, a total of 1 to 10 amino acids have been substituted, inserted and/or deleted in said VL sequences. In certain embodiments, the substitutions, insertions, or deletions occur in regions outside the CDRs (i.e., in the FRs). The invention also comprises affinity matured antibodies which can be produced according to methods known in the art. Marks et al. Bio/Technology 10:779-783 (1992) describes affinity maturation by VH and VL domain shuffling. Random mutagenesis of CDR and/or framework residues is described by: Barbas et al., Proc Nat. Acad. Sci, USA 91: 3809-3813 (1994); Schier et al., Gene 169: 147-155 (1995); Yelton et al., J. Immunol. 1 55: 1994-2004

(1995); Jackson et al., J. Immunol. 1 54(7):3310-9 (1995); and Hawkins et al., J. Mol. Biol. 226:889-896 (1992) and WO2010108127.

In certain embodiments, a total of 1 to 10 amino acids have been substituted, inserted and/or deleted in each of said VH or VL sequences. In one embodiment, the antibody of the invention comprises a substitution at position 90 of the VH or VL sequence. It is preferred that the amino acid at position 90 is substituted by a serine. This substitution is preferably at position 90 of the light chain variable region (VL). In a preferred embodiment, the cysteine at position 90 of SEQ ID. NO: 62 is substituted by a serine. However, the antibodies of this invention are not limited to an amino acid substitution at position 90 but may comprise any substitution, deletion or insertion that leads to a functional antibody possessing the properties of the antibodies of this invention.

Therefore, the VL and VH sequences of the antibodies of this invention may also comprise further mutations at different positions.

In certain embodiments, substitutions, insertions, or deletions occur in regions outside the CDRs (i.e., in the FRs).

In other embodiments, the substitutions, insertions, or deletions occur in regions inside the CDRs. In one preferred embodiment, the antibody of the invention comprises a substitution at position 2 of CDR-L3. It is preferred that this substitution is cysteine to serine. In one embodiment, said substitution is in SEQ ID NO: 164.

The present invention also encompasses a humanized antibody that specifically binds to IL-1R3 or a fragment or derivative thereof that contains at least a portion of said antibody that is sufficient to confer IL-1R3 binding specificity, wherein the antibody comprises a heavy chain variable region (VH) comprising an amino acid sequence selected from the group of SEQ ID NO: 1 to 34 and 173.

Preferably, the heavy chain variable region (VH) sequence is SEQ ID NO:1, alternatively SEQ ID NO:2, or SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, or SEQ ID NO:29, SEQ ID NO:30, SEQ ID NO:31, SEQ ID NO:32, SEQ ID NO:33, or alternatively SEQ ID NO:34 or 173.

Furthermore, the invention relates to a humanized antibody that specifically binds to IL-1R3 or a fragment or derivative thereof that contains at least a portion of said antibody that is sufficient to confer IL-1R3 binding specificity, wherein the antibody comprises a light chain variable region (VL) comprising an amino acid sequence selected from the group of SEQ ID NO: 35 to 68 and 174.

Even more preferred, the light chain variable region (VL) sequence is SEQ ID NO:35, or SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, or alternatively SEQ ID NO:68 or 174.

The humanized antibody according to the invention that specifically binds to IL-1R3 or a fragment or derivative thereof that contains at least a portion of said antibody that is sufficient to confer IL-1R3 binding specificity, also comprises a VH region and a VL region comprising the respective CDR1, CDR2 and CDR3 regions of an antibody selected from the group consisting of MAB-15-0139, MAB-15-0106MAB-15-0108, MAB-15-0110, MAB-15-0117, MAB-15-0121, MAB-15-0140, MAB-15-0115, MAB-15-0125, MAB-15-0119, MAB-15-0109, MAB-15-0097, MAB-15-0135, MAB-15-0133, MAB-15-0107, MAB-15-0128, MAB-15-0116, MAB-16-0004, MAB-16-0009, MAB-16-0028, MAB-16-0031, MAB-16-0043, MAB-16-0049, MAB-16-0045, MAB-16-0040, MAB-16-0036, MAB-16-0046, MAB-16-0030, MAB-16-0021, MAB-16-0019, MAB-16-0015, MAB-16-0027, MAB-16-0048, MAB-16-0041, MAB-16-0149, MAB-16-0150.

In one embodiment, the humanized antibody that specifically binds to IL-1R3 or a fragment or derivative thereof that contains at least a portion of said antibody that is sufficient to confer IL-1R3 binding specificity, comprises SEQ ID NO.: 1 and 35, or SEQ ID NO.: 2 and 36. An antibody according to the invention may also comprise SEQ ID NO.: 3 and 37, or SEQ ID NO.: 4 and 38, or SEQ ID NO.: 5 and 39, or SEQ ID NO.: 6 and 40, or SEQ ID NO.: 7 and 41, or SEQ ID NO.: 8 and 42, or SEQ ID NO.: 9 and 43, or SEQ ID NO.: 10 and 44, or SEQ ID NO.: 11 and 45, or SEQ ID NO.: 12 and 46. Alternatively, an antibody according to the invention comprises SEQ ID NO.: 13 and 47, or SEQ ID NO.: 14 and 48, or SEQ ID NO.: 15 and 49, or SEQ ID NO.: 16 and 50, or SEQ ID NO.: 17 and 51, or SEQ ID NO.: 18 and 52, or SEQ ID NO.: 19 and 53, or SEQ ID NO.: 20 and 54, or SEQ ID NO.: 21 and 55, or SEQ ID NO.: 22 and 56, or SEQ ID NO.: 23 and 57, or SEQ ID NO.: 24 and 58, or SEQ ID NO.: 25 and 59, or SEQ ID NO.: 26 and 60, or SEQ ID NO.: 27 and 61.

Alternatively, an antibody according to the invention comprises SEQ ID NO.: 28 and 62, or SEQ ID NO.: 29 and 63, or SEQ ID NO.: 30 and 64, or SEQ ID NO.: 31 and 65, or SEQ ID NO.: 32 and 66, or SEQ ID NO.: 33 and 67, or SEQ ID NO.: 34 and 68.

Most preferably, the humanized antibody that specifically binds to IL-1R3 or a fragment or derivative thereof that contains at least a portion of said antibody that is sufficient to confer IL-1R3 binding specificity comprises the constant region sequences CR-H (SEQ ID NO. 172) and CR-L (SEQ ID NO. 171) and a VH region selected from the group of SEQ ID NO: 1 to 34 and 173 and a VL region selected from the group of SEQ ID NO: 35 to 68 and 174.

The humanized antibody that specifically binds to IL-1R3 or a fragment or derivative thereof that contains at least a portion of said antibody that is sufficient to confer IL-1R3 binding specificity, also comprises the constant region sequences CR-H (SEQ ID NO. 172) and CR-L (SEQ ID NO. 171) and a VH region and a VL region comprising the respective CDR1, CDR2 and CDR3 regions of an antibody selected from the group consisting of MAB-15-0139, MAB-15-0106, MAB-15-0108, MAB-15-0110, MAB-15-0117, MAB-15-0121, MAB-15-0140, MAB-15-0115, MAB-15-0125, MAB-15-0119, MAB-15-0109, MAB-15-0097, MAB-15-0135, MAB-15-0133, MAB-15-0107, MAB-15-0128, MAB-15-0116, MAB-16-0004, MAB-16-0009, MAB-16-0028, MAB-16-0031, MAB-16-0043, MAB-16-0049, MAB-16-0045, MAB-16-0040, MAB-16-0036, MAB-16-0046, MAB-16-0030, MAB-16-0021, MAB-16-0019, MAB-16-0015, MAB-16-0027, MAB-16-0048, MAB-16-0041, MAB-16-0149 and MAB-16-0150.

According to the preferred therapeutic application of the antibodies according to the invention, the effector functions (such as ADCC) of the antibodies of the invention are reduced or lacking. In contrast to other antibodies of prior art, such as CAN04 (e.g. WO 2015/132602 A1), the antibodies of the invention do not exhibit increased effector functions and do not include ADCC.

Preferably, the humanized antibodies according to the invention show reduced or no Fcγ-receptor signaling.

Therefore, the invention also relates to a humanized antibody, wherein said antibody comprises at least amino acid substitutions at L234A and L235A of the human IgG1 Fc region or S228P and L235E of the human IgG4 Fc region.

In one embodiment according to the invention, the antibody is a humanized IgG1$_{LALA}$ antibody.

In one embodiment according to the invention, a humanized antibody that specifically binds to IL-1R3 or a fragment or derivative thereof that contains at least a portion of said antibody that is sufficient to confer IL-1R3 binding specificity, inhibits IL-1R3 induced NFkB activity.

In another embodiment, the humanized antibody that specifically binds to IL-1R3 or a fragment or derivative thereof that contains at least a portion of said antibody that is sufficient to confer IL-1R3 binding specificity, binds to the same epitope as an antibody selected from the group of antibodies MAB-15-0139, MAB-15-0106, MAB-15-0108, MAB-15-0110, MAB-15-0117, MAB-15-0121, MAB-15-0140, MAB-15-0115, MAB-15-0125, MAB-15-0119, MAB-15-0109, MAB-15-0097, MAB-15-0135, MAB-15-0133, MAB-15-0107, MAB-15-0128, MAB-15-0116, MAB-16-0004, MAB-16-0009, MAB-16-0028, MAB-16-0031, MAB-16-0043, MAB-16-0049, MAB-16-0045, MAB-16-0040, MAB-16-0036, MAB-16-0046, MAB-16-0030, MAB-16-0021, MAB-16-0019, MAB-16-0015, MAB-16-0027, MAB-16-0048, MAB-16-0041, MAB-16-0149 and MAB-16-150.

The antibodies according to the invention have the advantage to be very potent when it comes to binding to their target. They exhibit a strong binding capacity to their antigen, IL1R3, but not to other receptors. The binding properties of the antibodies were studied in biochemical enzyme-linked immunosorbent assays (ELISA) and cell binding analysis (flow cytometry) and are exemplified in FIGS. 2, 6 and 7.

Preferred antibodies according to the invention, show a half maximal effective concentration (EC50) of less than 30 ng/ml, preferably of less than 20 ng/ml. In other embodiments, they show an EC50 of less than 15 ng/ml, 10 ng/ml or of less than 5 ng/ml. A preferred antibody according to the invention shows an EC50 of 16.3 ng/ml in a biochemical ELISA experiment (cf. FIG. 7).

The antibodies according to the invention also show a very strong binding to their antigen in experiments in which human IL1R3 is expressed in different cell lines while the antibodies do not bind cell lines not expressing human IL1R3 (e.g. NIH-3T3, cf. FIG. 5).

In the IL1R3 high-expressing cell line SK-MEL-30 (cf. FIG. 6, Example 8) the antibodies exhibit an EC50 of preferably less than 400 ng/ml, more preferably less than 350 ng/ml, or less than 310 ng/ml.

In one preferred embodiment encompassed by the invention, the antibody according to the invention inhibits IL-1alpha and/or IL-1beta stimulated NFkB activity. FIGS. 3, 4 and 8 exemplify the strong inhibitory activity of the antibodies according to the invention.

In one embodiment, the humanized antibody that specifically binds to IL-1R3 or a fragment or derivative thereof that contains at least a portion of said antibody that is sufficient to confer IL-1R3 binding specificity, inhibits IL-1 alpha stimulated NFkB activity.

In another embodiment, the humanized antibody that specifically binds to IL-1R3 or a fragment or derivative thereof that contains at least a portion of said antibody that is sufficient to confer IL-1R3 binding specificity inhibits IL-1beta stimulated NFkB activity.

It is preferred that an antibody according to the invention inhibits IL-1beta stimulated NFkB activity in HEK293T/17-FR cells with an EC50 of less than 100 ng/ml, preferably of less than 95 ng/ml, 85 ng/ml, 75 ng/ml, 65 ng/ml, 55 ng/ml, 45 ng/ml, 35 ng/ml, 25 ng/ml, 20 ng/ml and most preferred of less than 15 ng/ml (e.g. cf. FIG. 3).

It is further preferred that an antibody according to the invention inhibits IL-1alpha stimulated NFkB activity with an EC50 of less than 1000 ng/ml, preferably of less than 500 ng/ml, 300 ng/ml, 200 ng/ml, and most preferred of less than 100 ng/ml (e.g. cf. FIG. 8) in A549-NFkB-RE-Luc cells.

It is further preferred that an antibody according to the invention inhibits IL-1beta stimulated NFkB activity with an EC50 of less than 700 ng/ml, preferably of less than 600 ng/ml, 300 ng/ml, 200 ng/ml, 100 ng/ml and most preferred of less than 50 ng/ml in A549-NFkB-RE-Luc cells (e.g. cf. FIG. 8).

The invention also encompasses a humanized antibody, wherein said antibody inhibits NFkB activity stimulated by a complex selected from the group consisting of IL-1β/IL-1R1/IL-1RAcP, IL-1a/IL-1R1/IL-1RAcP IL-33/ST2/IL-1RAcP, and/or IL-36/Il-36R/IL-1RAcP.

Moreover, a humanized antibody according to invention inhibits in a concentration of 10 µg/ml (rabbit IgG isotype has a molecular weight of 150 KD) NFkB expression in A549-NFkB-RE-Luc cell lysates (Steady-Glo™ Luciferase Assay System; Promega; Cat. No. E2510) stimulated with 0.1 ng/ml human IL-1alpha, human IL-1beta, IL-33 and/or IL-36 (molecular weight see UniProtKB/Swiss-Prot), for 50% or more, preferably for 70% or more, preferably for 80% or more preferably for 90% and more, and more preferably for 95% or more, related to the same assay without said antibody according to the invention.

In one embodiment, the humanized antibody according to the invention inhibits IL-1alpha, IL-1beta, IL-33, and/or IL-36, respectively, stimulated luciferase activity in HEK 293T/17 cells (HEK 293T/17-FR cells transfected with luciferase under control of NF-kB reporter gene), HEK-Blue-IL33™ cells (Invivogen) or HEK-293/17-IF cells.

Preferably, said IL-1alpha, stimulated luciferase activity is inhibited by 50% or more, preferably by 70% or more, preferably by 80% or more, preferably by 90% and more, and more preferably by 95% or more. Preferably, said IL-1alpha, stimulated luciferase activity is inhibited by 95%.

Preferably, said IL-1beta, stimulated luciferase activity is inhibited by 50% or more, preferably by 70% or more, preferably by 80% or more, preferably by 90% and more, and more preferably by 95% or more. Preferably, said IL-1beta, stimulated luciferase activity is inhibited by 95%.

Preferably, said IL-33, stimulated luciferase activity is inhibited by 50% or more, preferably by 70% or more, preferably by 80% or more, preferably by 90% and more, and more preferably by 95% or more. Preferably, said IL-33, stimulated luciferase activity is inhibited by 95%.

Preferably, said IL-36, stimulated luciferase activity is inhibited by 50% or more, preferably by 70% or more, preferably by 80% or more, preferably by 90% and more, and more preferably by 95% or more. Preferably, said IL-36, stimulated luciferase activity is inhibited by 95%.

Furthermore, the antibodies according to the invention inhibit human IL-1a and IL-1b mediated IL-6 release and are superior to polyclonal antibodies. This potent inhibitory activity is shown and exemplified in FIG. 9. In these experiments, the EC50 values demonstrate that humanized anti-IL-1R3 IgG1-LALA antibodies are superior to that of goat-anti-human-IL1-R3 polyclonal antibody AF676 (R&D Systems). In preferred embodiments of the invention, the antibodies inhibit human IL-a mediated IL-6 release with an EC50 of less than 2500 ng/ml, preferably of less than 1500 ng/ml, less than 1000 ng/ml, less than 600 ng/ml, less than 400 ng/ml, or less than 300 ng/ml. It is also preferred that the antibodies of the invention inhibit human IL-1b mediated IL-6 release with an EC50 of less than 500 ng/ml, preferably of less than 400 ng/ml, less than 300 ng/ml, less than 200 ng/ml, or less than 150 ng/ml.

In another embodiment according to the invention, the antibodies inhibit human IL-33 mediated NfkB-signaling. FIG. 10 exemplifies the inhibitory activity of selected antibodies according to the invention in HEK-Blue-IL33™ cells and demonstrates the superiority over polyclonal antibodies. In preferred embodiments of the invention, the antibodies inhibit human IL-33 mediated NfkB-signaling with an EC50 of less than 20000 ng/ml, preferably of less than 18000 ng/ml, less than 3000 ng/ml, less than 1000 ng/ml, less than 500 ng/ml, or less than 400 ng/ml.

The antibodies of the invention may also inhibit human IL-36 mediated NfkB-signaling (FIG. 11). Preferably, they inhibit human IL-36 mediated NfkB-signaling at an EC50 of less than 100 ng/ml, preferably at less than 50 ng/ml, less than 40 ng/ml, less than 30 ng/ml, less than 20 ng/ml, or less than 15 ng/ml.

Strikingly, the inventors found that the antibodies according to the invention inhibit cytokine release mediated by various different stimuli. For example, the antibodies inhibit cytokine release mediated by IL-1a, IL-33 and IL-36a. Results of a selected antibody are shown in FIG. 12. For example, the antibody MAB-16-0030 inhibits cytokine release mediated by all three stimuli, while IL-1Ra affects only IL-1a mediated cytokine release.

Diseases associated with acute or chronic inflammation are maintained or establish by the action of multiple cytokines either at the same time or consecutively. Early "alarmins" such as IL-1a and IL-33 may trigger other cytokines including IL-1b and IL-36 to establish a strong inflammatory environment. Therefore, the concomitant inhibition of signaling mediated by multiple cytokines exerts efficacious control of inflammatory processes. It is a key aspect of the antibodies of the invention that they inhibit multi-cytokine signaling via the blockage of the IL1R3 receptor.

Binding of antibodies to immune cells may result in cell depleting and deleterious effects, e.g. by direct induction of apoptotic signaling pathways, stimulation of excessive cytokine release or antibody effector function mediated antibody dependent cellular cytotoxicity antibody (ADCC).

Accordingly, it is one further aspect of the antibodies of the invention that they do not induce immune cell depletion, mediated by direct induction of apoptotic signaling pathways, stimulation of excessive cytokine release or antibody effector function mediated antibody dependent cellular cytotoxicity.

Importantly, the antibodies according to the invention do not affect the viability of immune cells. For example, they do not affect the viability of human peripheral blood mononuclear cells (PBMCs)) and they do not induce IL-6 release in PBMCs (cf. FIG. 13).

The antibodies according to the invention, do not only inhibit the functional activation of cytokine release in different cell lines as described above, but also in PMBCs or whole blood cells from donors. They inhibit cytokine release mediated by different specific or complex stimuli. For example, they inhibit activation of PBMCs stimulated with LPS, heat-inactivated *Candida albicans*, IL-12/IL-33 or anti-CD3/CD28 antibodies (cf. FIGS. 14 and 15).

Figure 16:
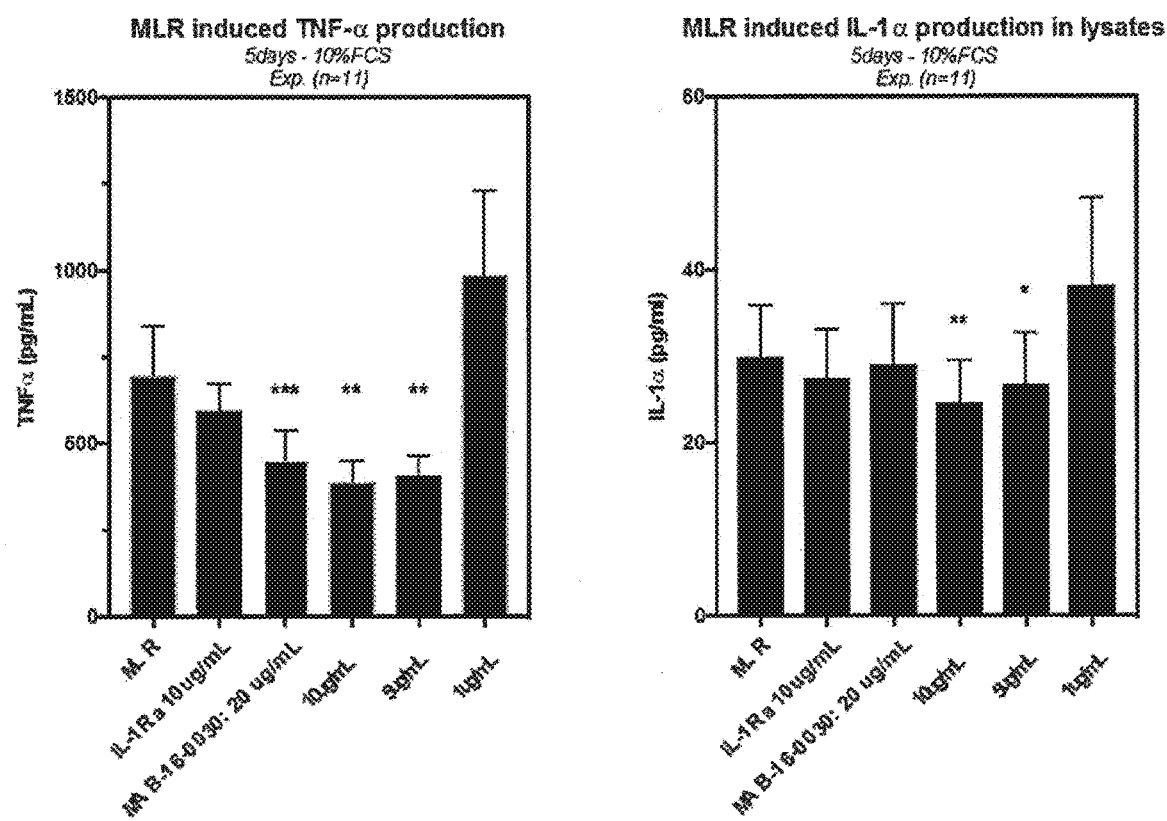
Figure 16:
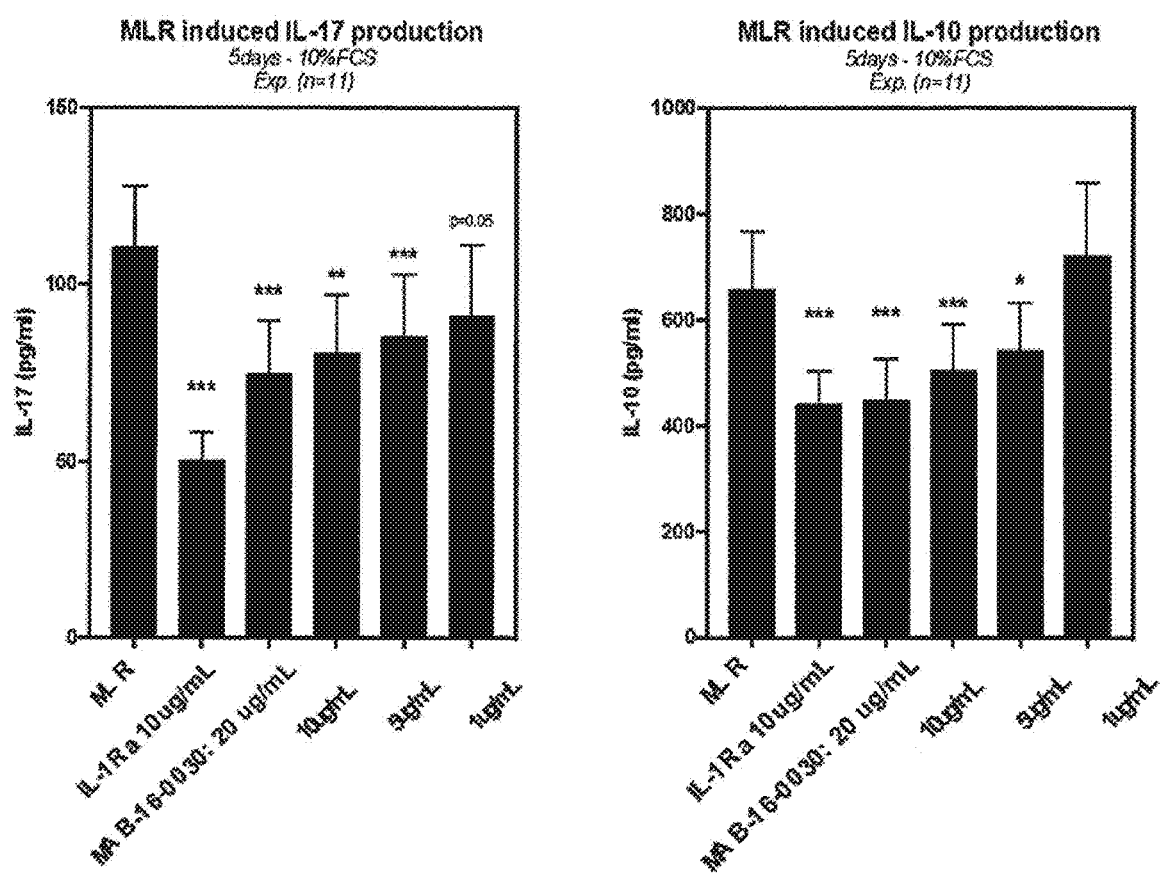

Also, in one embodiment, the humanized anti-IL-1R3 IgG1-LALA antibodies according to the invention are able to inhibit release of IFNg, IL-6, TNF-α, IL-13, IL-17 and IL-10 in mixed lymphocyte reactions (cf. FIG. 16).

Furthermore, the antibodies according to the invention, are especially useful for the treatment of diseases where the dysregulation of the target, IL1R3, is the underlying reason.

Therefore, the present invention further relates to a humanized antibody that specifically binds to IL-1R3 or a fragment or derivative thereof that contains at least a portion of said antibody that is sufficient to confer IL-1R3 binding specificity, for the use in treating a IL-1R3 mediated disease.

The present invention also encompasses a method of treating an IL-1R3 mediated disease in a patient, comprising administering to a patient a pharmaceutically effective amount of the antibody, or derivative or fragment thereof according to the invention.

The invention also relates to a pharmaceutical composition comprising a pharmaceutically acceptable carrier and a therapeutically effective amount of the humanized antibody that specifically binds to the IL-1R3 or a fragment or derivative thereof that contains at least a portion of said antibody that is sufficient to confer IL-1R3 binding specificity, according to the invention.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin. Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art. Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

One aspect of the invention is a pharmaceutical composition according to the invention for use in the treatment of cancer, as defined in this application.

Another aspect of the invention is a method of treating an IL-1R3 mediated disease in a patient, comprising administering to a patient the pharmaceutical composition according to the invention.

Such IL-1R3 mediated diseases may include cancer. It is described in the literature that a negative prognosis and progression in cancer is associated with increased levels of IL-1α, IL-1β, IL-33, IL-36 and/or increased expression of IL-1R3.

The term "cancer" as used herein may be, for example, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, lymphoma, lymphocytic leukemia, including refractory versions of any of the above cancers, or a combination of one or more of the above cancers. Preferably such cancer is a leukemia, breast cancer, colon cancer, lung cancer, or pancreatic cancer. Most preferably the cancer is leukemia.

In one embodiment, the IL-1R3 mediated disease is selected from the group consisting of leukemia, breast cancer, colon cancer, lung cancer, pancreatic cancer, liver cancer, non-small-cell-lung cancer, colorectal cancer, stomach cancer, gastric cancer, estrogen-receptor-positive breast cancer, head and neck squamous cell carcinoma, Mesothelioma, Gall bladder cancer, ovarian cancer, bladder cancer, prostate cancer, Thyroid cancer, Hodgkin disease, MALT lymphoma, salivary gland cancer, or melanoma.

Some tumors are caused or promoted by tumor microenvironment cells secreting inflammatory cytokines such as IL-1α, IL-1β, IL-33, IL-36. In some instances, expression of such cytokines results in the formation of tumor resistance. A concomitant use of cytokine inhibitors and anti-cancer compounds significantly improves the response rate of such treatments or can break tumor resistance. This is provided by the present invention because a broad spectrum of the inhibition of cytokine induced signaling is achieved. Such an activity in cancer indications is not achieved through a direct depletion activity of cancer cells but the inhibition of the cancer associated inflammation by modulating IL1R3 signaling pathways. The antibodies of the present invention provide a very much preferred activity profile because they enable an effective inhibition of cancer associated chronic inflammation and, at the same time, avoid undesired side effects, because they do not exhibit antibody effector function and thus do not affect the viability of targeted cells that express IL-1R3.

Therefore, in one embodiment of the present invention, the antibody or pharmaceutical composition is used for the treatment of patients, wherein the patients comprise a tumor, such as a solid tumor, and show insufficient response or tumor resistance to cytotoxic, cytostatic or targeted/immunotherapy.

In one aspect of the invention, the humanized antibody and/or the pharmaceutical composition according to invention, is meant for use in the treatment of cancer in combination with one or more cytotoxic, cytostatic or targeted anti-cancer compounds. The use of cytokine inhibitors and cytotoxic, cytostatic or targeted anti-cancer compounds significantly improves the response rate of such treatments or can break tumor resistance.

In such aspects of the invention, the cancer is preferably selected from the group consisting of pancreatic cancer, liver cancer, lung cancer (associated with inflammation caused by asbestos, infections, smoking, silica), non-small-cell-lung cancer, colorectal cancer/colitis-associated cancer (associated with Inflammatory bowel disease), stomach cancer, gastric cancer, chronic gastritis associated gastric cancer, estrogen-receptor-positive breast cancer, head and neck squamous cell carcinoma, Mesothelioma, Gall bladder cancer (Gall bladder stone-associated chronic cholecystitis associated), ovarian cancer, bladder cancer, prostate cancer, E. coli-infection associated prostate cancer, Thyroid cancer, Hodgkin disease, MALT lymphoma, salivary gland cancer, melanoma, endometriosis associated endometrial carcinoma, Barrett's esophagitis associated Esophageal cancer.

In one aspect of the method of this invention, the IL1R3 antibody or pharmaceutical composition according to the invention is administered simultaneously with one or more cytotoxic, cytostatic or targeted anti-cancer agents. In another aspect, the antibody or pharmaceutical composition is administered sequentially with one or more cytotoxic, cytostatic or targeted anti-cancer agents.

In the latter case, it is preferred that the antibody is administered after treatment with one or more cytotoxic, cytostatic or targeted anti-cancer agents.

The cytotoxic or cytostatic agents according to the invention can be taxanes, anthracyclins, alkylating agents, Histone Deacetylase Inhibitors, Topoisomerase inhibitors, kinase inhibitors, nucleotide analogs, peptide antibiotics, platinum-based agents and checkpoint inhibitors.

Preferably the targeted anti-cancer agents selected from one of the following, or combinations thereof: anti-EGFR compounds such as cetuximab, gefitinib, erlotinib, lapatinib, panitumumab, and anti-HER2 compounds such as trastuzumab, ado-trastuzumab emtansine, pertuzumab.

It is further preferred that the targeted anti-cancer agents are checkpoint inhibitors. These can be but are not limited to: anti-PD1 compounds such as pembrolizumab, and nivolumab, and anti-PDL1 compounds such as atezolizumab, Avelumab, and Durvalumab, and anti-CTLA-4 compounds such as Ipilimumab and Tremelimumab.

EXAMPLES

The following examples are used in conjunction with the figures and tables to illustrate the invention.

Example 1: Determination of P013_03 (Human IL-1R3) Specific Antibodies in B-Cell Supernatants Assay Principle:
NUNC Maxisorp 384 well microtiter plates are coated with P013_03. After a blocking process, specific antibodies from B-cell supernatants bind to the antigen and are then detected by a POD-labeled antibody. Samples are tested 1:2 diluted.

Materials:
Plates: 384 well NUNC Maxisorp plates; Cat. No. 464718
Proteins: P013-03 (Conc. 1.5 mg/ml; Assay Conc. 0.5 µg/ml)
Standard Ab: P013-02 (Conc. 1 mg/ml; Start Assay Conc. 2 µg/ml)
Detection Ab: Anti-rabbit IgG, peroxidase-linked species-specific whole antibody (from donkey) (ECL); GE; Cat. No. NA9340; assay dilution: 1:5000
PBS: Buffers in a Box, Premixed PBS Buffer, 10×; Roche Applied Sciences; Cat. No. 11666789001
BSA: Bovine Serum Albumin Fraction V from bovine serum; Roche Applied Sciences; Cat. No. 10735086001
Tween 20: Tween 20; Carl Roth; Cat. No. 9127.2
TMB: TMB Solution; Life Technologies; Cat. No. SB02
HCl: 1M Titripur Hydrochloric Acid; Merck; Cat. No. 1090571000
ELISA Buffer: PBS, 0.5% BSA, 0.05% Tween
Wash Buffer: PBS, 0.1% Tween
Block Buffer: PBS, 2% BSA, 0.05% Tween
Samples: 1:2 dilution in Elisa Buffer
Procedure:
1. Add 12.5 µL P013-03 (0.5 µg/ml) in PBS to a 384 well NUNC Maxisorp plate and incubate for 1 h at RT.
2. Wash 3× with 90 µl Wash Buffer.
3. Add 90 µL Blocking buffer to each well and incubate for 1 h at RT.
4. Wash 3× with Wash Buffer.
5. Add 12.5 µL Standard Antibody in 1:2 dilutions or sample 1:2 diluted in Elisa Buffer and incubate for 1 h at RT.
6. Wash 3× with Wash Buffer.
7. Add 12.5 µL 1:5000 POD-Antibody in Elisa Buffer and incubate for 1 h at RT.
8. Wash 6× with Wash Buffer.
9. Add 15 µL TMB.
10. Add 15 µL HCl after sufficient development.
11. Read absorbance at 450 nm/620 nm.

Example 2: Identification of P013-Specific Antibodies Inhibiting P013-Receptor by Luciferase Reporter Experiment Assay Principle:
293T/17-FR cells, which express a NF-kB-RE firefly luciferase reporter, are seeded into Poly-D-Lysin-Cell culture plates. After stimulation of P013 the 293T/17-FR lysate is tested for activated NF-kB using the Steady-Glo Luciferase Assay Kit. Supernatants with functional antibodies bind to P013 and inhibit the NF-kB activation, which is shown in low signal. Samples are tested 1:2 diluted in P013 solution.
Materials:
Plates: Cell plate: 384 well PDL Costar Cell Culture plate; Cat. No. 3844
Assay plate: 384 well lumitrac white-plate; Corning; Cat. No. 3572
Cells: 293T/17-FR; assay conc. 250.000 cells/ml
The higher the cell-passage the lower the signal!
Proteins: P013_05 (Conc. 0.03 mg/ml; Assay Conc. 115 pg/ml; Working Conc. 230 pg/ml)
Standard Ab: P013_06 (Conc. 0.2 mg/ml; Start Working Conc. 6 µg/ml)
Kit: Steady-Glo Luciferase Assay System; Promega; Cat. No. E2510
Cell-Medium: DMEM Medium; PAN Biotech; Cat. No. P04-04510
FCS: Fetal Bovine Serum, HyClone; Thermo; Cat. No. St30070.03
293T/17-FR Medium: DMEM Medium, 10% FCS, (+20 µg/ml Hygromycin-B, just for cultivation) Conditioned B-cell Medium (MAB Discovery)
Samples: 1:2 dilution with P013_05 in DMEM-Medium+ 10% FCS
Procedure:
1. Cell Culture Procedure:
   Split confluent 293T/17-FR cells every Monday (seed out: 5×106 cells/T175 flask) and Friday (seed out: 3×106 cells/T175 flask) using trypsin/EDTA (incubate just for 30 sec at RT).
2. Seed cells (0.25×106 cells/ml) in 25 µl DMEM+10% FCS to a 384-well PDL-plate (Corning cat #3844) and incubate over night at 37° C. and 5% CO2.
3. Aspirate media and add 12.5 µl Sample or P013_06 in 1:3 dilution in Conditioned Medium or just Conditioned Medium and incubate for 30 min at 37° C. and 5% CO2 (program: 3 Aspiration and Sample transfer)
4. Add 12.5 µl P013_05 in DMEM+10% FCS and incubate for 5 hours at 37° C. and 5% CO2 (program: 4_Add P013_05).
5. Equilibrate cultured cells to RT for 10 min.
6. Add 25 µl Steady-Glo Reagent and mix several times with pipette (program: 6_Steady Glo)
7. Wait 5 minutes before transfer 45 µl supernatant to a 384-well lumitrac white plate (Corning Cat#3572) (program: 7_Transfer 45 ul)
8. Measure luminescence in Tecan Reader: Integration Time: 0.5 sec Example 3: Determination of huIL1RaP, msIL1RaP, CD134 and CD137 Specific Antibodies in B-Cell Supernatants Assay Principle:
NUNC Maxisorp 384 well microtiter plates are coated with the target protein. After a blocking process, specific antibodies from B-cell supernatants bind to the targets and are then detected by a POD-labeled antibody.

Materials:
Plates: 384 well NUNC Maxisorp plates; Cat. No. 464718
Proteins: Cleaved huIL1RaP (P026_12; conc. 0.96 mg/mL; assay conc. 0.25 µg/mL)
    Cleaved muIL1RaP (P026_13; conc. 0.93 mg/mL; assay conc. 0.25 µg/mL)
    Cleaved CD134 (P026_14; conc. 0.51 mg/mL; assay conc. 0.25 µg/mL)
    Cleaved CD137 (P026_15; Batch2; conc. 1.1 mg/mL; assay conc. 1 µg/mL)
Standard Abs: Human IL-1 RAcP/IL-1 R3 Antibody (P013_6/P026_08; conc. 0.2 mg/mL or 0.399 mg/mL; start assay conc. 2 µg/mL; used for huIL1RaP and msIL1RaP)
    MAB-14-0283 (conc. 0.6 mg/mL; start assay conc. 2 µg/mL; used for CD134)
    MAB-14-0285 (conc. 1 mg/mL; start assay conc. 2 µg/mL; used for CD137)
Detection Ab: Samples: Anti-rabbit IgG, peroxidase-linked species-specific $Fab_2$ Fragment (from donkey) (ECL); GE; Cat. No. NA9340; assay dilution: 1:5000 in ELISA buffer
    For MAB-14-0283 and MAB-0285: Anti-human IgG peroxidase-linked species-specific $Fab_2$ Fragment (from goat) (HRP); AbD Serotec; Cat. No. STAR126P; assay dilution: 1:5000 in ELISA buffer
    For huIL1RaP and msIL1RaP: Peroxidase-conjugated AffiniPure Donkey Anti-Goat IgG (H+L); Jackson Immuno Research; Cat. No. 705-035-003; assay dilution: 1:5000 in ELISA Buffer
PBS: Buffers in a Box, Premixed PBS Buffer, 10×; Roche Applied Sciences; Cat. No. 11666789001
BSA: Bovine Serum Albumin Fraction V from bovine serum; Roche Applied Sciences; Cat. No. 10735086001
Tween 20: Tween 20; Carl Roth; Cat. No. 9127.2
TMB: TMB Solution; Invitrogen; Cat. No. SB02
HCl: 1M Titripur Hydrochloric Acid; Merck; Cat. No. 1090571000
ELISA Buffer: PBS, 0.5% BSA, 0.05% Tween
Wash Buffer: PBS, 0.1% Tween
Blocking Buffer: PBS, 2% BSA, 0.05% Tween
Samples: 1:4 dilution in ELISA Buffer Procedure:
1. Add 12.5 µL 0.25 µg/mL or 1 µg/mL protein diluted in PBS to a 384 well NUNC Maxisorp plate and incubate for 1 h at RT.
2. Wash 3× with 90 µL Wash Buffer.
3. Add 90 µL Blocking buffer to each well and incubate for 1 h at RT.
4. Wash 3× with 90 µL Wash Buffer. Plates can be stored in a dry state for up to 6 weeks at −20° C. sealed with an aluminum foil.
5. Add 12.5 µL Standard Antibody in 1:2 dilution steps or sample (diluted in ELISA Buffer) and incubate for 1 h at RT.
6. Wash 3× with 90 µL Wash Buffer.
7. Add 12.5 µL 1:5000 POD-Antibody in Elisa Buffer and incubate for 1 h at RT.
8. Wash 6× with 90 µL Wash Buffer.
9. Add 15 µL TMB.
10. Add 15 µL HCl after 15 min development.
11. Read absorbance at 450 nm/620 nm Example 4: Inhibition of NFκB-Expression of A549-NFκB-RE-Luc Stable Transfected Cells after Stimulation with IL-1 (α/β)

Assay Principle:
A549-NFκB-RE-Luc stable transfected cells (Signosis) are pipetted to a 384-well plate and incubated overnight. On day 2 anti-IL1R3 antibodies are allowed to bind to A549-NFkB-RE-Luc stable transfected cells, which are then stimulated by addition of IL-1 (α or β). This results in transcription of the luciferase gene due to NFκB signaling pathway activation and can be measured by cell lysis and addition of luciferin.

It is tested whether antibodies can inhibit the activation of NFkB pathway and therefore lower the luminescence signal.

Materials:
Plates: 384-well Low Flange White Flat Bottom Polystyrene TC-Treated Microplates Sterile; Corning; Cat. No. 3570
Proteins: IL-1 α (P026_09); Recombinant Human IL-1alpha/IL-1F1; 10 µg/mL; R&D Systems; Cat. No. 200-LA-002
IL-1 β (P026_10); Recombinant Human IL-1beta/IL-1F2; 25 µg/mL; R&D Systems; Cat. No. 200-LB-005
Standard Ab: MAB-15-0115; MAB Discovery GmbH; 2.51 mg/ml; working conc. 10 µg/ml
Cells: A549-NFκB-RE-Luc stable transfected cells; Signosis; Cat. No. SL-0014
Medium: DMEM; PAN; Cat. No. P04-04510
FCS: Fetal Bovine Serum South Africa Low IgG; PAN; Cat. No. 1552-P120909
Pen/Strep: 10,000 U Penicillin/ml; 10 mg Streptomycin/ml; PAN Biotech; Cat. No. P06-07100
Detaching Agent: Trypsin-EDTA 1×; PAN; Cat. No. P10-023100 (4 mL for T175/2 mL for T75; ~8 min 37° C.)
Cell-Medium: DMEM, 10% FCS, 1% Pen/Strep
Detection Kit: Steady-Glo™ Luciferase Assay System; Promega; Cat. No. E2510

Procedure:
1. Cultivate A549-NFκB-RE-Luc stable transfected cells (1.7E+04 cells/$cm^2$ for 3 days; 2.28E+04 cells/$cm^2$ for 2 days) in Cell-Medium. Do not go beyond 10 passages!
2. Plate out 40,000 A549-NFκB-RE-Luc stable transfected cells in 25 µL medium per well (conc.=$1.6×10^6$ cells/mL) to a white cell-culture treated 384 well plate with flat bottom.
Incubate over night at 37° C./5% $CO_2$.
3. Aspirate medium from plate and add 10 µL sample or standard in medium to plate using CyBio pipetting roboter (Program: "Medium removal and sample transfer" in folder P026/NFκB). Incubate for 1 h at 37° C./5% $CO_2$.
4. Add 10 µL IL-1 (α or β) in medium to plate using CyBio pipetting roboter (Program: "Transfer from reservoir" in folder P026/NFκB) (working conc.: 0.2 ng/mL; assay conc.: 0.1 ng/mL) and incubate 5 h at 37° C./5% $CO_2$.

Before performing step 4, dissolve Steady-Glo substrate in Steady-Glo buffer according to Steady-Glo protocol and equilibrate this solution and the assay plate to RT.
5. Add 20 μL Steady-Glo mix, mix thoroughly to guarantee proper cell lysis. Incubate at RT, 10 min.
6. Determine the relative luminescence units of each well, using a microplate reader set to 500 ms integration time (program: Lumineszenz-384).

Example 5: IL-6 Secretion of A549 Cells after Stimulation with IL-1 (α/β)

Assay Principle:
A549 cells are pipetted to a 384-well plate and incubated with anti-IL1R3 antibodies. Afterwards, the cells are stimulated with IL-1 (α or β) and secrete IL-6 into the assay medium. The amount of IL-6 is measured by an IL-6 ELISA.
Materials:
Assay Kit: DuoSet ELISA Human IL-6; Cat. No. DY206-05 (R&D Systems); DuoSet is consisting out of Human IL-6 Capture Antibody (part 840113), Human IL-6 Detection Antibody (part 840114), Human IL-6 (part 840115) and Streptavidin-HRP (part 8939755)
Plates: 384-well clear cell culture treated plates; Corning; Cat. No. 3701 384-well Maxisorp plates; NUNC; Cat. No. 464718
PP-Plate: 120 μL 384 Deep Well "Diamond" Plate, Clear; Axygen (Corning); Cat. No. P-384-120SQ-C
Proteins: IL-1 α; Recombinant Human IL-1alpha/IL-1F1; R&D Systems; Cat. No. 200-LA-002 IL-1 β; Recombinant Human IL-1beta/IL-1F2; R&D Systems; Cat. No. 200-LB-005 rhIL1-ra/IL-1F3; R&D Systems; Cat. No. 280-RA-010
Standard Abs: Human IL-1RAcP/IL-1R3 antibody; R&D Systems; Cat. No. AF676 or AF676-SP
Medium: DMEM; PAN; Cat. No. P04-04510
FCS: Fetal Bovine Serum South Africa Low IgG; PAN; Cat. no. 1552-P120909
Pen/Strep: 10,000 U Penicillin/ml; 10 mg Streptomycin/ml; PAN Biotech; Cat. no. P06-07100
PBS: Buffers in a Box, Premixed PBS Buffer, 10×; Roche Applied Sciences; Cat. No. 11666789001
BSA: Bovine Serum Albumin Fraction V from bovine serum; Roche Applied Sciences; Cat. No. 10735086001
Tween 20: Tween 20; Carl Roth; Cat. No. 9127.2
TMB: TMB Solution; Invitrogen; Cat. No. SB02
HCl: 1 M Titripur Hydrochloric Acid; Merck; Cat. No. 1090571000
ELISA Buffer: PBS, 0.5% BSA, 0.05% Tween
Wash Buffer: PBS, 0.1% Tween
Block Buffer: PBS, 2% BSA, 0.05% Tween
Cell-Medium: DMEM, 10% FCS, 1% Pen/Strep
Procedure:
Cell Stimulation
1. Plate out 6,000 A549 cells in 25 μL medium per well (conc.=$2.4 \times 10^5$ cells/mL) to a cell culture plate. Incubate over night at 37° C./5% $CO_2$.
2. Aspirate medium from plate and add 12.5 μL sample or standard in medium to plate. Incubate for 3 h at 37° C./5% $CO_2$.
3. Add 12.5 μL IL-1 (α or β) to plate (working conc.: 0.2 ng/mL; assay conc.: 0.1 ng/mL) and incubate 48 h at 37° C./5% $CO_2$.
4. Aspirate medium and transfer to the coated and blocked Elisa plate (step 9). Alternatively, the supernatants can be stored at −80° C. in a PP-Plate for up to one week.

Elisa Plate Preparation
5. Dilute the Capture Antibody to a concentration of 2 μg/mL in PBS. Immediately coat a 384-well Maxisorp plate with 12.5 μL per well of the diluted Capture Antibody. Seal the plate and incubate 1 h at room temperature.
6. Aspirate each well and wash with Wash Buffer, repeating the process two times for a total of three washes. Wash by filling each well with Wash Buffer (90 μL) using an autowasher. Complete removal of liquid at each step is essential for good performance. After the last wash, remove any remaining Wash Buffer by aspirating or by inverting the plate and blotting it against clean paper towels.
7. Block plates by adding 90 μL Blocking Buffer to each well. Incubate at room temperature for a minimum of 1 h.
8. Repeat the aspiration/wash as in step 6. The plates are now ready for sample addition. The coated and blocked plates can be stored at −20° C. in a dry state for up to one month.
Assay Procedure
9. Add 12.5 μL of pure sample or IL-6 standard diluted in ELISA Buffer (EB) per well. Cover and incubate 1 h at room temperature.
10. Repeat the aspiration/wash as in step 6 of Elisa Plate Preparation.
11. Add 12.5 μL of the Detection Antibody, diluted in EB, to each well. Cover and incubate 1 h at room temperature.
12. Repeat the aspiration/wash as in step 6 of Elisa Plate Preparation.
13. Add 12.5 μL of 1:40 diluted Streptavidin-HRP in Elisa Buffer to each well. Cover the plate and incubate for 20 minutes at room temperature. Avoid placing the plate in direct light.
14. Repeat the aspiration/wash as in step 6 of Elisa Plate Preparation.
15. Add 15 μL of Substrate Solution (TMB) to each well. Incubate for 20 minutes at room temperature.
16. Add 15 μL of Stop Solution (HCl, 1 M) to each well. Gently tap the plate to ensure thorough mixing.
17. Determine the optical density of each well immediately, using a microplate reader set to 450 nm. If wavelength correction is available, set to 540 nm or 570 nm (program: TMB stop 384 Cytokine). Readings made directly at 450 nm without correction may be higher and less accurate.

Example 6: Determination of Binding Characteristics of huIL1RaP Specific Antibodies by Competition Assay Assay Principle:
NUNC Maxisorp 384 well microtiter plates are coated with the reference antibody Can04. During this time the His-tagged target protein is pre-incubated with the second antibody to test and an anti-HIS-POD antibody. Afterwards this preincubation-mix is added to the assay plate and after a sufficient development time the absorbance at 450 nm/620 nm is measured.
Materials:
Plates: 384 well NUNC Maxisorp plates; Cat. No. 464718
Coating Ab: Can04 (MAB Discovery GmbH; CEP Ab no. 184; conc. 1 mg/ml; assay conc. 100 ng/ml)

Protein: huIL1RaP-His protein (P026_01; Fusion_1_Chain_A Homodimer huIL1RaP-His tagged; GeneArt; conc. 3 mg/ml; assay conc. 62.5 ng/ml)

Standard Abs: Can04 (see: "Coating Ab"; start working conc. 3 µg/ml)

Negative control: Her2 antibody (Lifespan; Cat. no. LS-C95808/26358; conc. 225 µg/mL; start working conc. 3 µg/ml)

Detection Ab: anti-HIS POD Antibody (Monoclonal Anti-polyHistidine Peroxidase Conjugate; Sigma; Cat. No. A7058; conc. 7.5 mg/ml; assay conc.: 3.33 µg/ml)

PBS: Buffers in a Box, Premixed PBS Buffer, 10×; Roche Applied Sciences; Cat. No. 11666789001

BSA: Bovine Serum Albumin Fraction V from bovine serum; Roche Applied Sciences; Cat. No. 10735086001

Tween 20: Tween 20; Sigma-Aldrich; Cat. No. P1379

TMB: TMB Solution; Merck; Cat. No. CL07

HCl: 1M Titripur Hydrochloric Acid; Merck; Cat. No. 1090571000

ELISA Buffer: PBS, 0.5% BSA, 0.05% Tween

Wash Buffer: PBS, 0.05% Tween

Block Buffer: PBS, 2% BSA, 0.05% Tween

Procedure:
12. Prepare the Pre-incubation-mix and incubate for 2 h at RT.
    a. Pre-incubation (in 384 well plate)
       i. Mix 10 µl Secondary Antibody dilution series (dilution 1:2; start working conc.: 3 µg/ml) in ELISA buffer or BLANK with
       ii. 10 µl His-tagged protein (assay conc. 62.5 ng/ml) and
       iii. 10 µl anti-HIS POD antibody (assay conc.: 3.33 µg/ml) and incubate for 1 h at RT.
13. In the meantime, coat a NUNC Maxisorp plate with 20 µl Coating Antibody (Can04; assay conc. 100 ng/ml) in PBS and incubate for 1 h at RT.
14. Wash 3× with 90 µl Wash Buffer.
15. Block with 90 µl Blocking Buffer for 1 h at RT.
16. Wash 3× with Wash Buffer.
17. Add 20 µl Pre-incubation-mix in ELISA-Buffer for 1 h at RT.
18. Wash 6× with Wash Buffer.
19. Add 25 µL TMB.
20. Add 25 µL HCl after sufficient development.
21. Read absorbance at 450 nm/620 nm.

Example 7: IL12 Counter Screen

Assay Principle:

The IL12 binding is used as a counterscreen. The HER proteins are tagged with a linker, huFc and His (HER1 does not have a His-Tag) like the IL12 protein. Antibodies which bind to the tag are positive in both assays, whereas antigen specific antibodies just bind to the HER proteins and not to IL12.

Materials:

Plates: 384 well NUNC Maxisorp plates; Cat. No. 464718

Proteins: Recombinant Human IL-12 Rβ1 Fc Chimera; R&D Systems; Cat. No. 839-B1; assay conc. 0.5 µg/mL Standard Abs: IL-12Rbeta1 antibody; GeneTex; Cat. No. GTX103917; 1 mg/mL; start assay conc. 500 ng/mL (then 1:2 dilutions)

Detection Ab: Anti-rabbit IgG, peroxidase-linked species-specific Fab$_2$ Fragment (from donkey) (ECL); GE; Cat. No. NA9340; assay dilution: 1:5000

Samples: Dilution in ELISA buffer is project dependent (for high concentrated IgGs 1:2 dilution is recommended)

Procedure:
1. Add 12.5 µL 0.5 µg/mL HER protein in PBS to a 384 well NUNC Maxisorp plate and incubate for 1 h at RT.
2. Wash 3× with Wash Buffer.
3. Add 90 µL Blocking buffer to each well and incubate for 1 h at RT.
4. Wash 3× with Wash Buffer. Plates can be frozen for several weeks at −20° C. sealed with an aluminum foil.
5. Add 12.5 µL Standard Antibody in 1:2 dilutions or sample diluted in ELISA buffer and incubate for 1 h at RT (the frozen plates should be thawed shortly before sample application).
6. Wash 3× with Wash Buffer.
7. Add 12.5 µL 1:5000 POD-Antibody in Elisa Buffer and incubate for 1 h at RT.
8. Wash 6× with Wash Buffer.
9. Add 15 µL TMB.
10. Add 154 HCl after sufficient development (project dependent; IL12 assay not shorter than other assays).
11. Read absorbance at 450 nm/620 nm.

Example 8: Cell Binding Analysis

A549 and NIH-3T3 cells were cultured in DMEM+10% FCS. HEK-293 cells were cultured in DMEM+15% FCS and SK-MEL-30 in RPMI+10% FBS. Cells were harvested using Accumax (Sigma), washed with PBS and resuspended in stain buffer (BD Pharmingen). Anti-IL-1R3 antibodies were incubated with the cells in stain buffer for 30 minutes at 4° C. at a concentration of 10 µg/ml. For EC50 SK-MEL-30 cell binding analysis, cells were incubated in a 1:2 dilution series starting with 20 µg/ml. Cells were washed with stain buffer and incubated with Alexa-488 labelled goat-anti-human secondary antibody (Dianova) for 30 minutes at 4° C. Cells were washed with stain buffer and resuspended in buffer containing 1:100 diluted DRAQ7 (Abcam) dead cell stain. Cells were analysed using a BD Accuri C6 Sampler flow cytometer. Fitting curve and EC50 calculation was done using Excel (Microsoft) and XLfit (IDBS).

Example 9: Biochemical Human-11-1R3 ELISA

Nunc 384-well Maxisorp plates were coated with recombinant Fc-tagged hIL-1R3 (Ser21-Glu359) at a concentration of 0.25 µg/ml in PBS for 60 minutes at room temperature. Plates were washed three times with wash buffer (PBS 0.1% Tween) and blocked with PBS, 0.2% BSA, 0.05% Tween for 60 minutes at room temperature. After three washes with wash buffer, antibodies were added in ELISA buffer (PBS, 0.5% BSA, 0.05% Tween) at concentrations ranging from 6 to 0.03 µg/ml (1:3 dilution series) and were incubated for 60 min at room temperature. Plates were washed three times with wash buffer, followed by incubation with anti-human-IgG peroxidase-linked, species specific F(ab)2 Fragment (goat, AbD Serotec) at a dilution of 1:5000 in ELISA Buffer for 60 minutes at room temperature. Plates were washed six times with wash buffer before TMB substrate solution (Invitrogen, 15 µl/well) was added. After 5 minutes of incubation, stop solution (1M HCl, 15 µl/well) was added and absorbance (450 nm/620 nm) measured using a Tecan M1000 plate reader. Fitting curves and EC50 calculation were done using Excel (Microsoft) and XLfit (IDBS).

Example 10: IL-1α and IL-1μ Functional Neutralization Assay

A-549-NFκB-RE-Luc (Signosis) were cultivated in DMEM, 10% FCS, 1% Pen/Strep for 5 days before they were seeded out in 384-well white flat bottom polystyrene tissue-culture-treated microplates (Corning) at a cell density of 40,000 cells/well in 25 μl medium. Cells were incubated over night at 37° C./5% $CO_2$. Medium was removed by aspiration and monoclonal or polyclonal (goat-anti-human-IL-1R3, AF676, R&D Systems) antibodies added at various concentrations in a volume of 10 μl medium and incubated for 60 minutes at 37° C./5% $CO_2$. Recombinant human IL-1α or IL-1β (R&D Systems) proteins were added in 10 μl medium to a final concentration of 0.1 ng/ml and plates were incubated for 5 hours at 37° C./5% $CO_2$. 20 μl Steady-Glo™ (Promega) solution were added to each well, mixed thoroughly and plates were incubated for 10 minutes at room temperature before luminescence was measured using a Tecan M1000 plate reader. Fitting curves and EC50 calculation were done using Excel (Microsoft) and XLfit (IDBS).

Example 11: IL-1α and IL-1β Functional Neutralization Assay—A-549 IL6-Release Assay A549 cells were seeded out at a density of 6,000 cells/well in 25 μl medium in 384-well clear cell culture treated plates (Corning) in DMEM, 10% FCS, 1% Pen/Strep. Cells were incubated over night at 37° C./5% $CO_2$. Medium was removed by aspiration and monoclonal or polyclonal (goat-anti-human-IL-1R3, AF676, R&D Systems) antibodies were added at various concentrations in a volume of 12.5 μl medium and incubated for three hours at 37° C./5% $CO_2$. Recombinant human IL-1α or IL-1β (R&D Systems) proteins were added in 12.5 μl medium to a final concentration of 0.1 ng/ml and plates were incubated for 48 hours at 37° C./5% $CO_2$. Secreted human-IL-6 levels in the cell supernatant were measured using the DuoSet human IL-6 ELISA kit (R&D Systems, Cat. No. DY206-05) according to the manufacturer's instructions. Fitting curves and EC50 calculation were done using Excel (Microsoft) and XLfit (IDBS).

Example 12: IL-33 Functional Neutralization Assay

HEK-Blue™ IL-33 cells (InvivoGen) were cultivated in DMEM, 10% FCS for 5 days before they were seeded out in 384-well clear, flat bottom, cell culture treated microplates (Corning) at a cell density of 25,000 cells/well in 15 μl medium. Various concentrations of monoclonal or polyclonal (goat-anti-human-IL-1R3, AF676, R&D Systems) antibodies were added in a volume of 5 μl medium and plates were incubated for 60 minutes at 37° C./5% $CO_2$. Recombinant human IL-33 (R&D Systems) protein was added in 5 μl medium to a final concentration of 5 ng/ml and plates were incubated over night at 37° C./5% $CO_2$. 5 μl cell supernatants were transferred to clear, flat bottom polystyrene NBS™ microplates (Corning) containing 20 μl 2× QUANTI-Blue reagent (InvivoGen). Plates were incubated at 37° C. for 45 minutes and optical density measured at 655 nm using a Tecan M1000 plate reader. Fitting curves and EC50 calculation were done using Excel (Microsoft) and XLfit (IDBS).

Example 13: IL-36 Functional Neutralization Assay

HEK293/17-IF Cells (MAB Discovery GmbH) were cultivated in DMEM, 10% FCS, 20 μg/ml hygromycin for 5 days before they were seeded out in 384-well white, flat bottom, cell culture treated plates (Corning) at a cell density of 30,000 cells/well in 20 μl medium. Cells were incubated over night at 37° C./5% $CO_2$. Medium was removed by aspiration and various concentrations of monoclonal or polyclonal (goat-anti-human-IL-1R3, AF676, R&D Systems) antibodies were added in a volume of 10 μl medium. Plates were incubated for 60 minutes at 37° C./5% $CO_2$. Recombinant human IL-36g (R&D Systems) protein was added in 10 μl medium to a final concentration of 15 ng/ml and plates were incubated for 5 hours at 37° C./5% $CO_2$. 20 μl Steady-Glo™ (Promega) solution was added to each well, mixed thoroughly and plates were incubated for 10 minutes at room temperature before luminescence was read using a Tecan M1000 plate reader. Fitting curves and EC50 calculation were done using Excel (Microsoft) and XLfit (IDBS).

Example 14: Neutralization of IL-1α, IL-33 and IL-36α

The functions of anti-IL-1R3 antibodies were tested on three different cell lines with either IL-1α, IL-33 or IL-36α to determine the impact on the signaling pathways involving the three IL-1 receptors (IL-1R1, -R4 or -R6) dependent upon IL-1R3 for signaling.

The human epithelial lung cell line A549 was stimulated with IL-1α as a model of IL-1 dependent diseases such as auto-inflammatory diseases. The cell line was cultured in T75 flasks (37° C., 5% $CO_2$) in complete F-12K media (10% FCS, 1% Pen/Strep) and split on average 2 times/week, not exceeding 15 passages before assaying. A549 cells were seeded out (50.000/well) in a 96 flat-bottom plate, rested for 3 hrs before pre-incubating 1 hr with MAB-16-0030 (20 μg/mL-1 μg/mL) or IL-1Ra (10 μg/mL). Cells were then stimulated with recombinant human IL-1α (50 pg/mL, Peprotech) for 24 hrs before harvesting supernatants and assaying for IL-6 production (Duoset ELISA, RnD Systems).

A human mast cell line (HMC-1) was investigated for IL-33-dependent induction of IL-8 production. The cell line was cultured in T75 flasks (37° C., 5% $CO_2$) in complete Iscove's modified Dulbeccos's medium (IMDM, 10% FCS, 1% Pen/Strep) and split on average 3 times/week, not having a cell density above $2*10^6$/mL nor exceeding 15 passages before assaying. HMC-1 cells were seeded out (30.000/well) in a 96 flat-bottom plate, rested for 3 hrs before pre-incubating 1 hr with MAB-16-0030 (20 μg/mL-1 μg/mL) or IL-1Ra (10 μg/mL). Cells were then stimulated with recombinant human IL-33 (20 ng/mL, RnD systems) for 24 hrs before harvesting supernatants and assaying for IL-8 production (Duoset ELISA, RnD Systems).

The impact on IL-36 signaling was investigated using a human keratinocytic cell line (HaCaT). The cell line was cultured in T75 flasks (37° C., 5% $CO_2$) in complete DMEM (10% FCS, 1% Pen/Strep) and split on average 3 times/week not exceeding 15 passages before assaying. HaCaT cells were seeded out (50.000/well) in a 96 flat-bottom plate, rested for 3 hrs before pre-incubating 1 hr with MAB-16-0030 (20 μg/mL-1 μg/mL) or IL-1Ra (10 μg/mL). Cells were then stimulated with recombinant human IL-36α (50 ng/mL, RnD systems) for 24 hrs before harvesting supernatants and assaying for IL-8 production (Duoset ELISA, RnD Systems).

Example 15: Viability and IL-6 Release of PBMC

The impact of anti-hIL-1R3 antibody MAB-16-0030 on the viability of unstimulated PBMCs (500.000/well) from three healthy donors was tested using a conventional MTT reduction assay. Briefly, PBMCs (2004) were incubated with either media alone or MAB-16-0030 (20 µg/mL). After 24 hrs, 3 and 5 days, PBMCs were incubated for 2 hrs with MTT (204), before measuring absorbance at 570 nM on an ELISA reader. Using the known linearity between absorbance and viable cells converting MTT, the number of viable cells was calculated using media alone as the control set to 100%. At the same day of MTT analysis, supernatants from PBMCs incubated under same conditions and from same donors, were harvested and subsequently assayed for IL-6 production (Duoset ELISA, RnD systems) to evaluate any possible stimulatory effect of MAB-16-0030 alone.

Example 16: Functional Blockage of PBMCs

Freshly isolated PBMCs from healthy donors were used to evaluate the impact of MAB-16-0030 on human cells stimulated with diverse antigens. For all stimuli, the experiments were carried out using 500.000 PBMCs/well, stimulating in a total volume of 2004. Cells were seeded out and incubated with either media alone, MAB-16-0030 (20-0.1 µg/mL) or IL-1Ra (10 µg/mL) for 1 hr before stimulation. The following stimuli were used; LPS (10 ng/mL, 24 hrs, RPMI no FCS), anti-human CD3/CD28 (1.25 µg/mL; 0.5 µg/mL (eBioscience) 3 days, RPMI 10% FCS), IL-12/-33 (2 ng/mL; 20 ng/mL (Peprotech; RnD Systems)), 3 days, RPMI 10% FCS) or heat-inactivated *Candida albicans* ($0.5*10^6$/mL, 5 days, RPMI 10% FCS). After stimulation, supernatants were harvested and assayed for cytokine production using Duoset ELISAs (RnD Systems) according to manufactures protocol.

Example 17: Functional Blockage of Immune Cells in Whole Blood

Heat-inactivated *Candida albicans* were used to stimulate whole blood. Freshly harvested blood from healthy donors (EDTA tubes) were distributed in micro-centrifuge tubes (250 µL/tube) and pre-incubated with either media alone (RPMI, no FCS), MAB-16-0030 (20-0.1 µg/mL) or IL-1Ra (10 µg/mL) for 1 hr before stimulation with *Candida albicans* ($0.5*10^6$/mL) to a final volume of 1 mL. After 24 hrs incubation (37° C., 5% $CO_2$), supernatants were harvested and assayed for cytokine production by ELISA (Duoset, RnD Systems).

Example 18: Mixed Lymphocyte Reactions (MLR)

PBMCs from healthy, non-matching donors were mixed in a 1:1 ratio (250.000/donor) and incubated for 5 days (RPMI, 10% FCS) with either media alone, MAB-16-0030 (20-1 µg/mL) or IL-1Ra (10 µg/mL). Cytokine production were assayed using a Quansys multiplex platform according to manufacturer's protocol.

FIGURE LEGEND

FIG. 1: Sequences (Amino Acids in One Letter Code) Complete Sequences of Variable Regions (VR):

| Heavy chain: | VH complete: SEQ ID NO: 1-34 and SEQ ID NO: 173 |
|---|---|
| Light chain: | VL complete: SEQ ID NO: 35-68 and SEQ ID NO: 174 |

Complementary Determining Regions (CDR):

| Heavy Chain: | CDRH1: | SEQ ID NO: 69-85 |
|---|---|---|
| | CDRH2: | SEQ ID NO: 86-102 |
| | CDRH3: | SEQ ID NO: 103-119 |
| Light Chain: | CDRL1: | SEQ ID NO: 120-136 |
| | CDRL2: | SEQ ID NO: 137-153 |
| | CDRL3: | SEQ ID NO: 154-170 and 175 |

Constant Regions (CR):

| Light Chain: | CR-L: | SEQ ID NO: 171 |
|---|---|---|
| Heavy Chain: | CR-H: | SEQ ID NO: 172 |

In the following Figures, AF676 is a commercial polyclonal antibody preparation purchased from the following link: www.rndsystems.com/products/human-il-1-racp-il-1-r3-antibody_af676.

FIG. 2: Human IL-1R3 ELISA

A 384 microtiter plate was coated with human II-1R3 protein representing the human extracellular domain of IL-1R3 (0.5 mg/ml, at least 1 h). After an intensive washing step followed by a blocking step, antibodies were added (12.5 µl per well) and incubated for 1 h at RT. Unbound antibody was washed out intensively. The amount of bound antibody was identified by incubating the microtiter plate with a Peroxidase labelled anti-human detection antibody (1 h at RT). The Peroxidase reaction was initiated by adding TMB and measuring the absorbance at 450 nm/620 nm.

To ensure binding specifically to human IL-1R3, a counter screen using an IL12 protein with identical features was performed in parallel. The set-up of the assay was identical as described above. B-cell supernatants binding to human IL-1R3, but not to IL12 have been regarded as being active.

FIG. 3: HEK293 Reporter Assay

HEK293T/17-FR cells were stable transfected with the pGL4.32[luc2P/NF-κB-RE/Hygro] vector (Promega) and seeded in 384 well PDL Costar Cell Culture plates followed by 30 min incubation with the antibodies. The cells were then stimulated with IL-1β for 5 hours before the NF-kB activity was determined using the Steady-Glo Luciferase Assay Kit (Promega) according to manufacturer's protocol.

FIG. 4: NFκB Luciferase Reporter Assay Using an A549 Stable Cell Line

A549-NFkB-RE-Luc stable transfected cells (purchased from Signosis) have been cultivated for 3 days (1.7E+04 cells/$cm^3$). 384-well low flange white flat bottom polystyrene TC-treated microtiter plates (Corning) were filled with $4\times10^4$ cells per well. After a cultivation period of 10 h the cells were incubated with the antibodies for 1 h before the cells were stimulated with 10 µl IL-1β for another 5 h. NFkB modulation has been measured by Steady-Glo™ Luciferase Assay System (Promega) determining relative luminescence units of each well in relation to non-stimulated cells.

FIG. 5: Cell Binding Analysis: Binding to IL-1R3 Expressing Cells

Humanized anti-IL-1R3 IgG1-LALA antibodies were tested for binding to cell lines with different IL-1R3 receptor densities using flow cytometry. Humanized anti-IL-1R3 IgG1-LALA antibodies bind to low- and high-IL-1R3-expressing cell lines. Antibodies do not bind to mouse NIH-3T3 cells. Experiments were carried out according to the method described in Example 8.

FIG. 6: Cell Binding Analysis: Cell Binding on Human-IL-1R3 High Expressing Cell Line SK-MEL-30

EC50 cell binding values of humanized anti-IL-1R3 IgG1-LALA antibodies were determined by binding to high-IL-1R3-expressing cell line SK-MEL-30 using flow cytometry. Humanized anti-IL-1R3 IgG1-LALA antibodies MAB-16-0030 and MAB-16-0149 show cell binding of 307 and 306 ng/ml, respectively. Experiments were carried out according to the method described in Example 8.

FIG. 7: Human-IL-1R3 Biochemical ELISA

Binding of humanized anti-IL-1R3 IgG1-LALA antibodies to recombinant human IL-1R3 protein was tested in biochemical ELISA. Exemplified antibodies show EC50 binding values of 16.3 ng/ml and 29.1 ng/ml, respectively. Experiments were carried out according to the method described in Example 9.

FIG. 8: Inhibition of Human IL-1a and IL-1b Mediated NfKB Signaling in A549-NFkB-RE-Luc Cells Functional neutralization of IL-1a and IL-1b was tested in a cell based gene reporter assay using A549-NFkB-RE-Luc cells stimulated with 0.1 ng/ml IL-1a and IL-1b, respectively. Humanized anti-IL-1R3 IgG1-LALA antibodies show EC50 values superior to that of goat-anti-human-IL1-R3 polyclonal antibody AF676 (R&D Systems). Experiments were carried out according to the method described in Example 10.

FIG. 9: IL-1α and IL-1β Functional Neutralization Assay—Inhibition of Human IL-1a and IL-1b Mediated IL-6 Release by A-549 Cells Neutralization of IL-1α and IL-1b mediated cellular release of IL-6 by humanized anti-IL-1R3 IgG1-LALA antibodies was tested using A-549 cells. EC50 values demonstrate that humanized anti-IL-1R3 IgG1-LALA antibodies are superior to that of goat-anti-human-IL1-R3 polyclonal antibody AF676 (R&D Systems). Experiments were carried out according to the method described in Example 11.

FIG. 10: IL-33 Functional Neutralization Assay—Inhibition of Human IL-33 Mediated NfkB-Signaling in HEK-Blue-IL33™ Cells Neutralization of IL-33 mediated cell signaling by humanized anti-IL-1R3 IgG1-LALA antibodies was tested using IL-33 stimulated gene reporter HEK-Blue-IL33™ cells (InvivoGen). EC50 values demonstrate that humanized anti-IL-1R3 IgG1-LALA antibodies are superior to that of goat-anti-human-IL1-R3 polyclonal antibody AF676 (R&D Systems). Experiments were carried out according to the method described in Example 12.

FIG. 11: IL-36 Functional Neutralization Assay—Inhibition of Human IL-36 Mediated NfkB-Signaling in HEK-293/17-IF Cells Neutralization of IL-36 mediated cell signaling by humanized anti-IL-1R3 IgG1-LALA antibodies was tested using IL-36g stimulated gene reporter HEK-293/17-IF cells. Typical humanized anti-IL-1R3 IgG1-LALA antibodies show EC50 values superior to that of goat-anti-human-IL1-R3 polyclonal antibody AF676 (R&D Systems). Experiments were carried out according to the method described in Example 13.

FIG. 12: Neutralization of IL-1a, IL-33 and IL-36a Mediated Cellular Cytokine Release Neutralization of IL-1a, IL-33 and IL-36α mediated cellular cytokine release was tested using specific IL-1a, IL-33 and IL-36a dependent cell systems. The Inhibition of cytokine release by a representative humanized anti-IL-1R3 IgG1-LALA antibody according to the invention (MAB-16-0030) was tested and compared to IL-1Ra. While the antibody according to the invention was able to inhibit cytokine release mediated by all three stimuli, IL-1Ra affected only IL-1α mediated cytokine release. Experiments were carried out according to the method described in Example 14.

FIG. 13: Viability and IL-6 Release of Unstimulated PBMC Treated with a Humanized Anti-IL-1R3 IgG1-LALA Antibody Binding of antibodies to immune cells may result in cell depleting and deleterious effects, e.g. by direct induction of apoptotic signaling pathways, stimulation of excessive cytokine release or antibody-dependent cellular cytotoxicity (ADCC). To exclude that humanized anti-IL-1R3 IgG1-LALA antibodies directly affect the viability of PBMCs, the viability of PBMCs of three donors and IL-6 release was investigated after incubation with different concentrations of a representative humanized anti-IL-1R3 IgG1-LALA antibody according to the invention (MAB-16-0030) for 1, 3 and 5 days. Neither viability nor IL-6 release was affected by MAB-16-0030. These results support that the humanized anti-IL-1R3 IgG1-LALA antibodies block IL-1R3 function on immune cells without circumstantial cell-depletion and induction of cell-deleterious effects. Experiments were carried out according to the method described in Example 15.

FIG. 14: Functional Blockage of PBMCs Activated with Different Stimuli

To test whether humanized anti-IL-1R3 IgG1-LALA antibodies inhibit activation of PBMCs stimulated with specific or complex stimuli, PBMCs of 10 donors were stimulated with LPS, heat-inactivated *Candida albicans*, IL-12/IL-33 or anti-CD3/CD28 antibodies. A representative humanized anti-IL-1R3 IgG1-LALA antibody according to the invention was able to inhibit cytokine release mediated by all tested stimuli. Experiments were carried out according to the method described in Example 16.

FIG. 15: Functional Blockage of Immune Cells in Whole Blood Activated with *Candida albicans*

To test whether humanized anti-IL-1R3 IgG1-LALA antibodies inhibit activation of immune cells in whole blood, whole blood of 8 donors was stimulated with heat-inactivated *Candida albicans*. The representative humanized anti-IL-1R3 IgG1-LALA antibody according to the invention shown in the figure, was able to inhibit *Candida* induced IL-6 cytokine release. Experiments were carried out according to the method described in Example 17.

FIG. 16: Blockage of Cytokine Release in Mixed Lymphocyte Reactions (MLR)

The ability of humanized anti-IL-1R3 IgG1-LALA antibodies to block release of diverse cytokines was tested in mixed lymphocyte reactions (MLR) using PBMCs of healthy, unmatched donors. The representative humanized anti-IL-1R3 IgG1-LALA antibody according to the invention shown in the figure was able to inhibit release of IFNg, IL-6, TNF-a, IL-13, IL-17 and IL-10. Experiments were carried out according to the method described in Example 18.

The invention claimed is:

1. A method of treating cancer in a patient suffering therefrom, comprising administering to a patient an antibody that specifically binds to IL-1R3 or a fragment or derivative thereof, the antibody or fragment or derivative thereof comprising:
   a) a heavy chain variable region (VH) comprising the complementarity determining regions comprising CDR-H1, CDR-H2, and CDR-H3
      wherein the CDR-H1 region comprises an amino acid sequence set forth in SEQ ID NO: 77,
      wherein the CDR-H2 region comprises an amino acid sequence set forth in SEQ ID NO: 94,
      and wherein the CDR-H3 region comprises an amino acid sequence set forth in SEQ ID NO: 111; and
   b) a light chain variable region (VL) comprising the complementarity determining regions comprising CDR-L1, CDR-L2, and CDR-L3
      wherein the CDR-L1 region comprises an amino acid sequence set forth in SEQ ID NO: 128,
      wherein the CDR-L2 region comprises an amino acid sequence set forth in SEQ ID NO: 145, and
      wherein the CDR-L3 region comprises an amino acid sequence set forth in SEQ ID NO: 162.

2. The method of claim 1, wherein the heavy chain variable (VH) region comprises an amino acid sequence set forth in SEQ ID NO: 26, and the light chain variable (VL) region comprises an amino acid sequence set forth in SEQ ID NO: 60.

3. The method of claim 1, wherein the antibody or fragment or derivative thereof comprises a human IgG1 Fc region comprising at least amino acid substitutions at L234A and L235A of the human IgG1 Fc region, wherein the numbering of amino acid residues in the Fc region or constant region is according to the EU numbering system.

4. The method of claim 1, wherein the cancer is selected from the group consisting of lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, or uterine cancer.

5. The method of claim 1, wherein the antibody or fragment or derivative thereof comprises a human IgG4 Fc region comprising at least amino acid substitutions at S228P and L235E of the human IgG4 Fc region, wherein the numbering of amino acid residues in the Fc region or constant region is according to the EU numbering system.

6. The method of claim 1, wherein the cancer is leukemia or lymphoma.

7. A method of treating cancer in a patient suffering therefrom, the method comprising administering to the patient a therapeutically effective amount of an antibody that specifically binds to IL-1R3 or a fragment or derivative thereof in combination with one or more cytotoxic, cytostatic or targeted anti-cancer compounds, wherein the antibody or fragment or derivative thereof comprises:
   a) a heavy chain variable region (VH) comprising the complementarity determining regions comprising CDR-H1, CDR-H2, and CDR-H3 wherein the CDR-H1 region comprises an amino acid sequence set forth in SEQ ID NO: 77, wherein the CDR-H2 region comprises an amino acid sequence set forth in SEQ ID NO: 94, and wherein the CDR-H3 region comprises an amino acid sequence set forth in SEQ ID NO: 111; and b) a light chain variable region (VL) comprising the complementarity determining regions comprising CDR-L1, CDR-L2, and CDR-L3 wherein the CDR-L1 region comprises an amino acid sequence set forth in SEQ ID NO: 128, wherein the CDR-L2 region comprises an amino acid sequence set forth in SEQ ID NO: 145, and wherein the CDR-L3 region comprises an amino acid sequence set forth in SEQ ID NO: 162.

8. A method of treating cancer in a patient, comprising administering to a patient an antibody that specifically binds to IL-1R3, wherein the antibody comprises:

a) a VH region comprising an amino acid sequence set forth in SEQ ID NO: 26;

b) a VL region comprising an amino acid sequence set forth in SEQ ID NO: 60; and c) a human IgG1 Fc region comprising at least amino acid substitutions at L234A and L235A of the human IgG1 Fc region, wherein the numbering of amino acid residues in the Fc region or constant region is according to the EU numbering system.

9. The method according to claim 8, wherein the cancer is selected from the group consisting of lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, or uterine cancer.

10. The method of claim 8, wherein the antibody is administered in combination with one or more cytotoxic, cytostatic or targeted anti-cancer compounds.

11. The method of claim 8, wherein the cancer is leukemia or lymphoma.

12. A method of treating cancer in a patient, comprising administering to a patient an antibody that specifically binds to IL-1R3, the antibody comprising:

a) a VH region comprising an amino acid sequence set forth in SEQ ID NO: 26;

b) a VL region comprising an amino acid sequence set forth in SEQ ID NO: 60; and c) a human IgG4 Fc region comprising at least amino acid substitutions at S228P and L235E of the human IgG4 Fc region, wherein the numbering of amino acid residues in the Fc region or constant region is according to the EU numbering system.

13. The method according to claim 12, wherein the cancer is selected from the group consisting of lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, or uterine cancer.

14. The method of claim 12, wherein the antibody is administered in combination with one or more cytotoxic, cytostatic or targeted anti-cancer compounds.

15. The method of claim 12, wherein the cancer is leukemia or lymphoma.

* * * * *